United States Patent [19]

Thompson

[11] Patent Number: 4,881,968

[45] Date of Patent: Nov. 21, 1989

[54] HERBICIDAL SULFONAMIDES

[75] Inventor: Mark E. Thompson, Wilmington, Del.

[73] Assignee: E. I. Du Pont de Nemours and Company, Wilmington, Del.

[21] Appl. No.: 117,769

[22] Filed: Nov. 5, 1987

[51] Int. Cl.$^4$ .................. A01N 43/54; C07D 239/64; C07D 401/12; C07D 403/12

[52] U.S. Cl. .................................. 71/92; 71/90; 544/320; 544/321; 544/323; 544/324; 544/331; 544/332; 544/310; 544/311; 544/317; 544/319; 544/327; 544/328; 544/329

[58] Field of Search ...................... 71/92, 90; 544/320, 544/321, 323, 324, 331, 332, 310, 311, 317, 319, 327, 328, 329

[56] References Cited

U.S. PATENT DOCUMENTS

| | | | |
|---|---|---|---|
| 4,383,113 | 5/1983 | Levitt | 544/211 |
| 4,435,206 | 3/1984 | Levitt | 71/92 |
| 4,481,029 | 11/1984 | Levitt | 71/93 |
| 4,549,898 | 10/1985 | Bohner et al. | 71/90 |
| 4,661,147 | 4/1987 | Dumas | 71/92 |

Primary Examiner—John M. Ford

[57] ABSTRACT

This application relates to ortho-carboxylate ester sulfonylureas which are useful as agricultural chemicals and in particular have high herbicidal activity while showing tolerance to certain crops.

37 Claims, No Drawings

HERBICIDAL SULFONAMIDES

BACKGROUND OF THE INVENTION

This application relates to certain ortho-carboxylate ester sulfonylureas which are useful as agricultural chemicals and in particular have high herbicidal activity while showing activity to certain crops.

U.S. Pat. No. 4,383,113 and U.S. Pat. No. 4,394,506 include the disclosure of o-alkoxycarbonylbenzenesulfonylureas.

U.S. Pat. No. 4,435,206 and U.S. Pat. No. 4,544,401 disclose pyridinesulfonylureas which may be substituted at the carbon adjacent to the sulfonylurea bridge by $CO_2(C_1-C_6$ alkyl).

U.S. Pat. No. 4,481,029 discloses herbicidal o-alkoxycarbonylthiophenesulfonylureas.

European Pat. No. 95,925, published 12/7/83, discloses herbicidal pyrazolesulfonylureas containing ortho-carboxylic acid esters.

U.S. Pat. No. 4,661,147 discloses herbicidal sulfonylureas containing ortho-carboxylic esters, $CO_2R_1$, wherein $R_1$ is $C_2-C_5$ alkyl, $C_4$ alkenyl or $C_4$ alkynyl substituted with one or two substituents selected from: OH, SH, $OC(W_1)R_{17}$, $SC(O)R_{17}$, $OC(W_1)OR_{17}$, $SC(O)OR_{17}$, $OC(W_1)NR_8R_{17}$, $SC(O)NR_8R_{17}$, $OC(W_1)NH_2$, $SC(O)NH_2$, $OC(W_1)NR_8A$, $OP(W_1)(OR_{10})_2$, $SP(W_1)(OR_{10})_2$, $OSO_2R_{17}$, $OSO_2NR_8R_{17}$, $OSi(R_9)_2R_{10}$, $S(O)_nR_7$, $NR_7R_8$,

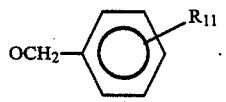

U.S. Pat. No. 4,549,898, issued 10/29/85 (Swiss priority 6/14/82), discloses herbicidal sulfonylureas of formula

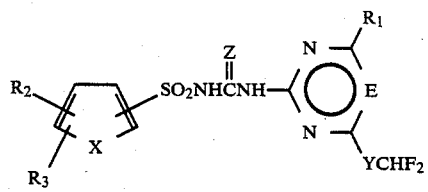

wherein
  $R_2$ includes H, $C_1-C_3$ alkyl, $C_1-C_3$ haloalkyl, halogen, $NO_2$, $C_1-C_3$ alkoxy, $C(W)R_8$, $SO_2NR_6R_7$, $S(O)_n-C_1-C_3$ alkyl or $COR_9$;
  $R_9$ includes $C_1-C_6$ alkoxy, $C_3-C_6$ alkenyloxy, $C_3-C_6$ alkynyloxy, $C_2-C_6$ haloalkoxy, $C_1-C_4$ cyanoalkoxy, $C_1-C_6$ alkylthio, $C_3-C_6$ alkenylthio, $C_3-C_6$ alkynylthio, $C_5-C_6$ cycloalkoxy, $C_4-C_7$ cycloalkylalkoxy, $NR_6R_7$ or alkoxyalkoxy.

None of these patents discloses inter alia o-alkoxycarbonylaromatic sulfonylureas wherein the o-alkoxy group terminates in $N_3$, SCN or $NO_2$.

SUMMARY OF THE INVENTION

This invention pertains to novel compounds of Formula I, their agriculturally suitable compositions and their method-of-use as preemergent and/or postemergent herbicides or plant growth regulants, as follows.

wherein
J is

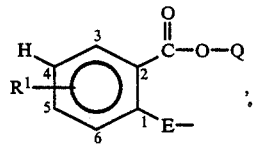
J-1

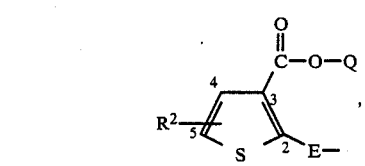
J-2

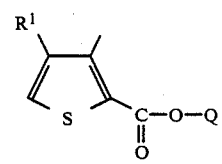
J-3

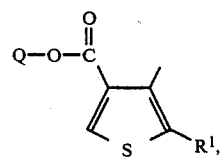
J-4

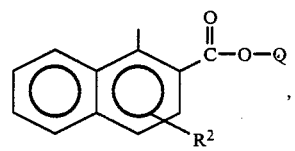
J-5

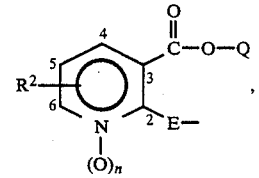
J-6

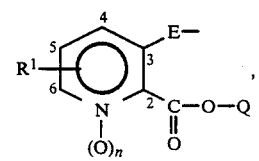
J-7

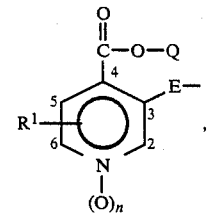
J-8

-continued

J-9, J-10, J-11, J-12 (structures)

Q is

—CH—CH—Q₁ or —CH—CH—CH—Q₁;
  |   |              |   |   |
  Q₃  Q₂             Q₄  Q₃  Q₂

$Q_1$ is $N_3$, SCN or $NO_2$;
$Q_2$, $Q_3$ and $Q_4$ are independently H or $CH_3$;
E is a single bond or —$CH_2$—;
R is H or $CH_3$;
W is O or S;
$R^1$ is H, $C_1$-$C_3$ alkyl, $C_1$-$C_3$ haloalkyl, halogen, CN, nitro, $C_1$-$C_3$ alkoxy, $C_1$-$C_3$ haloalkoxy, $C_1$-$C_3$ alkylthio, $C_1$-$C_3$ alkylsulfinyl, $C_1$-$C_3$ alkylsulfonyl, $SCF_2H$, $NH_2$, $NHCH_3$, $N(CH_3)_2$ or $C_1$-$C_2$ alkyl substituted with one $C_1$-$C_2$ alkoxy, $C_1$-$C_2$ haloalkoxy, SH, $SCH_3$, CN or OH;
$R^2$ is H, F, Cl, Br, $C_1$-$C_2$ alkyl, $C_1$-$C_2$ haloalkyl or $C_1$-$C_2$ alkoxy;
$R^3$ is H, $C_1$-$C_3$ alkyl, $C_1$-$C_2$ haloalkyl, $C_3$-$C_4$ alkenyl, $C_3$-$C_4$ alkynyl, $CH_2CN$, phenyl or phenyl substituted by F, Cl, $CH_3$ or $OCH_3$;
n is 0 or 1;
A is A-1, A-2, A-3, A-4, A-5, A-6, A-7 (structures)

X is H, $C_1$-$C_4$ alkyl, $C_1$-$C_4$ alkoxy, $C_1$-$C_4$ haloalkoxy, $C_1$-$C_4$ haloalkyl, $C_1$-$C_4$ haloalkylthio, $C_1$-$C_4$ alkylthio, halogen, $C_2$-$C_5$ alkoxyalkyl, $C_2$-$C_5$ alkoxyalkoxy, amino, $C_1$-$C_3$ alkylamino, di($C_1$-$C_3$ alkyl)amino or $C_3$-$C_5$ cycloalkyl;
Y is H, $C_1$-$C_4$ alkyl, $C_1$-$C_4$ alkoxy, $C_1$-$C_4$ haloalkoxy, $C_1$-$C_4$ haloalkylthio, $C_1$-$C_4$ alkylthio, $C_2$-$C_5$ alkoxyalkyl, $C_2$-$C_5$ alkoxyalkoxy, amino, $C_1$-$C_3$ alkylamino, di($C_1$-$C_3$ alkyl)amino, $C_3$-$C_4$ alkenyloxy, $C_3$-$C_4$ alkynyloxy, $C_2$-$C_5$ alkylthioalkyl, $C_1$-$C_4$ haloalkyl, $C_2$-$C_4$ alkynyl, azido, cyano, $C_2$-$C_5$ alkylsulfinylalkyl, $C_2$-$C_5$ alkylsulfonylalkyl, (structures)

$CH_2CN$, $CH_2CO_2CH_3$, $CH_2OH$ or $N(OCH_3)CH_3$;
m is 2 or 3;
$L_1$ and $L_2$ are independently O or S;
$R_a$ is H or $C_1$-$C_3$ alkyl;

$R_b$ and $R_c$ are independently $C_1$-$C_3$ alkyl;
Z is CH or N;
$Z_1$ is CH or N;
$Y_1$ is O or $CH_2$;
$X_1$ is $CH_3$, $OCH_3$, $OC_2H_5$ or $OCF_2H$;
$X_2$ is $CH_3$, $C_2H_5$ or $CH_2CF_3$;
$Y_2$ is $OCH_3$, $OC_2H_5$, $SCH_3$, $SC_2H_5$, $CH_3$ or $CH_2CH_3$;
$X_3$ is $CH_3$ or $OCH_3$;
$Y_3$ is H or $CH_3$;
$X_4$ is $CH_3$, $OCH_3$, $OC_2H_5$, $CH_2OCH_3$ or Cl; and
$Y_4$ is $CH_3$, $OCH_3$, $OC_2H_5$ or Cl;
and their agriculturally suitable salts; provided that
  (a) when X is Cl, F, Br or I, then Z is CH and Y is $OCH_3$, $OC_2H_5$, $N(OCH_3)CH_3$, $NHCH_3$, $N(CH_3)_2$ or $OCF_2H$;
  (b) when X or Y is $C_1$ haloalkoxy, then Z is CH;
  (c) $X_4$ and $Y_4$ are not simultaneously Cl;
  (d) when W is S, then R is H, A is A-1 and Y is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH$, $OCH_2CH_2OCH_3$, $CH(OCH_3)_2$ or 1,3-dioxolan-2-yl; and
  (e) $Q_2$, $Q_3$ and $Q_4$ are not simultaneously methyl.

In the above definitions, the term "alkyl", used either alone or in compound words such as "alkylthio" or "haloalkyl", denotes straight chain or branched alkyl, e.g. methyl, ethyl, n-propyl, isopropyl or the different butyl isomers.

Alkoxy denotes methoxy, ethoxy, n-propyloxy, isopropyloxy and the different butyl isomers.

Alkenyl denotes straight chain or branched alkenes, e.g., 1-propenyl, 2-propenyl, 3-propenyl and the different butenyl isomers.

Alkynyl denotes straight chain or branched alkynes, e.g. ethynyl, 1-propynyl, 2-propynyl and the different butynyl isomers.

Alkylsulfonyl denotes methylsulfonyl, ethylsulfonyl and the different propylsulfonyl isomers.

Alkylthio, alkylsulfinyl, alkylamino, etc. are defined analogously to the above examples.

Cycloalkyl denotes cyclopropyl, cyclobutyl and cyclopentyl.

The term "halogen", either alone or in compound words such as "haloalkyl", denotes fluorine, chlorine, bromine or iodine. Further, when used in compound words such as "haloalkyl" said alkyl may be partially halogenated or fully substituted with halogen atoms and said halogen atoms may be the same or different. Examples of haloalkyl include $CH_2CH_2F$, $CF_2CF_3$ and $CH_2CHFCl$.

The total number of carbon atoms in a substituent group is indicated by the $C_i$-$C_j$ prefix where i and j are numbers from 1 to 5. For example, $C_1$-$C_3$ alkyl-sulfonyl would designate methylsulfonyl through propylsulfonyl, $C_2$ alkoxyalkoxy would designate $OCH_2OCH_3$, $C_2$ cyanoalkyl would designate $CH_2CN$ and $C_3$ cyanoalkyl would designate $CH_2CH_2CN$ and $CH(CN)CH_3$.

PREFERRED COMPOUNDS

Preferred for reasons of increased ease of synthesis and/or greater herbicidal efficacy are:
1. Compounds of Formula I where
   E is a single bond; and
   W is O.
2. Compounds of Formula I where
   E is $CH_2$; and
   W is O.
3. Compounds of Preferred 1 where X is $C_1$-$C_2$ alkyl, $C_1$-$C_2$ alkoxy, Cl, F, Br, I, $OCF_2H$, $CH_2F$, $CF_3$, $OCH_2CH_2F$, $OCH_2CHF_2$, $OCH_2CF_3$, $CH_2Cl$ or $CH_2Br$;

Y is H, $C_1$-$C_2$ alkyl, $C_1$-$C_2$ alkoxy, $CH_2OCH_3$, $CH_2OCH_2CH_3$, $NHCH_3$, $N(OCH_3)CH_3$, $N(CH_3)_2$, $CF_3$, $SCH_3$, $OCH_2CH=CH_2$, $OCH_2C\equiv CH$, $OCH_2CH_2OCH_3$, $CH_2SCH_3$,

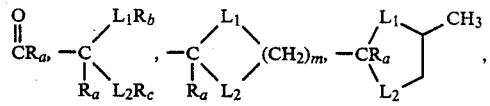

$OCF_2H$, $SCF_2H$, $OCF_2Br$, cyclopropyl, $C\equiv CH$ or $C\equiv CCH_3$;
$R_a$ is H or $CH_3$; and
$R_b$ and $R_c$ are $C_1$-$C_2$ alkyl.
4. Compounds of Preferred 3 where
A is A-1;
n is 0;
X is $CH_3$, $OCH_3$, $OCH_2CH_3$, Cl or $OCF_2H$; and
Y is $CH_3$, $OCH_3$, $C_2H_5$, $CH_2OCH_3$, $NHCH_3$, $CH(OCH_3)_2$ or cyclopropyl.
5. Compounds of Preferred 4 where
R is H;
$R^1$ is H, $CH_3$, $CF_3$, Cl, CN, $SCH_3$, $NHCH_3$, $N(CH_3)_2$, $CH_2OCH_3$ or $CH_2CN$;
$R^2$ is H, Cl, Br, $CH_3$ or $OCH_3$; and
$R^3$ is H, $CH_3$, $CH_2CF_3$ or phenyl.
6. Compounds of Preferred 5 where J is J-1.
7. Compounds of Preferred 5 where J is J-2.
8. Compounds of Preferred 5 where J is J-3.
9. Compounds of Preferred 5 where J is J-4.
10. Compounds of Preferred 5 where J is J-5.
11. Compounds of Preferred 5 where J is J-6.
12. Compounds of Preferred 5 where J is J-7.
13. Compounds of Preferred 5 where J is J-8.
14. Compounds of Preferred 5 where J is J-9.
15. Compounds of Preferred 5 where J is J-10.
16. Compounds of Preferred 5 where J is J-11.
17. Compounds of Preferred 5 where J is J-12.
18. Compounds of Preferred 5 wherein $Q_1$ is $N_3$.
19. Compounds of Preferred 5 wherein $Q_1$ is SCN.
20. Compounds of Preferred 5 wherein $Q_1$ is $NO_2$.

Specifically Preferred for reasons of greatest ease of synthesis and/or greatest herbicidal efficacy are:
2-[[(4,6-Dimethoxypyrimidin-2-yl)aminocarbonyl-]aminosulfonyl]benzoic acid, 2-azidoethyl ester, m.p. 162.5°–164° C.; and
2-[[(4-Methoxy-6-methyl-1,3,5-triazin-2-yl)-aminocarbonyl]aminosulfonyl]benzoic acid, 2-azidoethyl ester, m.p. 168°–169.5° C.

This invention also pertains to novel compounds of the formula $$JSO_2-X_a$$

wherein
J is as previously defined; and
$X_a$ is $NH_2$ or $HNC(O)OC_6H_5$, which are useful as intermediates to herbicidal sulfonylureas.

Preferred sulfonyl derivatives are included in the following formula

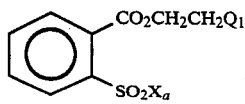

wherein $X_a$ and $Q_1$ are as previously defined.

DETAILED DESCRIPTION OF THE INVENTION

Compounds of Formula I can be prepared by one or more of the procedures depicted in Equations 1, 2 and 3, where J, W, R and A are as previously defined.

Equation 1

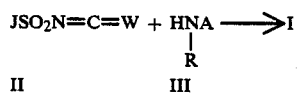

The reaction of Equation 1 is carried out according to the procedures taught in U.S. Pat. No. 4,127,405. The requisite sulfonylisocyanates of Formula II (W is O) can be synthesized by methods taught in U.S. Pat. No. 4,238,621. Sulfonylisothiocyanates of Formula II (W is S) are prepared as described in *Arch. Pharm.*, 1966, 299, 174.

Equation 2

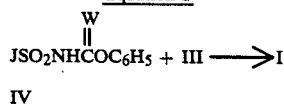

The reaction of Equation 2 is carried out by contacting phenylcarbamates or phenylthiocarbamates of Formula IV with aminoheterocycles of Formula III in an inert organic solvent such as dioxane or tetrahydrofuran at temperatures of about 20°–100° C. for a period of about one-half to twenty-four hours. The product can be isolated by evaporation of the reaction solvent and purified by chromatography or recrystallization.

Phenylcarbamates and phenylthiocarbamates of Formula IV can be prepared by the methods described, or modifications thereof known to those skilled in the art, in U.S. Pat. No. 4,443,243.

Equation 3

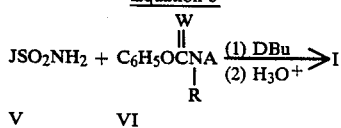

The reaction of Equation 3 is carried out according to the procedures taught in South African Patent Application 830441. Thus, treatment of a solution of the sulfonamide of Formula V and appropriate phenylcarbamate or phenylthiocarbamate VI in a solvent such as dioxane or acetonitrile at about 0°–25° C. with one equivalent of a suitable base such as 1,8-diazabicyclo[5.4.0]undec-7-ene (DBu) for approximately 15 to 90 minutes, followed by acidification with aqueous hydrochloric acid affords the sulfonylureas of Formula I.

The phenylcarbamates VI can be synthesized by treatment of the corresponding heterocyclic amines of Formula III with diphenyl carbonate or phenyl chloroformate in the presence of a base such as sodium hydride, pyridine or potassium carbonate with a catalytic amount of 4-dimethylaminopyridine. This mixture is stirred at temperatures between 25° and 65° C. in a suitable solvent such as tetrahydrofuran for about 12 to 36 hours as described in South African Patent Applications 825671 and 825045.

The requisite sulfonamides of Formula Va (below) can be prepared via nucleophilic displacement of an appropriate leaving group 'G' as illustrated in Equation 4. For the sake of conciseness, this transformation is shown only for compounds of Formula V in which J is J-1 and E is a single bond. It will be readily recognized by those skilled in the art that this reaction, and those that follow, apply equally well for all sulfonamides of general Formula V in which J is J-1 through J-12.

Equation 4

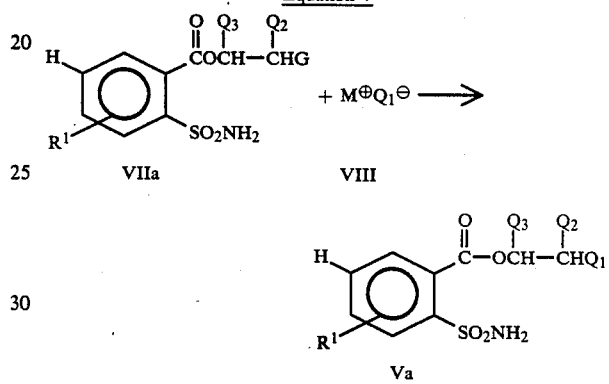

wherein $Q_1$, $Q_2$, $Q_3$ and $R^1$ are as previously defined, M is Na or K, and G is Br, I, $OSO_2CH_3$ or $OSO_2C_6H_4CH_3$.

The reaction of Equation 4 is carried out in a polar solvent such as methanol, ethanol, acetonitrile, dimethylsulfoxide or carbitol. Treatment of the halide or sulfonate sulfonamide VIIa with one or more equivalents of the appropriate azide, nitrite or thiocyanate salt of Formula VIII at temperatures of about 65°–100° C. for 1 to 72 hours provides the desired product after extraction. The sulfonamides of Formula Va are typically purified by chromatography on silica gel.

In an analogous manner, sulfonamides of Formula Vb can be prepared as shown in Equation 5.

Equation 5

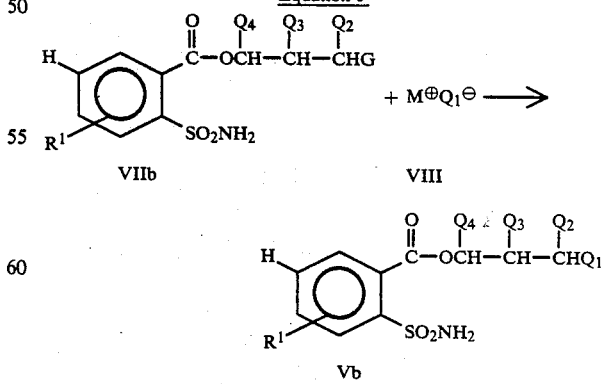

wherein $Q_1$, $Q_2$, $Q_3$, $Q_4$ and $R^1$ are as previously defined, M is Na or K, and G is Br, I, $OSO_2CH_3$ or $OSO_2C_6H_4CH_3$.

It will be recognized by one skilled in the art that the reaction conditions of Equations 4 and 5 may not be compatible with substrates VIIa and VIIb when $R^1$ is $C_1$–$C_3$ haloalkyl or $C_1$–$C_3$ haloalkoxy. In these cases, an appropriately-positioned hydroxyl group will serve as a precursor for the halogen atom on the substituent $R^1$. After the displacement reactions of Equations 4 and 5 have been carried out, the hydroxyl substituent on $R^1$ can be transformed into a halogen by procedures which are well known to those skilled in the art. For a compilation of these procedures, refer to March, "Advanced Organic Chemistry", 3rd Edition, John Wiley and Sons, N.Y. 1985, pp. 382–384.

Alternatively, for compounds in which $R^1$ is $C_1$–$C_3$ haloalkoxy, the reactions of Equations 4 and 5 can be conducted on substrates of Formulas VIIa and VIIb wherein $R^1$ is —OH, or a suitably protected form of —OH. After the displacement reactions of Equations 4 and 5 have been carried out, the phenol can be alkylated with the appropriate alkyl halide. For examples of conditions employed to effect alkylation of phenols, see Feuer and Hooz, in Patai, "The Chemistry of the Ether Linkage" Interscience, N.Y., 1967, pp. 446–450, 460–468; *Synthesis*, 1979, 428; and *Tetrahedron*, 1979, 35, 2169.

Primary sulfonamides of Formula VIIa are prepared by treatment of the corresponding N-t-butylsulfonamides of Formula IX with acid as shown in Equation 6.

Equation 6

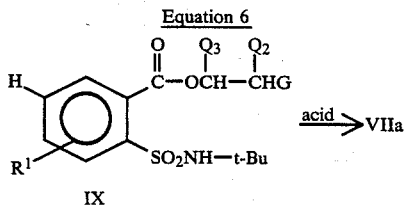

wherein $Q_2$, $Q_3$, $R^1$ and G are as previously defined.

The reaction of Equation 6 is carried out by treatment of the N-t-butylsulfonamide IX with excess trifluoroacetic acid at about 25°–72° C. for 1–24 hours. Removal of the volatiles and crystallization of the residue typically affords the pure sulfonamide of Formula VIIa. In certain cases, further purification can be achieved by recrystallization from a solvent such as n-chlorobutane or ethyl acetate, or by chromatography on silica gel. Alternatively, the reaction of Equation 6 can be effected by the use of p-toluenesulfonic acid in a solvent such as toluene or xylene at reflux temperature, or by polyphosphoric acid.

The homologous primary sulfonamides of Formula VIIb are prepared in a similar fashion from the appropriate N-t-butylsulfonamides.

Sulfonamides of Formulas VIIa and VIIb, wherein G is methanesulfonate or p-toluenesulfonate, can be synthesized according to methods taught in U.S. Pat. No. 4,661,147.

The requisite N-t-butylsulfonamides of Formula IX can be prepared by a number of procedures. Compounds of Formula IX in which G is Br or I are prepared as shown in Equation 7 by esterification of a carboxylic acid of Formula X.

Equation 7

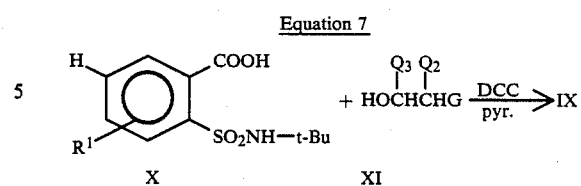

wherein $R^1$, $Q_2$ and $Q_3$ are as previously defined and G is Br or I.

The reaction of Equation 7 is carried out by treating the acid X with an appropriate alcohol of Formula XI in the presence of a slight excess of dicyclohexylcarbodiimide (DCC) and one equivalent of pyridine. The reaction is conducted in a solvent such as methylene chloride, acetonitrile, N,N-dimethylformamide, or mixtures of these at temperatures of 0°–25° C. for 1–24 hours. The by-product dicyclohexylurea is typically removed by filtration, and the filtrate is concentrated to give the crude product. Purification can be achieved by chromatography on silica gel.

Certain carboxylic acids of Formula X are known in the literature. For example, the preparation of 2-carboxy-N-t-butyl benzenesulfonamide (X; $R^1$=H), and simple derivatives thereof, is described in *J. Org. Chem.*, 1973, 38, 1974. Many of the compounds of Formula X can be prepared in a similar manner, via ortho-metallation of the appropriate N-t-butylsulfonamides of Formula XII with a strong base such as n-butyllithium, and subsequent carbonylation with carbon dioxide as illustrated in Equation 8.

Equation 8

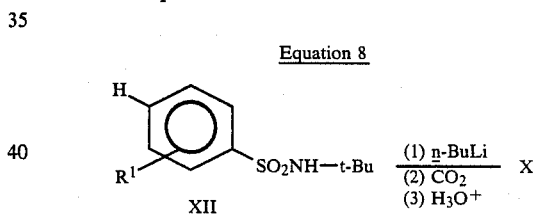

wherein $R^1$ is as previously defined.

Many of the requisite N-t-butylsulfonamides of Formula XII are known in the literature; those that are not specifically known are readily prepared by methods that would be obvious to one skilled in the art.

Similarly, most of the alcohols of Formula XI are known in the literature, and many are available commercially. Those that are not can be prepared by procedures that would be obvious to one skilled in the art.

Certain values of $R^1$ in compounds of Formula X will not be compatible with the synthetic procedure represented in Equation 8. These N-t-butylsulfonamides can be synthesized via the three-step sequence depicted in Equations 9(a), 9(b) and 9(c).

Equation 9

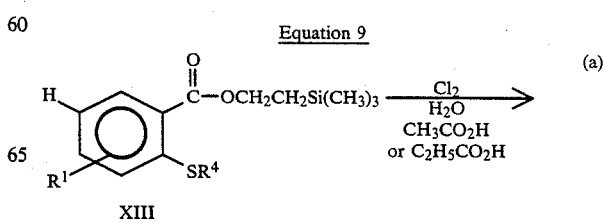

-continued

Equation 9

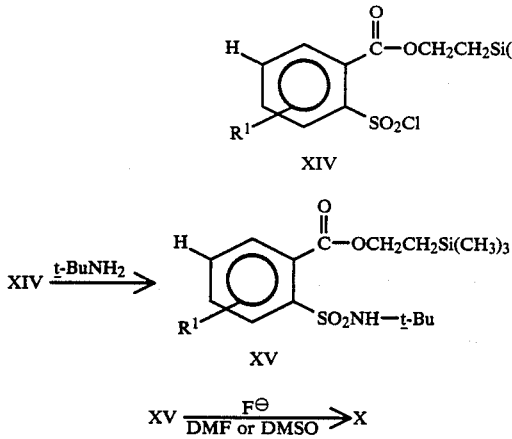

(b)
XIV $\xrightarrow{\text{t-BuNH}_2}$

XV $\xrightarrow[\text{DMF or DMSO}]{\text{F}^\ominus}$ X  (c)

wherein $R^1$ is as previously defined and $R^4$ is $C_2$–$C_3$ alkyl or benzyl.

The reaction of Equation 9(a) is carried out by contacting a suspension of thioether XIII in a solvent such as acetic or propionic acid in the presence of at least 2.5 equivalents of water and at least 3.0 equivalents of chlorine at about −20° to 30° C. for 0.2 to 5 hours. The reaction mixture is poured into ice-water and the product is isolated by filtration or extraction with a solvent such as methylene chloride. The extraction product is optionally washed with aqueous sodium bicarbonate until neutral or slightly basic to litmus, then dried, and the solvent is evaporated to yield a product sufficiently pure to be carried directly on to the next step.

Alternatively, reaction of thioether XIII, wherein $R^4$ is benzyl, with a hypochlorite solution, i.e., NaOCl, can provide sulfonyl chloride XIV. For additional details, see analogous reactions in South African Patent Application No. 84/8845 and 84/8844.

The reaction of Equation 9(b) is effected by treating a solution of at least two equivalents of t-butylamine in a solvent such as tetrahydrofuran or chloroform at −50° C. to 0° C. with a solution of the sulfonyl chloride XIV in the same solvent. After being stirred at room temperature for 0.5 to 5 hours, the desired N-t-butylsulfonamide XV is isolated by either filtration (to remove the by-product t-butylamine hydrochloride) and concentration of the filtrate, or by washing the organic solution with several small portions of water, drying and evaporation of the organic layer. The crude product can be purified by recrystallization or chromatography on silica gel.

The reaction of Equation 9(c) is carried out by contacting a solution of the silyl ester of Formula XV in a solvent such as N,N-dimethylformamide or dimethyl sulfoxide at 20°–30° C. with two equivalents of either tetraethylammonium fluoride or tetra-n-butylammonium fluoride for 5–60 minutes. The reaction mixture is typically poured into ice-water and acidified to pH 1–2. Filtration of the insoluble solids or extraction into a suitable solvent such as methylene chloride or ethyl acetate, and evaporation of the organic layer affords the carboxylic acid X.

Equation 10 illustrates the preparation of the requisite thioethers of Formula XIII via nucleophilic substitution of an appropriate 2-chlorotrimethylsilyl ester of Formula XVI with a mercaptide salt XVII.

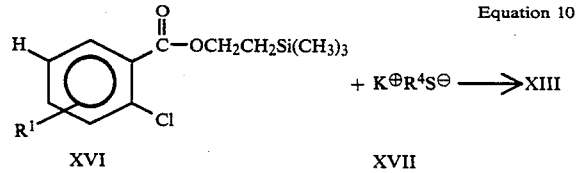

wherein $R^1$ is as previously defined and $R^4$ is $C_2$–$C_3$ alkyl or benzyl.

The mercaptide salt of Formula XVII is generally prepared in situ by addition of the appropriate mercaptan ($R^4$SH) to a cooled suspension of a base such as potassium t-butoxide in N,N-dimethylformamide or dimethyl sulfoxide. This suspension is stirred at room temperature for 15–60 minutes, and a solution of the silyl ester XVI in the same solvent is added at 0°–30° C. The reaction mixture is stirred for 3–12 hours, poured into ice-water and isolated by filtration or extraction into a solvent such as diethyl ether.

The requisite silyl esters of Formula XVI can be prepared as shown in Equation 11 by esterification of a suitable carboxylic acid XVIII with trimethylsilyl ethanol.

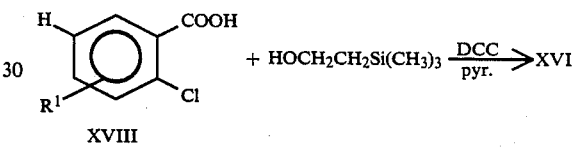

wherein $R^1$ is as previously defined.

The reaction of Equation 11 is carried out by treating the acid XVIII with 1.0 to 1.5 equivalents of trimethylsilyl ethanol in the presence of a slight excess of dicyclohexylcarbodiimide (DCC) and one equivalent of pyridine. For a detailed procedure, refer of Helv. Chim. Acta, 1977, 60, 2711.

Many of the 2-chlorobenzoic acid derivatives of Formula XVIII are known in the literature or are commercially available. Those that are not can be readily synthesized by procedures that would be well-known to one skilled in the art.

The heterocyclic amines of Formula III in Equations 1 and 2 above can be prepared by methods known in the literature, or simple modifications thereof, by those skilled in the art. For instance, European Pat. No. 84,224 and Braker et al., J. Chem. Soc., 69, 3072 (1947), describe methods for preparing aminopyridines and triazines substituted by acetal groups such as dialkoxymethyl or 1,3-dioxolan-2-yl, among other groups. Also, South African Patent Application Nos. 82/5045 and 82/5671 describe methods for preparing aminopyrimidines and triazines substituted by haloalkyl or haloalkylthio groups such as $OCH_2CH_2F$, $OCH_2CF_3$, $SCF_2H$, and $OCF_2H$. South African Patent Application 83/7434 describes methods for the synthesis of cyclopropylpyrimidines and triazines substituted by such groups as alkyl, haloalkyl, alkoxy, haloalkoxy, alkylamino, dialkylamino or alkoxyalkyl.

The 5,6-dihydrofuro[2,3-d]pyrimidine-2-amines, the cyclopenta[d]pyrimidines-2-amines (III, A is A-2) and the 6,7-dihydro-5H-pyrano[2,3-d]pyrimidin-2-amines (III, A is A-3) can be prepared as described in U.S. Pat. No. 4,339,267. The furo[2,3-d]pyrimidin-2-amines (III, A is A-4) are described in U.S. Pat. No. 4,487,626. Compounds of Formula III, where A is A-7, are described in European Pat. No. 125,864.

Compounds of Formula III, where A is A-5, are described in U.S. Pat. No. 4,421,550. Compounds of Formula III where A is A-6, are described in U.S. Pat. No. 4,496,392.

In addition, general methods for preparing aminopyrimidines and triazines have been reviewed in the following publications: "The Chemistry of Heterocyclic Compounds", a series published by Interscience Publ., N.Y. and London; "Pyrimidines", Vol. 16 of the same series by Brown; "s-Triazines and Derivatives", Vol. 13 of the same series by Smolin et al.; U.S. Pat. No. 3,154,547; and Huffman et al., *J. Org. Chem.*, 28, pages 1812 to 1816 (1963), which describes the synthesis of triazines.

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide, or carbonate). Quaternary amine salts can be made by similar techniques.

Salts of compounds of Formula I can also be prepared by exchange of one cation for another. Cationic exchange can be effected by direct contact of an aqueous solution of a salt of a compound of Formula I (e.g., alkali or quaternary amine salt) with a solution containing the cation to be exchanged. This method is most effective when the desired salt containing the exchanged cation is insoluble in water and can be separated by filtration.

Exchange can also be effected by passing an aqueous solution of a salt of a compound of Formula I (e.g., an alkali metal or quaternary amine salt) through a column packed with a cation exchange resin containing the cation to be exchanged for that of the original salt and the desired product is eluted from the column. This method is particularly useful when the desired salt is water-soluble, e.g., a potassium, sodium or calcium salt.

Acid addition salts, useful in this invention, can be obtained by reacting a compound of Formula I with a suitable acid, e.g., p-toluenesulfonic acid, trichloroacetic acid or the like.

The preparation of the compounds of this invention is further illustrated by the following specific examples. Unless otherwise indicated, all reactions were conducted under an atmosphere of nitrogen.

EXAMPLE 1

2-((1,1-Dimethylethyl)aminosulfonyl)benzoic acid, 2-iodoethyl ester

A solution of 4 g of 2-((1,1-dimethylethyl)aminosulfonyl)benzoic acid (J. G. Lombardino, *J. Org. Chem.*, 1973, 38, 1974) in 16 mL of dry acetonitrile and 1 mL dry N,N-dimethylformamide (DMF) was mixed at room temperature with 1.5 mL of 2-iodoethanol. This mixture was cooled to 0° C. and treated with 3.5 g of dicyclohexylcarbodiimide and then 2.5 mL dry pyridine. The thick suspension was stirred at room temperature for 5 hours, recooled, and 1 mL of 5 M oxalic acid in DMF was added. After being stirred at room temperature for 30 minutes, the solids were removed by filtration and washed well with ethyl acetate. Concentration of the filtrate gave a yellow oil, which was purified by flash chromatography on silica gel. Elution with 45% methylene chloride/hexane gave 3.3 g of a white solid, which was shown by $^1$H NMR analysis to consist of a mixture of the desired product and N-t-butylsaccharin; NMR (CDCl$_3$): δ 1.27 (s, 9H), 3.44 (t, 2H, J=7 Hz), 4.63 (t, 2H, J=7 Hz), 5.96 (br s, 1H), 7.63 (m, 2H), 7.9 (m, 1H), 8.15 (m, 1H).

EXAMPLE 2

2-(Aminosulfonyl)benzoic acid, 2-iodoethyl ester

The product from Example 1 (1 g) was added to 8 mL of trifluoroacetic acid, and the clear solution was stirred at room temperature for 4–5 hours. Removal of the volatiles in vacuo afforded an orange oil, which was subjected to silica gel chromatography. Elution with 4:1 hexane/ethyl acetate gave 650 mg of the title sulfonamide as a white powder, m.p. 76°–79° C.; IR (nujol): 1720, 1730, 3290, 3400 cm$^{-1}$.

EXAMPLE 3

2-(Aminosulfonyl)benzoic acid, 2-azidoethyl ester

A mixture of 1.6 g of the product from Example 2 and 0.3 g of sodium azide in 10 mL absolute ethanol was heated at reflux temperature for 24 hours. Additional sodium azide (0.3 g) was added and the suspension was heated for another 24 hours. The reaction mixture was cooled to room temperature and the ethanol was removed in vacuo. The resultant crude oil was purified by careful chromatography on silica gel. Elution with 1:1 hexane/ethyl acetate gave 0.5 g of the desired product as a colorless, viscous oil; IR (film): 1720, 2100 cm$^{-1}$; NMR (CDCl$_3$): δ 3.67 (t, 2H, J=4 Hz), 4.55 (t, 2H, J=4 Hz), 5.77 (br s, 2H), 7.65 (m, 2H), 7.9 (m, 1H), 8.15 (m, 1H).

EXAMPLE 4

2-[[(4,6-Dimethoxypyrimidin-2-yl)aminocarbonyl]aminosulfonyl]benzoic acid, 2-azidoethyl ester A solution of 0.3 g of the product from Example 3 and 0.3 g of 4,6-dimethoxypyrimidin-2-ylcarbamic acid, phenyl ester in 6 mL of dry acetonitrile was mixed with 0.16 mL 1,8-diazabicyclo[5.4.0]undec-7-ene (DBU). The mixture was stirred at room temperature for 15 minutes, and then 6 mL water was added followed by 10% aqueous hydrochloric acid until a pH of 1-2 was obtained. The precipitate was collected by filtration, washed with water and ether, and was dried to give 0.36 g of the title sulfonylurea as a white powder, m.p. 162.5°–164° C.; IR (nujol): 1730, 2100 cm$^{-1}$; NMR (CDCl$_3$): δ 3.65 (t, 2H, J=6 Hz), 3.99 (6H, s), 4.46 (t, 2H, J=6 Hz), 5.79 (s, 1H), 7.25 (br s, 1H), 7.7–7.8 (m, 3H), 8.42 (dd, 1H), 12.55 (br s, 1H).

EXAMPLE 5

2-[[(4-Methoxy-6-methyl-1,3,5-triazin-2-yl)aminocarbonyl]aminosulfonyl]benzoic acid, 2-azidoethyl ester A solution of 0.2 g of the product from Example 3 and 0.19 g 4-methoxy-6-methyl-1,3,5-triazin-2-yl-carbamic acid, phenyl ester in 4 mL of dry acetonitrile was mixed with 0.11 mL of DBU. The mixture was stirred at room temperature for 15 minutes, and then 4 mL water was added followed by 10% aqueous hydrochloric acid to pH 1-2. The precipitate was collected by filtration, washed with water and ether, and was dried to yield 0.2 g of the title sulfonylurea as a white powder, m.p. 168°–169.5° C.; IR (nujol): 1740, 2100 cm$^{-1}$; NMR (CDCl$_3$): δ 2.62 (s, 3H), 3.64 (t, 2H, J=6 Hz), 4.07 (s, 3H), 4.52 (t, 2H, J=6 Hz), 7.4 (br s, 1H), 7.7–7.8 (m, 3H), 8.4 (dd, 1H), 12.5 (br s, 1H).

Using the procedures described above in Equations 1 through 11 and Examples 1 through 5, or simple modifications thereof, one skilled in the art can readily prepare the compounds in Tables 1 through 9.

| General Formulas For Tables 1 to 9 |
|---|
| General Formula 1 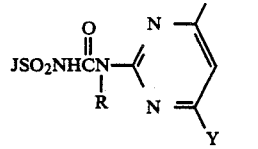 |
| General Formula 2 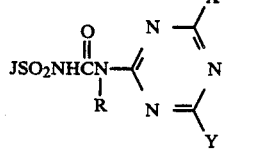 |
| General Formula 3 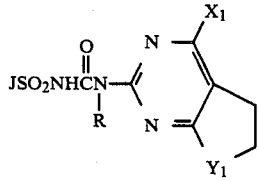 |
| General Formula 4 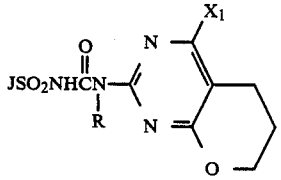 |
| General Formula 5 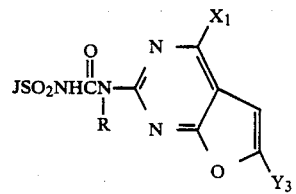 |
| General Formula 6 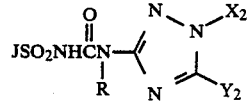 |
| General Formula 7 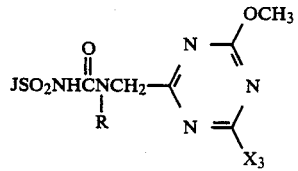 |
| General Formula 8 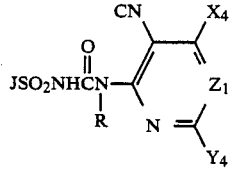 |
| General Formula 9 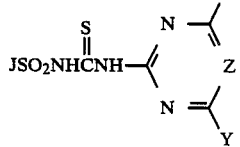 |

TABLE 1

GENERAL FORMULA 1

| J | E | R | $R^1/R^2$ | Q | X | Y | m.p. °C. |
|---|---|---|---|---|---|---|---|
| J-1 | — | H | H | $CH_2CH_2N_3$ | $CH_3$ | $CH_3$ | |
| J-1 | — | H | H | $CH_2CH_2N_3$ | $OCH_3$ | $CH_3$ | 154–156 |
| J-1 | — | H | H | $CH_2CH_2N_3$ | $OCH_3$ | $OCH_3$ | 162.5–164 |
| J-1 | — | H | H | $CH_2CH_2N_3$ | Cl | $OCH_3$ | 157–158.5 |
| J-1 | — | H | H | $CH_2CH_2N_3$ | Br | $OCH_3$ | |
| J-1 | — | H | H | $CH_2CH_2N_3$ | $OCH_3$ | $OCF_2H$ | |
| J-1 | — | H | H | $CH_2CH_2N_3$ | $CH_3$ | $OCF_2H$ | |
| J-1 | — | H | H | $CH_2CH_2N_3$ | $OCF_2H$ | $OCF_2H$ | |
| J-1 | — | H | H | $CH_2CH_2N_3$ | $OCH_3$ | $OCH_2H_5$ | |
| J-1 | — | H | H | $CH_2CH_2N_3$ | $OCH_3$ | $CH(OCH_3)_2$ | |
| J-1 | — | H | H | $CH_2CH_2N_3$ | $CH_3$ | 1,3-dioxolan-2-yl | |
| J-1 | — | H | H | $CH_2CH_2N_3$ | $OCH_3$ | 1,3-dioxolan-2-yl | |
| J-1 | — | H | H | $CH_2CH_2N_3$ | $OCH_3$ | 2-methyl-1,3-oxathiolan-2-yl | |
| J-1 | — | H | H | $CH_2CH_2N_3$ | $OCH_3$ | 1,3-oxathian-2-yl | |
| J-1 | — | H | H | $CH_2CH_2N_3$ | $OCH_3$ | 2-methyl-1,3-dithian-2-yl | |
| J-1 | — | H | H | $CH_2CH_2N_3$ | $OCH_3$ | 4-methyl-1,3-dioxolan-2-yl | |
| J-1 | — | H | H | $CH_2CH_2N_3$ | $OCH_3$ | 2,4-dimethyl-1,3-dithiolan-2-yl | |
| J-1 | — | H | H | $CH_2CH_2N_3$ | H | $CH_3$ | |
| J-1 | — | H | H | $CH_2CH_2N_3$ | $OCH_3$ | H | |
| J-1 | — | H | H | $CH_2CH_2N_3$ | $CF_3$ | $CF_3$ | |
| J-1 | — | H | H | $CH_2CH_2N_3$ | $OCH_2CH_2F$ | $OCH_3$ | |
| J-1 | — | H | H | $CH_2CH_2N_3$ | $OCH_2CHF_2$ | $OCH_3$ | |
| J-1 | — | H | H | $CH_2CH_2N_3$ | $OCH_2CF_3$ | $OCH_3$ | |
| J-1 | — | H | H | $CH_2CH_2N_3$ | $OCH_2CF_3$ | $CH_3$ | |
| J-1 | — | H | H | $CH_2CH_2N_3$ | $CH_3$ | $CH_2OCH_3$ | |
| J-1 | — | H | H | $CH_2CH_2N_3$ | $OCH_3$ | $CH_2OCH_3$ | |
| J-1 | — | H | H | $CH_2CH_2N_3$ | $OCH_3$ | $CH_2OC_2H_5$ | |
| J-1 | — | H | H | $CH_2CH_2N_3$ | $CH_2F$ | $OCH_3$ | |

TABLE 1-continued

GENERAL FORMULA 1

| J | E | R | R$^1$/R$^2$ | Q | X | Y | m.p. °C. |
|---|---|---|---|---|---|---|---|
| J-1 | — | H | H | CH$_2$CH$_2$N$_3$ | CH$_2$Cl | OCH$_3$ | |
| J-1 | — | H | H | CH$_2$CH$_2$N$_3$ | CH$_2$Br | OCH$_3$ | |
| J-1 | — | H | H | CH$_2$CH$_2$N$_3$ | CH$_2$OH | OCH$_3$ | |
| J-1 | — | H | H | CH$_2$CH$_2$N$_3$ | CH$_2$CN | OCH$_3$ | |
| J-1 | — | H | H | CH$_2$CH$_2$N$_3$ | CH$_2$CO$_2$CH$_3$ | OCH$_3$ | |
| J-1 | — | H | H | CH$_2$CH$_2$N$_3$ | OCH$_3$ | CN | |
| J-1 | — | H | H | CH$_2$CH$_2$N$_3$ | OCH$_3$ | N$_3$ | |
| J-1 | — | H | H | CH$_2$CH$_2$N$_3$ | OCH$_3$ | CHO | |
| J-1 | — | H | H | CH$_2$CH$_2$N$_3$ | OCH$_3$ | C(O)CH$_3$ | |
| J-1 | — | H | H | CH$_2$CH$_2$N$_3$ | CH$_3$ | SCH$_3$ | |
| J-1 | — | H | H | CH$_2$CH$_2$N$_3$ | OCH$_3$ | SC$_2$H$_5$ | |
| J-1 | — | H | H | CH$_2$CH$_2$N$_3$ | SCH$_3$ | SCH$_3$ | |
| J-1 | — | H | H | CH$_2$CH$_2$N$_3$ | CH$_3$ | CH$_2$SCH$_3$ | |
| J-1 | — | H | H | CH$_2$CH$_2$N$_3$ | OCH$_3$ | CH$_2$SC$_2$H$_5$ | |
| J-1 | — | H | H | CH$_2$CH$_2$N$_3$ | OCH$_3$ | NHCH$_3$ | |
| J-1 | — | H | H | CH$_2$CH$_2$N$_3$ | OCH$_3$ | N(CH$_3$)$_2$ | |
| J-1 | — | H | H | CH$_2$CH$_2$N$_3$ | OCH$_3$ | N(OCH$_3$)CH$_3$ | |
| J-1 | — | H | H | CH$_2$CH$_2$N$_3$ | OCH$_3$ | C≡CH | |
| J-1 | — | H | H | CH$_2$CH$_2$N$_3$ | OCH$_3$ | C≡CCH$_3$ | |
| J-1 | — | H | H | CH$_2$CH$_2$N$_3$ | OCH$_3$ | CH$_2$C≡CH | |
| J-1 | — | H | H | CH$_2$CH$_2$N$_3$ | CH$_3$ | OCH$_2$C≡CH | |
| J-1 | — | H | H | CH$_2$CH$_2$N$_3$ | CH$_3$ | OCH$_2$CH=CH$_2$ | |
| J-1 | — | H | H | CH$_2$CH$_2$N$_3$ | CH$_3$ | OCH$_2$OCH$_3$ | |
| J-1 | — | H | H | CH$_2$CH$_2$N$_3$ | CH$_3$ | OCH$_2$CH$_2$OCH$_3$ | |
| J-1 | — | H | H | CH$_2$CH$_2$N$_3$ | OCH$_3$ | SCF$_2$H | |
| J-1 | — | H | H | CH$_2$CH$_2$N$_3$ | cyclopropyl | OCH$_3$ | |
| J-1 | — | H | H | CH$_2$CH$_2$N$_3$ | cyclopropyl | CH$_3$ | |
| J-1 | CH$_2$ | H | H | CH$_2$CH$_2$N$_3$ | OCH$_3$ | OCH$_3$ | |
| J-1 | CH$_2$ | H | H | CH$_2$CH$_2$N$_3$ | OCH$_3$ | CH$_3$ | |
| J-1 | CH$_2$ | H | H | CH$_2$CH$_2$N$_3$ | CH$_3$ | CH$_3$ | |
| J-1 | — | CH$_3$ | H | CH$_2$CH$_2$N$_3$ | OCH$_3$ | OCH$_3$ | |
| J-1 | — | CH$_3$ | H | CH$_2$CH$_2$N$_3$ | OCH$_3$ | CH$_3$ | |
| J-1 | — | CH$_3$ | H | CH$_2$CH$_2$N$_3$ | CH$_3$ | CH$_3$ | |
| J-1 | — | H | 5-Cl | CH$_2$CH$_2$N$_3$ | OCH$_3$ | OCH$_3$ | |
| J-1 | — | H | 5-Cl | CH$_2$CH$_2$N$_3$ | OCH$_3$ | CH$_3$ | |
| J-1 | — | H | 5-Cl | CH$_2$CH$_2$N$_3$ | CH$_3$ | CH$_3$ | |
| J-1 | — | H | 5-Cl | CH$_2$CH$_2$N$_3$ | Cl | OCH$_3$ | |
| J-1 | — | H | 5-OCH$_3$ | CH$_2$CH$_2$N$_3$ | OCH$_3$ | OCH$_3$ | |
| J-1 | — | H | 5-OCH$_3$ | CH$_2$CH$_2$N$_3$ | OCH$_3$ | CH$_3$ | |
| J-1 | — | H | 5-OCH$_3$ | CH$_2$CH$_2$N$_3$ | CH$_3$ | CH$_3$ | |
| J-1 | — | H | 5-OCH$_3$ | CH$_2$CH$_2$N$_3$ | Cl | OCH$_3$ | |
| J-1 | — | H | 5-OC$_2$H$_5$ | CH$_2$CH$_2$N$_3$ | OCH$_3$ | OCH$_3$ | |
| J-1 | — | H | 5-F | CH$_2$CH$_2$N$_3$ | OCH$_3$ | OCH$_3$ | |
| J-1 | — | H | 5-CH$_3$ | CH$_2$CH$_2$N$_3$ | OCH$_3$ | OCH$_3$ | |
| J-1 | — | H | 5-SCH$_3$ | CH$_2$CH$_2$N$_3$ | OCH$_3$ | OCH$_3$ | |
| J-1 | — | H | 5-N(CH$_3$)$_2$ | CH$_2$CH$_2$N$_3$ | OCH$_3$ | OCH$_3$ | |
| J-1 | — | H | 5-OCH$_2$CF$_3$ | CH$_2$CH$_2$N$_3$ | OCH$_3$ | OCH$_3$ | |
| J-1 | — | H | 5-OCH$_3$CF$_3$ | CH$_2$CH$_2$N$_3$ | OCH$_3$ | CH$_3$ | |
| J-1 | — | H | 5-NO$_2$ | CH$_2$CH$_2$N$_3$ | OCH$_3$ | OCH$_3$ | |
| J-1 | — | H | 5-Br | CH$_2$CH$_2$N$_3$ | OCH$_3$ | OCH$_3$ | |
| J-1 | — | H | 5-CN | CH$_2$CH$_2$N$_3$ | OCH$_3$ | OCH$_3$ | |
| J-1 | — | H | 3-Cl | CH$_2$CH$_2$N$_3$ | OCH$_3$ | OCH$_3$ | |
| J-1 | — | H | 3-F | CH$_2$CH$_2$N$_3$ | OCH$_3$ | OCH$_3$ | |
| J-1 | — | H | 3-Br | CH$_2$CH$_2$N$_3$ | OCH$_3$ | OCH$_3$ | |
| J-1 | — | H | 3-CH$_3$ | CH$_2$CH$_2$N$_3$ | OCH$_3$ | OCH$_3$ | |
| J-1 | — | H | 3-OCH$_3$ | CH$_2$CH$_2$N$_3$ | OCH$_3$ | OCH$_3$ | |
| J-1 | — | H | 3-NO$_2$ | CH$_2$CH$_2$N$_3$ | OCH$_3$ | OCH$_3$ | |
| J-1 | — | H | 6-Cl | CH$_2$CH$_2$N$_3$ | OCH$_3$ | OCH$_3$ | |
| J-1 | — | H | 6-F | CH$_2$CH$_2$N$_3$ | OCH$_3$ | OCH$_3$ | |
| J-1 | — | H | 6-Br | CH$_2$CH$_2$N$_3$ | OCH$_3$ | OCH$_3$ | |
| J-1 | — | H | 6-CH$_3$ | CH$_2$CH$_2$N$_3$ | OCH$_3$ | OCH$_3$ | |
| J-1 | — | H | 6-OCH$_3$ | CH$_2$CH$_2$N$_3$ | OCH$_3$ | OCH$_3$ | |
| J-1 | — | H | 6-NO$_2$ | CH$_2$CH$_2$N$_3$ | OCH$_3$ | OCH$_3$ | |
| J-1 | — | H | H | CH(CH$_3$)CH$_2$N$_3$ | OCH$_3$ | OCH$_3$ | |
| J-1 | — | H | H | CH(CH$_3$)CH$_2$N$_3$ | OCH$_3$ | CH$_3$ | |
| J-1 | — | H | H | CH(CH$_3$)CH$_2$N$_3$ | CH$_3$ | CH$_3$ | |
| J-1 | — | H | H | CH(CH$_3$)CH$_2$N$_3$ | Cl | OCH$_3$ | |
| J-1 | — | H | H | CH$_2$CH(CH$_3$)N$_3$ | OCH$_3$ | OCH$_3$ | |
| J-1 | — | H | H | CH$_2$CH(CH$_3$)N$_3$ | OCH$_3$ | CH$_3$ | |
| J-1 | — | H | H | CH$_2$CH(CH$_3$)N$_3$ | CH$_3$ | CH$_3$ | |
| J-1 | — | H | H | CH$_2$CH(CH$_3$)N$_3$ | Cl | OCH$_3$ | |
| J-1 | — | H | H | (CH$_2$)$_3$N$_3$ | OCH$_3$ | OCH$_3$ | |
| J-1 | — | H | H | (CH$_2$)$_3$N$_3$ | OCH$_3$ | CH$_3$ | |
| J-1 | — | H | H | (CH$_2$)$_3$N$_3$ | CH$_3$ | CH$_3$ | |
| J-1 | — | H | H | (CH$_2$)$_3$N$_3$ | Cl | OCH$_3$ | |
| J-1 | — | H | H | CH(CH$_3$)CH$_2$CH$_2$N$_3$ | OCH$_3$ | OCH$_3$ | |
| J-1 | — | H | H | CH(CH$_3$)CH$_2$CH$_2$N$_3$ | OCH$_3$ | CH$_3$ | |
| J-1 | — | H | H | CH(CH$_3$)CH$_2$CH$_2$N$_3$ | CH$_3$ | CH$_3$ | |
| J-1 | — | H | H | CH(CH$_3$)CH$_2$CH$_2$N$_3$ | Cl | OCH$_3$ | |
| J-1 | — | H | H | CH$_2$CH(CH$_3$)CH$_2$N$_3$ | OCH$_3$ | OCH$_3$ | |

TABLE 1-continued

GENERAL FORMULA 1

| J | E | R | R¹/R² | Q | X | Y | m.p. °C. |
|---|---|---|---|---|---|---|---|
| J-1 | — | H | H | $CH_2CH(CH_3)CH_2N_3$ | $OCH_3$ | $CH_3$ | |
| J-1 | — | H | H | $CH_2CH(CH_3)CH_2N_3$ | $CH_3$ | $CH_3$ | |
| J-1 | — | H | H | $CH_2CH(CH_3)CH_2N_3$ | Cl | $OCH_3$ | |
| J-1 | — | H | H | $(CH_2)_2CH(CH_3)N_3$ | $OCH_3$ | $OCH_3$ | |
| J-1 | — | H | H | $(CH_2)_2CH(CH_3)N_3$ | $OCH_3$ | $CH_3$ | |
| J-1 | — | H | H | $(CH_2)_2CH(CH_3)N_3$ | $CH_3$ | $CH_3$ | |
| J-1 | — | H | H | $(CH_2)_2CH(CH_3)N_3$ | Cl | $OCH_3$ | |
| J-1 | — | H | H | $CH_2CH_2SCN$ | $OCH_3$ | $OCH_3$ | 124–127 |
| J-1 | — | H | H | $CH_2CH_2SCN$ | $OCH_3$ | $CH_3$ | 117–124 |
| J-1 | — | H | H | $CH_2CH_2SCN$ | $CH_3$ | $CH_3$ | |
| J-1 | — | H | H | $CH_2CH_2SCN$ | Cl | $OCH_3$ | 115–119 |
| J-1 | $CH_2$ | H | H | $CH_2CH_2SCN$ | $OCH_3$ | $OCH_3$ | |
| J-1 | — | $CH_3$ | H | $CH_2CH_2SCN$ | $OCH_3$ | $OCH_3$ | |
| J-1 | — | H | 5-Cl | $CH_2CH_2SCN$ | $OCH_3$ | $OCH_3$ | |
| J-1 | — | H | 5-Cl | $CH_2CH_2SCN$ | $OCH_3$ | $CH_3$ | |
| J-1 | — | H | 5-$OCH_3$ | $CH_2CH_2SCN$ | $OCH_3$ | $OCH_3$ | |
| J-1 | — | H | 5-$OCH_3$ | $CH_2CH_2SCN$ | $OCH_3$ | $CH_3$ | |
| J-1 | — | H | 5-$CH_3$ | $CH_2CH_2SCN$ | $OCH_3$ | $OCH_3$ | |
| J-1 | — | H | 5-$OCH_2CF_3$ | $CH_2CH_2SCN$ | $OCH_3$ | $OCH_3$ | |
| J-1 | — | H | 3-Cl | $CH_2CH_2SCN$ | $OCH_3$ | $OCH_3$ | |
| J-1 | — | H | 3-$CH_3$ | $CH_2CH_2SCN$ | $OCH_3$ | $OCH_3$ | |
| J-1 | — | H | 6-Cl | $CH_2CH_2SCN$ | $OCH_3$ | $OCH_3$ | |
| J-1 | — | H | 6-$CH_3$ | $CH_2CH_2SCN$ | $OCH_3$ | $OCH_3$ | |
| J-1 | — | H | H | $CH(CH_3)CH_2SCN$ | $OCH_3$ | $OCH_3$ | |
| J-1 | — | H | H | $CH(CH_3)CH_2SCN$ | $OCH_3$ | $CH_3$ | |
| J-1 | — | H | H | $CH(CH_3)CH_2SCN$ | $CH_3$ | $CH_3$ | |
| J-1 | — | H | H | $CH(CH_3)CH_2SCN$ | Cl | $OCH_3$ | |
| J-1 | — | H | H | $CH_2CH(CH_3)SCN$ | $OCH_3$ | $OCH_3$ | |
| J-1 | — | H | H | $CH_2CH(CH_3)SCN$ | $OCH_3$ | $CH_3$ | |
| J-1 | — | H | H | $CH_2CH(CH_3)SCN$ | $CH_3$ | $CH_3$ | |
| J-1 | — | H | H | $CH_2CH(CH_3)SCN$ | Cl | $OCH_3$ | |
| J-1 | — | H | H | $(CH_2)_3SCN$ | $OCH_3$ | $OCH_3$ | |
| J-1 | — | H | H | $(CH_2)_3SCN$ | $OCH_3$ | $CH_3$ | |
| J-1 | — | H | H | $(CH_2)_3SCN$ | $CH_3$ | $CH_3$ | |
| J-1 | — | H | H | $(CH_2)_3SCN$ | Cl | $OCH_3$ | |
| J-1 | — | H | H | $CH(CH_3)CH_2CH_2SCN$ | $OCH_3$ | $OCH_3$ | |
| J-1 | — | H | H | $CH(CH_3)CH_2CH_2SCN$ | $OCH_3$ | $CH_3$ | |
| J-1 | — | H | H | $CH(CH_3)CH_2CH_2SCN$ | $CH_3$ | $CH_3$ | |
| J-1 | — | H | H | $CH(CH_3)CH_2CH_2SCN$ | Cl | $OCH_3$ | |
| J-1 | — | H | H | $CH_2CH(CH_3)CH_2SCN$ | $OCH_3$ | $OCH_3$ | |
| J-1 | — | H | H | $CH_2CH(CH_3)CH_2SCN$ | $OCH_3$ | $CH_3$ | |
| J-1 | — | H | H | $CH_2CH(CH_3)CH_2SCN$ | $CH_3$ | $CH_3$ | |
| J-1 | — | H | H | $CH_2CH(CH_3)CH_2SCN$ | Cl | $OCH_3$ | |
| J-1 | — | H | H | $(CH_2)_2CH(CH_3)SCN$ | $OCH_3$ | $OCH_3$ | |
| J-1 | — | H | H | $(CH_2)_2CH(CH_3)SCN$ | $OCH_3$ | $CH_3$ | |
| J-1 | — | H | H | $(CH_2)_2CH(CH_3)SCN$ | $CH_3$ | $CH_3$ | |
| J-1 | — | H | H | $(CH_2)_2CH(CH_3)SCN$ | Cl | $OCH_3$ | |
| J-1 | — | H | H | $CH_2CH_2NO_2$ | $OCH_3$ | $OCH_3$ | |
| J-1 | — | H | H | $CH_2CH_2NO_2$ | $OCH_3$ | $CH_3$ | |
| J-1 | — | H | H | $CH_2CH_2NO_2$ | $CH_3$ | $CH_3$ | |
| J-1 | — | H | H | $CH_2CH_2NO_2$ | Cl | $OCH_3$ | |
| J-1 | $CH_2$ | H | H | $CH_2CH_2NO_2$ | $OCH_3$ | $OCH_3$ | |
| J-1 | — | $CH_3$ | H | $CH_2CH_2NO_2$ | $OCH_3$ | $OCH_3$ | |
| J-1 | — | H | 5-Cl | $CH_2CH_2NO_2$ | $OCH_3$ | $OCH_3$ | |
| J-1 | — | H | 5-Cl | $CH_2CH_2NO_2$ | $OCH_3$ | $CH_3$ | |
| J-1 | — | H | 5-$OCH_3$ | $CH_2CH_2NO_2$ | $OCH_3$ | $OCH_3$ | |
| J-1 | — | H | 5-$OCH_3$ | $CH_2CH_2NO_2$ | $OCH_3$ | $CH_3$ | |
| J-1 | — | H | 5-$CH_3$ | $CH_2CH_2NO_2$ | $OCH_3$ | $OCH_3$ | |
| J-1 | — | H | 5-$OCH_2CF_3$ | $CH_2CH_2NO_2$ | $OCH_3$ | $OCH_3$ | |
| J-1 | — | H | 3-Cl | $CH_2CH_2NO_2$ | $OCH_3$ | $OCH_3$ | |
| J-1 | — | H | 3-$CH_3$ | $CH_2CH_2NO_2$ | $OCH_3$ | $OCH_3$ | |
| J-1 | — | H | 6-Cl | $CH_2CH_2NO_2$ | $OCH_3$ | $OCH_3$ | |
| J-1 | — | H | 6-$CH_3$ | $CH_2CH_2NO_2$ | $OCH_3$ | $OCH_3$ | |
| J-1 | — | H | H | $CH(CH_3)CH_2NO_2$ | $OCH_3$ | $OCH_3$ | |
| J-1 | — | H | H | $CH(CH_3)CH_2NO_2$ | $OCH_3$ | $CH_3$ | |
| J-1 | — | H | H | $CH(CH_3)CH_2NO_2$ | $CH_3$ | $CH_3$ | |
| J-1 | — | H | H | $CH(CH_3)CH_2NO_2$ | Cl | $OCH_3$ | |
| J-1 | — | H | H | $CH_2CH(CH_3)NO_2$ | $OCH_3$ | $OCH_3$ | |
| J-1 | — | H | H | $CH_2CH(CH_3)NO_2$ | $OCH_3$ | $CH_3$ | |
| J-1 | — | H | H | $CH_2CH(CH_3)NO_2$ | $CH_3$ | $CH_3$ | |
| J-1 | — | H | H | $CH_2CH(CH_3)NO_2$ | Cl | $OCH_3$ | |
| J-1 | — | H | H | $(CH_2)_3NO_2$ | $OCH_3$ | $OCH_3$ | |
| J-1 | — | H | H | $(CH_2)_3NO_2$ | $OCH_3$ | $CH_3$ | |
| J-1 | — | H | H | $(CH_2)_3NO_2$ | $CH_3$ | $CH_3$ | |
| J-1 | — | H | H | $(CH_2)_3NO_2$ | Cl | $OCH_3$ | |
| J-1 | — | H | H | $CH(CH_3)CH_2CH_2NO_2$ | $OCH_3$ | $OCH_3$ | |
| J-1 | — | H | H | $CH(CH_3)CH_2CH_2NO_2$ | $OCH_3$ | $CH_3$ | |
| J-1 | — | H | H | $CH(CH_3)CH_2CH_2NO_2$ | $CH_3$ | $CH_3$ | |
| J-1 | — | H | H | $CH(CH_3)CH_2CH_2NO_2$ | Cl | $OCH_3$ | |
| J-1 | — | H | H | $CH_2CH(CH_3)CH_2NO_2$ | $OCH_3$ | $OCH_3$ | |

TABLE 1-continued

GENERAL FORMULA 1

| J | E | R | $R^1/R^2$ | Q | X | Y | m.p. °C. |
|---|---|---|---|---|---|---|---|
| J-1 | — | H | H | $CH_2CH(CH_3)CH_2NO_2$ | $OCH_3$ | $CH_3$ | |
| J-1 | — | H | H | $CH_2CH(CH_3)CH_2NO_2$ | $CH_3$ | $CH_3$ | |
| J-1 | — | H | H | $CH_2CH(CH_3)CH_2NO_2$ | Cl | $OCH_3$ | |
| J-1 | — | H | H | $(CH_2)_2CH(CH_3)NO_2$ | $OCH_3$ | $OCH_3$ | |
| J-1 | — | H | H | $(CH_2)_2CH(CH_3)NO_2$ | $OCH_3$ | $CH_3$ | |
| J-1 | — | H | H | $(CH_2)_2CH(CH_3)NO_2$ | $CH_3$ | $CH_3$ | |
| J-1 | — | H | H | $(CH_2)_2CH(CH_3)NO_2$ | Cl | $OCH_3$ | |
| J-2 | — | H | H | $CH_2CH_2N_3$ | $OCH_3$ | $OCH_3$ | |
| J-2 | — | H | H | $CH_2CH_2N_3$ | $OCH_3$ | $CH_3$ | |
| J-2 | — | H | H | $CH_2CH_2N_3$ | $CH_3$ | $CH_3$ | |
| J-2 | — | H | H | $CH_2CH_2N_3$ | Cl | $OCH_3$ | |
| J-2 | — | H | H | $CH_2CH_2N_3$ | $OCH_3$ | $CH(OCH_3)_2$ | |
| J-2 | — | H | 4-$CH_3$ | $CH_2CH_2N_3$ | $OCH_3$ | $OCH_3$ | |
| J-2 | — | H | 4-Cl | $CH_2CH_2N_3$ | $OCH_3$ | $OCH_3$ | |
| J-2 | — | H | 4-F | $CH_2CH_2N_3$ | $OCH_3$ | $OCH_3$ | |
| J-2 | — | H | 4-Br | $CH_2CH_2N_3$ | $OCH_3$ | $OCH_3$ | |
| J-2 | — | H | 4-$OCH_3$ | $CH_2CH_2N_3$ | $OCH_3$ | $OCH_3$ | |
| J-2 | — | H | 5-$CH_3$ | $CH_2CH_2N_3$ | $OCH_3$ | $OCH_3$ | |
| J-2 | — | H | 5-Cl | $CH_2CH_2N_3$ | $OCH_3$ | $OCH_3$ | |
| J-2 | — | H | 5-F | $CH_2CH_2N_3$ | $OCH_3$ | $OCH_3$ | |
| J-2 | — | H | 5-Br | $CH_2CH_2N_3$ | $OCH_3$ | $OCH_3$ | |
| J-2 | — | H | 5-$OCH_3$ | $CH_2CH_2N_3$ | $OCH_3$ | $OCH_3$ | |
| J-2 | — | H | H | $(CH_2)_3N_3$ | $OCH_3$ | $OCH_3$ | |
| J-2 | — | H | H | $(CH_2)_3N_3$ | $OCH_3$ | $CH_3$ | |
| J-2 | — | H | H | $CH_2CH_2SCN$ | $OCH_3$ | $OCH_3$ | |
| J-2 | — | H | H | $CH_2CH_2SCN$ | $OCH_3$ | $CH_3$ | |
| J-2 | — | H | H | $CH_2CH_2SCN$ | $CH_3$ | $CH_3$ | |
| J-2 | — | H | H | $CH_2CH_2SCN$ | Cl | $OCH_3$ | |
| J-2 | — | H | H | $(CH_2)_3SCN$ | $OCH_3$ | $OCH_3$ | |
| J-2 | — | H | H | $(CH_2)_3SCN$ | $OCH_3$ | $CH_3$ | |
| J-2 | — | H | H | $CH_2CH_2NO_2$ | $OCH_3$ | $OCH_3$ | |
| J-2 | — | H | H | $CH_2CH_2NO_2$ | $OCH_3$ | $CH_3$ | |
| J-2 | — | H | H | $CH_2CH_2NO_2$ | $CH_3$ | $CH_3$ | |
| J-2 | — | H | H | $CH_2CH_2NO_2$ | Cl | $OCH_3$ | |
| J-2 | — | H | H | $(CH_2)_3NO_2$ | $OCH_3$ | $OCH_3$ | |
| J-2 | — | H | H | $(CH_2)_3NO_2$ | $OCH_3$ | $CH_3$ | |
| J-2 | $CH_2$ | H | H | $CH_2CH_2N_3$ | $OCH_3$ | $OCH_3$ | |
| J-2 | — | $CH_3$ | H | $CH_2CH_2N_3$ | $OCH_3$ | $OCH_3$ | |
| J-3 | | H | H | $CH_2CH_2N_3$ | $OCH_3$ | $OCH_3$ | |
| J-3 | | H | H | $CH_2CH_2N_3$ | $OCH_3$ | $CH_3$ | |
| J-3 | | H | H | $CH_2CH_2N_3$ | $CH_3$ | $CH_3$ | |
| J-3 | | H | H | $CH_2CH_2N_3$ | Cl | $OCH_3$ | |
| J-3 | | H | H | $CH_2CH_2N_3$ | $OCH_3$ | $CH(OCH_3)_2$ | |
| J-3 | | H | $CH_3$ | $CH_2CH_2N_3$ | $OCH_3$ | $OCH_3$ | |
| J-3 | | H | Cl | $CH_2CH_2N_3$ | $OCH_3$ | $OCH_3$ | |
| J-3 | | H | F | $CH_2CH_2N_3$ | $OCH_3$ | $OCH_3$ | |
| J-3 | | H | Br | $CH_2CH_2N_3$ | $OCH_3$ | $OCH_3$ | |
| J-3 | | H | $OCH_3$ | $CH_2CH_2N_3$ | $OCH_3$ | $OCH_3$ | |
| J-3 | | H | $SCH_3$ | $CH_2CH_2N_3$ | $OCH_3$ | $OCH_3$ | |
| J-3 | | H | $SO_2CH_3$ | $CH_2CH_2N_3$ | $OCH_3$ | $OCH_3$ | |
| J-3 | | H | H | $(CH_2)_3N_3$ | $OCH_3$ | $OCH_3$ | |
| J-3 | | H | H | $(CH_2)_3N_3$ | $OCH_3$ | $CH_3$ | |
| J-3 | | H | H | $CH_2CH_2SCN$ | $OCH_3$ | $OCH_3$ | |
| J-3 | | H | H | $CH_2CH_2SCN$ | $OCH_3$ | $CH_3$ | |
| J-3 | | H | H | $CH_2CH_2SCN$ | $CH_3$ | $CH_3$ | |
| J-3 | | H | H | $CH_2CH_2SCN$ | Cl | $OCH_3$ | |
| J-3 | | H | H | $(CH_2)_3SCN$ | $OCH_3$ | $OCH_3$ | |
| J-3 | | H | H | $(CH_2)_3SCN$ | $OCH_3$ | $CH_3$ | |
| J-3 | | H | H | $CH_2CH_2NO_2$ | $OCH_3$ | $OCH_3$ | |
| J-3 | | H | H | $CH_2CH_2NO_2$ | $OCH_3$ | $CH_3$ | |
| J-3 | | H | H | $CH_2CH_2NO_2$ | $CH_3$ | $CH_3$ | |
| J-3 | | H | H | $CH_2CH_2NO_2$ | Cl | $OCH_3$ | |
| J-3 | | H | H | $(CH_2)_3NO_2$ | $OCH_3$ | $OCH_3$ | |
| J-3 | | H | H | $(CH_2)_3NO_2$ | $OCH_3$ | $CH_3$ | |
| J-3 | | $CH_3$ | H | $CH_2CH_2N_3$ | $OCH_3$ | $OCH_3$ | |
| J-4 | | H | H | $CH_2CH_2N_3$ | $OCH_3$ | $OCH_3$ | |
| J-4 | | H | H | $CH_2CH_2N_3$ | $OCH_3$ | $CH_3$ | |
| J-4 | | H | H | $CH_2CH_2N_3$ | $CH_3$ | $CH_3$ | |
| J-4 | | H | H | $CH_2CH_2N_3$ | Cl | $OCH_3$ | |
| J-4 | | H | H | $CH_2CH_2N_3$ | $OCH_3$ | $CH(OCH_3)_2$ | |
| J-4 | | H | $CH_3$ | $CH_2CH_2N_3$ | $OCH_3$ | $OCH_3$ | |
| J-4 | | H | Cl | $CH_2CH_2N_3$ | $OCH_3$ | $OCH_3$ | |
| J-4 | | H | F | $CH_2CH_2N_3$ | $OCH_3$ | $OCH_3$ | |
| J-4 | | H | Br | $CH_2CH_2N_3$ | $OCH_3$ | $OCH_3$ | |
| J-4 | | H | $OCH_3$ | $CH_2CH_2N_3$ | $OCH_3$ | $OCH_3$ | |
| J-4 | | H | $SCH_3$ | $CH_2CH_2N_3$ | $OCH_3$ | $OCH_3$ | |
| J-4 | | H | $SO_2CH_3$ | $CH_2CH_2N_3$ | $OCH_3$ | $OCH_3$ | |
| J-4 | | H | H | $(CH_2)_3N_3$ | $OCH_3$ | $OCH_3$ | |
| J-4 | | H | H | $(CH_2)_3N_3$ | $OCH_3$ | $CH_3$ | |
| J-4 | | H | H | $CH_2CH_2SCN$ | $OCH_3$ | $OCH_3$ | |

TABLE 1-continued

GENERAL FORMULA 1

| J | E | R | R$^1$/R$^2$ | Q | X | Y | m.p. °C. |
|---|---|---|---|---|---|---|---|
| J-4 | | H | H | CH$_2$CH$_2$SCN | OCH$_3$ | CH$_3$ | |
| J-4 | | H | H | CH$_2$CH$_2$SCN | CH$_3$ | CH$_3$ | |
| J-4 | | H | H | CH$_2$CH$_2$SCN | Cl | OCH$_3$ | |
| J-4 | | H | H | (CH$_2$)$_3$SCN | OCH$_3$ | OCH$_3$ | |
| J-4 | | H | H | (CH$_2$)$_3$SCN | OCH$_3$ | CH$_3$ | |
| J-4 | | H | H | CH$_2$CH$_2$NO$_2$ | OCH$_3$ | OCH$_3$ | |
| J-4 | | H | H | CH$_2$CH$_2$NO$_2$ | OCH$_3$ | CH$_3$ | |
| J-4 | | H | H | CH$_2$CH$_2$NO$_2$ | CH$_3$ | CH$_3$ | |
| J-4 | | H | H | CH$_2$CH$_2$NO$_2$ | Cl | OCH$_3$ | |
| J-4 | | H | H | (CH$_2$)$_3$NO$_2$ | OCH$_3$ | OCH$_3$ | |
| J-4 | | H | H | (CH$_2$)$_3$NO$_2$ | OCH$_3$ | CH$_3$ | |
| J-4 | | CH$_3$ | H | CH$_2$CH$_2$N$_3$ | OCH$_3$ | OCH$_3$ | |
| J-5 | | H | H | CH$_2$CH$_2$N$_3$ | OCH$_3$ | OCH$_3$ | |
| J-5 | | H | H | CH$_2$CH$_2$N$_3$ | OCH$_3$ | CH$_3$ | |
| J-5 | | H | H | CH$_2$CH$_2$N$_3$ | CH$_3$ | CH$_3$ | |
| J-5 | | H | H | CH$_2$CH$_2$N$_3$ | Cl | OCH$_3$ | |
| J-5 | | H | H | CH$_2$CH$_2$N$_3$ | OCH$_3$ | CH(OCH$_3$)$_2$ | |
| J-5 | | H | H | CH$_2$CH$_2$SCN | OCH$_3$ | OCH$_3$ | |
| J-5 | | H | H | CH$_2$CH$_2$SCN | OCH$_3$ | CH$_3$ | |
| J-5 | | H | H | CH$_2$CH$_2$SCN | CH$_3$ | CH$_3$ | |
| J-5 | | H | H | CH$_2$CH$_2$SCN | Cl | OCH$_3$ | |
| J-5 | | H | H | CH$_2$CH$_2$NO$_2$ | OCH$_3$ | OCH$_3$ | |
| J-5 | | H | H | CH$_2$CH$_2$NO$_2$ | OCH$_3$ | CH$_3$ | |
| J-5 | | H | H | CH$_2$CH$_2$NO$_2$ | CH$_3$ | CH$_3$ | |
| J-5 | | H | H | CH$_2$CH$_2$NO$_2$ | Cl | OCH$_3$ | |
| J-6(n = 0) | — | H | H | CH$_2$CH$_2$N$_3$ | OCH$_3$ | OCH$_3$ | |
| J-6(n = 0) | — | H | H | CH$_2$CH$_2$N$_3$ | OCH$_3$ | CH$_3$ | |
| J-6(n = 0) | — | H | H | CH$_2$CH$_2$N$_3$ | CH$_3$ | CH$_3$ | |
| J-6(n = 0) | — | H | H | CH$_2$CH$_2$N$_3$ | Cl | OCH$_3$ | |
| J-6(n = 0) | — | H | H | CH$_2$CH$_2$N$_3$ | Br | OCH$_3$ | |
| J-6(n = 0) | — | H | H | CH$_2$CH$_2$N$_3$ | OCH$_3$ | OCF$_2$H | |
| J-6(n = 0) | — | H | H | CH$_2$CH$_2$N$_3$ | OCH$_3$ | CH(OCH$_3$)$_2$ | |
| J-6(n = 0) | — | H | 5-CH$_3$ | CH$_2$CH$_2$N$_3$ | OCH$_3$ | OCH$_3$ | |
| J-6(n = 0) | — | H | 5-OCH$_3$ | CH$_2$CH$_2$N$_3$ | OCH$_3$ | OCH$_3$ | |
| J-6(n = 0) | — | H | 5-Cl | CH$_2$CH$_2$N$_3$ | OCH$_3$ | OCH$_3$ | |
| J-6(n = 0) | — | H | 5-CF$_3$ | CH$_2$CH$_2$N$_3$ | OCH$_3$ | OCH$_3$ | |
| J-6(n = 0) | — | H | 4-CH$_3$ | CH$_2$CH$_2$N$_3$ | OCH$_3$ | OCH$_3$ | |
| J-6(n = 0) | — | H | 4-OCH$_3$ | CH$_2$CH$_2$N$_3$ | OCH$_3$ | OCH$_3$ | |
| J-6(n = 0) | — | H | 4-Cl | CH$_2$CH$_2$N$_3$ | OCH$_3$ | OCH$_3$ | |
| J-6(n = 0) | — | H | 4-CF$_3$ | CH$_2$CH$_2$N$_3$ | OCH$_3$ | OCH$_3$ | |
| J-6(n = 0) | — | H | 6-CH$_3$ | CH$_2$CH$_2$N$_3$ | OCH$_3$ | OCH$_3$ | |
| J-6(n = 0) | — | H | 6-OCH$_3$ | CH$_2$CH$_2$N$_3$ | OCH$_3$ | OCH$_3$ | |
| J-6(n = 0) | — | H | 6-Cl | CH$_2$CH$_2$N$_3$ | OCH$_3$ | OCH$_3$ | |
| J-6(n = 0) | — | H | 6-CF$_3$ | CH$_2$CH$_2$N$_3$ | OCH$_3$ | OCH$_3$ | |
| J-6(n = 0) | — | H | H | (CH$_2$)$_3$N$_3$ | OCH$_3$ | OCH$_3$ | |
| J-6(n = 0) | — | H | H | (CH$_2$)$_3$N$_3$ | OCH$_3$ | CH$_3$ | |
| J-6(n = 0) | — | H | H | CH(CH$_3$)CH$_2$N$_3$ | OCH$_3$ | OCH$_3$ | |
| J-6(n = 0) | — | H | H | CH(CH$_3$)CH$_2$N$_3$ | OCH$_3$ | CH$_3$ | |
| J-6(n = 0) | — | H | H | CH$_2$CH$_2$SCN | OCH$_3$ | OCH$_3$ | |
| J-6(n = 0) | — | H | H | CH$_2$CH$_2$SCN | OCH$_3$ | CH$_3$ | |
| J-6(n = 0) | — | H | H | CH$_2$CH$_2$SCN | CH$_3$ | CH$_3$ | |
| J-6(n = 0) | — | H | H | CH$_2$CH$_2$SCN | Cl | OCH$_3$ | |
| J-6(n = 0) | — | H | H | (CH$_2$)$_3$SCN | OCH$_3$ | OCH$_3$ | |
| J-6(n = 0) | — | H | H | (CH$_2$)$_3$SCN | OCH$_3$ | CH$_3$ | |
| J-6(n = 0) | — | H | H | CH(CH$_3$)CH$_2$SCN | OCH$_3$ | OCH$_3$ | |
| J-6(n = 0) | — | H | H | CH(CH$_3$)CH$_2$SCN | OCH$_3$ | CH$_3$ | |
| J-6(n = 0) | — | H | H | CH$_2$CH$_2$NO$_2$ | OCH$_3$ | OCH$_3$ | |
| J-6(n = 0) | — | H | H | CH$_2$CH$_2$NO$_2$ | OCH$_3$ | CH$_3$ | |
| J-6(n = 0) | — | H | H | CH$_2$CH$_2$NO$_2$ | CH$_3$ | CH$_3$ | |
| J-6(n = 0) | — | H | H | CH$_2$CH$_2$NO$_2$ | Cl | OCH$_3$ | |
| J-6(n = 0) | — | H | H | (CH$_2$)$_3$NO$_2$ | OCH$_3$ | OCH$_3$ | |
| J-6(n = 0) | — | H | H | (CH$_2$)$_3$NO$_2$ | OCH$_3$ | CH$_3$ | |
| J-6(n = 0) | — | H | H | CH(CH$_3$)CH$_2$NO$_2$ | OCH$_3$ | OCH$_3$ | |
| J-6(n = 0) | — | H | H | CH(CH$_3$)CH$_2$NO$_2$ | OCH$_3$ | CH$_3$ | |
| J-6(n = 0) | CH$_2$ | H | H | CH$_2$CH$_2$N$_3$ | OCH$_3$ | OCH$_3$ | |
| J-6(n = 0) | CH$_2$ | H | H | CH$_2$CH$_2$SCN | OCH$_3$ | OCH$_3$ | |
| J-6(n = 0) | CH$_2$ | H | H | CH$_2$CH$_2$NO$_2$ | OCH$_3$ | OCH$_3$ | |
| J-6(n = 0) | — | CH$_3$ | H | CH$_2$CH$_2$N$_3$ | OCH$_3$ | OCH$_3$ | |
| J-6(n = 0) | — | CH$_3$ | H | CH$_2$CH$_2$SCN | OCH$_3$ | OCH$_3$ | |
| J-6(n = 0) | — | CH$_3$ | H | CH$_2$CH$_2$NO$_2$ | OCH$_3$ | OCH$_3$ | |
| J-6(n = 1) | — | H | H | CH$_2$CH$_2$N$_3$ | OCH$_3$ | OCH$_3$ | |
| J-6(n = 1) | — | H | H | CH$_2$CH$_2$SCN | OCH$_3$ | OCH$_3$ | |
| J-6(n = 1) | — | H | H | CH$_2$CH$_2$NO$_2$ | OCH$_3$ | OCH$_3$ | |
| J-7(n = 0) | — | H | H | CH$_2$CH$_2$N$_3$ | OCH$_3$ | OCH$_3$ | |
| J-7(n = 0) | — | H | H | CH$_2$CH$_2$N$_3$ | OCH$_3$ | CH$_3$ | |
| J-7(n = 0) | — | H | H | CH$_2$CH$_2$N$_3$ | CH$_3$ | CH$_3$ | |
| J-7(n = 0) | — | H | H | CH$_2$CH$_2$N$_3$ | Cl | OCH$_3$ | |
| J-7(n = 0) | — | H | 4-CH$_3$ | CH$_2$CH$_2$N$_3$ | OCH$_3$ | OCH$_3$ | |
| J-7(n = 0) | — | H | 4-Cl | CH$_2$CH$_2$N$_3$ | OCH$_3$ | OCH$_3$ | |
| J-7(n = 0) | — | H | 4-CF$_3$ | CH$_2$CH$_2$N$_3$ | OCH$_3$ | OCH$_3$ | |

TABLE 1-continued

GENERAL FORMULA 1

| J | E | R | R$^1$/R$^2$ | Q | X | Y | m.p. °C. |
|---|---|---|---|---|---|---|---|
| J-7(n = 0) | — | H | 4-OCH$_3$ | CH$_2$CH$_2$N$_3$ | OCH$_3$ | OCH$_3$ | |
| J-7(n = 0) | — | H | 4-SCH$_3$ | CH$_2$CH$_2$N$_3$ | OCH$_3$ | OCH$_3$ | |
| J-7(n = 0) | — | H | 4-SO$_2$CH$_3$ | CH$_2$CH$_2$N$_3$ | OCH$_3$ | OCH$_3$ | |
| J-7(n = 0) | — | H | 5-Cl | CH$_2$CH$_2$N$_3$ | OCH$_3$ | OCH$_3$ | |
| J-7(n = 0) | — | H | 6-OCH$_3$ | CH$_2$CH$_2$N$_3$ | OCH$_3$ | OCH$_3$ | |
| J-7(n = 0) | — | H | H | (CH$_2$)$_3$N$_3$ | OCH$_3$ | CH$_3$ | |
| J-7(n = 0) | — | H | H | CH$_2$CH$_2$SCN | OCH$_3$ | OCH$_3$ | |
| J-7(n = 0) | — | H | H | CH$_2$CH$_2$SCN | OCH$_3$ | CH$_3$ | |
| J-7(n = 0) | — | H | H | CH$_2$CH$_2$SCN | CH$_3$ | CH$_3$ | |
| J-7(n = 0) | — | H | H | CH$_2$CH$_2$SCN | Cl | OCH$_3$ | |
| J-7(n = 0) | — | H | H | (CH$_2$)$_3$SCN | OCH$_3$ | OCH$_3$ | |
| J-7(n = 0) | — | H | H | CH$_2$CH$_2$NO$_2$ | OCH$_3$ | OCH$_3$ | |
| J-7(n = 0) | — | H | H | CH$_2$CH$_2$NO$_2$ | OCH$_3$ | CH$_3$ | |
| J-7(n = 0) | — | H | H | CH$_2$CH$_2$NO$_2$ | CH$_3$ | CH$_3$ | |
| J-7(n = 0) | — | H | H | CH$_2$CH$_2$NO$_2$ | Cl | OCH$_3$ | |
| J-7(n = 0) | — | H | H | (CH$_2$)$_3$NO$_2$ | OCH$_3$ | OCH$_3$ | |
| J-7(n = 0) | CH$_2$ | H | H | CH$_2$CH$_2$N$_3$ | OCH$_3$ | OCH$_3$ | |
| J-7(n = 0) | CH$_2$ | H | H | CH$_2$CH$_2$SCN | OCH$_3$ | OCH$_3$ | |
| J-7(n = 0) | CH$_2$ | H | H | CH$_2$CH$_2$NO$_2$ | OCH$_3$ | OCH$_3$ | |
| J-7(n = 0) | — | CH$_3$ | H | CH$_2$CH$_2$N$_3$ | OCH$_3$ | OCH$_3$ | |
| J-7(n = 0) | — | CH$_3$ | H | CH$_2$CH$_2$SCN | OCH$_3$ | OCH$_3$ | |
| J-7(n = 0) | — | CH$_3$ | H | CH$_2$CH$_2$NO$_2$ | OCH$_3$ | OCH$_3$ | |
| J-7(n = 1) | — | H | H | CH$_2$CH$_2$N$_3$ | OCH$_3$ | OCH$_3$ | |
| J-7(n = 1) | — | H | H | CH$_2$CH$_2$SCN | OCH$_3$ | OCH$_3$ | |
| J-7(n = 1) | — | H | H | CH$_2$CH$_2$NO$_2$ | OCH$_3$ | OCH$_3$ | |
| J-8(n = 0) | — | H | H | CH$_2$CH$_2$N$_3$ | OCH$_3$ | OCH$_3$ | |
| J-8(n = 0) | — | H | H | CH$_2$CH$_2$N$_3$ | OCH$_3$ | CH$_3$ | |
| J-8(n = 0) | — | H | H | CH$_2$CH$_2$N$_3$ | CH$_3$ | CH$_3$ | |
| J-8(n = 0) | — | H | H | CH$_2$CH$_2$N$_3$ | Cl | OCH$_3$ | |
| J-8(n = 0) | H | H | 2-CH$_3$ | CH$_2$CH$_2$N$_3$ | OCH$_3$ | OCH$_3$ | |
| J-8(n = 0) | — | H | 2-Cl | CH$_2$CH$_2$N$_3$ | OCH$_3$ | OCH$_3$ | |
| J-8(n = 0) | — | H | 2-CF$_3$ | CH$_2$CH$_2$N$_3$ | OCH$_3$ | OCH$_3$ | |
| J-8(n = 0) | — | H | 2-OCH$_3$ | CH$_2$CH$_2$N$_3$ | OCH$_3$ | OCH$_3$ | |
| J-8(n = 0) | — | H | 2-SCH$_3$ | CH$_2$CH$_2$N$_3$ | OCH$_3$ | OCH$_3$ | |
| J-8(n = 0) | — | H | 2-SO$_2$CH$_3$ | CH$_2$CH$_2$N$_3$ | OCH$_3$ | OCH$_3$ | |
| J-8(n = 0) | — | H | 5-CH$_3$ | CH$_2$CH$_2$N$_3$ | OCH$_3$ | OCH$_3$ | |
| J-8(n = 0) | — | H | 5-Cl | CH$_2$CH$_2$N$_3$ | OCH$_3$ | OCH$_3$ | |
| J-8(n = 0) | — | H | 5-CF$_3$ | CH$_2$CH$_2$N$_3$ | OCH$_3$ | OCH$_3$ | |
| J-8(n = 0) | — | H | 5-OCH$_3$ | CH$_2$CH$_2$N$_3$ | OCH$_3$ | OCH$_3$ | |
| J-8(n = 0) | — | H | 5-SCH$_3$ | CH$_2$CH$_2$N$_3$ | OCH$_3$ | OCH$_3$ | |
| J-8(n = 0) | — | H | 5-SO$_2$CH$_3$ | CH$_2$CH$_2$N$_3$ | OCH$_3$ | OCH$_3$ | |
| J-8(n = 0) | — | H | 6-OCH$_3$ | CH$_2$CH$_2$N$_3$ | OCH$_3$ | OCH$_3$ | |
| J-8(n = 0) | — | H | H | (CH$_2$)$_3$N$_3$ | OCH$_3$ | OCH$_3$ | |
| J-8(n = 0) | — | H | H | CH$_2$CH$_2$SCN | OCH$_3$ | OCH$_3$ | |
| J-8(n = 0) | — | H | H | CH$_2$CH$_2$SCN | OCH$_3$ | CH$_3$ | |
| J-8(n = 0) | — | H | H | CH$_2$CH$_2$SCN | CH$_3$ | CH$_3$ | |
| J-8(n = 0) | — | H | H | CH$_2$CH$_2$SCN | Cl | OCH$_3$ | |
| J-8(n = 0) | — | H | H | (CH$_2$)$_3$SCN | OCH$_3$ | OCH$_3$ | |
| J-8(n = 0) | — | H | H | CH$_2$CH$_2$NO$_2$ | OCH$_3$ | OCH$_3$ | |
| J-8(n = 0) | — | H | H | CH$_2$CH$_2$NO$_2$ | OCH$_3$ | CH$_3$ | |
| J-8(n = 0) | — | H | H | CH$_2$CH$_2$NO$_2$ | CH$_3$ | CH$_3$ | |
| J-8(n = 0) | — | H | H | CH$_2$CH$_2$NO$_2$ | Cl | OCH$_3$ | |
| J-8(n = 0) | — | H | H | (CH$_2$)$_3$NO$_2$ | OCH$_3$ | OCH$_3$ | |
| J-8(n = 0) | CH$_2$ | H | H | CH$_2$CH$_2$N$_3$ | OCH$_3$ | OCH$_3$ | |
| J-8(n = 0) | CH$_2$ | H | H | CH$_2$CH$_2$SCN | OCH$_3$ | OCH$_3$ | |
| J-8(n = 0) | CH$_2$ | H | H | CH$_2$CH$_2$NO$_2$ | OCH$_3$ | OCH$_3$ | |
| J-8(n = 0) | — | CH$_3$ | H | CH$_2$CH$_2$N$_3$ | OCH$_3$ | OCH$_3$ | |
| J-8(n = 0) | — | CH$_3$ | H | CH$_2$CH$_2$SCN | OCH$_3$ | OCH$_3$ | |
| J-8(n = 0) | — | CH$_3$ | H | CH$_2$CH$_2$NO$_2$ | OCH$_3$ | OCH$_3$ | |
| J-8(n = 1) | — | H | H | CH$_2$CH$_2$N$_3$ | OCH$_3$ | OCH$_3$ | |
| J-8(n = 1) | — | H | H | CH$_2$CH$_2$SCN | OCH$_3$ | OCH$_3$ | |
| J-8(n = 1) | — | H | H | CH$_2$CH$_2$NO$_2$ | OCH$_3$ | OCH$_3$ | |
| J-9(R$^3$ = H) | | H | H | CH$_2$CH$_2$N$_3$ | OCH$_3$ | OCH$_3$ | |
| J-9(R$^3$ = H) | | H | H | CH$_2$CH$_2$N$_3$ | OCH$_3$ | CH$_3$ | |
| J-9(R$^3$ = H) | | H | H | CH$_2$CH$_2$N$_3$ | CH$_3$ | CH$_3$ | |
| J-9(R$^3$ = H) | | H | H | CH$_2$CH$_2$N$_3$ | Cl | OCH$_3$ | |
| J-9(R$^3$ = CH$_3$) | | H | H | CH$_2$CH$_2$N$_3$ | OCH$_3$ | OCH$_3$ | |
| J-9(R$^3$ = CH$_3$) | | H | H | CH$_2$CH$_2$N$_3$ | OCH$_3$ | CH$_3$ | |
| J-9(R$^3$ = CH$_3$) | | H | H | CH$_2$CH$_2$N$_3$ | CH$_3$ | CH$_3$ | |
| J-9(R$^3$ = CH$_3$) | | H | H | CH$_2$CH$_2$N$_3$ | Cl | OCH$_3$ | |
| J-9(R$^3$ = CH$_3$) | | H | Cl | CH$_2$CH$_2$N$_3$ | OCH$_3$ | OCH$_3$ | |
| J-9(R$^3$ = CH$_3$) | | H | CH$_3$ | CH$_2$CH$_2$N$_3$ | OCH$_3$ | OCH$_3$ | |
| J-9(R$^3$ = CH$_3$) | | H | H | (CH$_2$)$_3$N$_3$ | OCH$_3$ | OCH$_3$ | |
| J-9(R$^3$ = CH$_3$) | | H | H | CH$_2$CH$_2$SCN | OCH$_3$ | OCH$_3$ | |
| J-9(R$^3$ = CH$_3$) | | H | H | CH$_2$CH$_2$SCN | OCH$_3$ | CH$_3$ | |
| J-9(R$^3$ = CH$_3$) | | H | H | CH$_2$CH$_2$SCN | CH$_3$ | CH$_3$ | |
| J-9(R$^3$ = CH$_3$) | | H | H | CH$_2$CH$_2$SCN | Cl | OCH$_3$ | |
| J-9(R$^3$ = CH$_3$) | | H | H | (CH$_2$)$_3$SCN | OCH$_3$ | OCH$_3$ | |
| J-9(R$^3$ = CH$_3$) | | H | H | CH$_2$CH$_2$NO$_2$ | OCH$_3$ | OCH$_3$ | |
| J-9(R$^3$ = CH$_3$) | | H | H | CH$_2$CH$_2$NO$_2$ | OCH$_3$ | CH$_3$ | |

TABLE 1-continued

GENERAL FORMULA 1

| J | E | R | R¹/R² | Q | X | Y | m.p. °C. |
|---|---|---|---|---|---|---|---|
| J-9(R³ = CH₃) | | H | H | CH₂CH₂NO₂ | CH₃ | CH₃ | |
| J-9(R³ = CH₃) | | H | H | CH₂CH₂NO₂ | Cl | OCH₃ | |
| J-9(R³ = CH₃) | | H | H | (CH₂)₃NO₂ | OCH₃ | OCH₃ | |
| J-9(R³ = CH₃) | | CH₃ | H | CH₂CH₂N₃ | OCH₃ | OCH₃ | |
| J-9(R³ = CH₃) | | CH₃ | H | CH₂CH₂SCN | OCH₃ | OCH₃ | |
| J-9(R³ = CH₃) | | CH₃ | H | CH₂CH₂NO₂ | OCH₃ | OCH₃ | |
| J-9(R³ = H) | | H | H | CH₂CH₂SCN | OCH₃ | OCH₃ | |
| J-9(R³ = H) | | H | H | CH₂CH₂NO₂ | OCH₃ | OCH₃ | |
| J-10(R³ = H) | | H | H | CH₂CH₂N₃ | OCH₃ | OCH₃ | |
| J-10(R³ = H) | | H | H | CH₂CH₂N₃ | OCH₃ | CH₃ | |
| J-10(R³ = H) | | H | H | CH₂CH₂N₃ | CH₃ | CH₃ | |
| J-10(R³ = H) | | H | H | CH₂CH₂N₃ | Cl | OCH₃ | |
| J-10(R³ = CH₃) | | H | H | CH₂CH₂N₃ | OCH₃ | OCH₃ | |
| J-10(R³ = CH₃) | | H | H | CH₂CH₂N₃ | OCH₃ | CH₃ | |
| J-10(R³ = CH₃) | | H | H | CH₂CH₂N₃ | CH₃ | CH₃ | |
| J-10(R³ = CH₃) | | H | H | CH₂CH₂N₃ | Cl | OCH₃ | |
| J-10(R³ = CH₃) | | H | Cl | CH₂CH₂N₃ | OCH₃ | OCH₃ | |
| J-10(R³ = CH₃) | | H | CH₃ | CH₂CH₂N₃ | OCH₃ | OCH₃ | |
| J-10(R³ = CH₃) | | H | H | (CH₂)₃N₃ | OCH₃ | OCH₃ | |
| J-10(R³ = CH₃) | | H | H | CH₂CH₂SCN | OCH₃ | OCH₃ | |
| J-10(R³ =CH₃) | | H | H | CH₂CH₂SCN | OCH₃ | CH₃ | |
| J-10(R³ = CH₃) | | H | H | CH₂CH₂SCN | CH₃ | CH₃ | |
| J-10(R³ = CH₃) | | H | H | CH₂CH₂SCN | Cl | OCH₃ | |
| J-10(R³ = CH₃) | | H | H | (CH₂)₃SCN | OCH₃ | OCH₃ | |
| J-10(R³ = CH₃) | | H | H | CH₂CH₂NO₂ | OCH₃ | OCH₃ | |
| J-10(R³ = CH₃) | | H | H | CH₂CH₂NO₂ | OCH₃ | CH₃ | |
| J-10(R³ = CH₃) | | H | H | CH₂CH₂NO₂ | CH₃ | CH₃ | |
| J-10(R³ = CH₃) | | H | H | CH₂CH₂NO₂ | Cl | OCH₃ | |
| J-10(R³ = CH₃) | | H | H | (CH₂)₃NO₂ | OCH₃ | OCH₃ | |
| J-10(R³ = CH₃) | | CH₃ | H | CH₂CH₂N₃ | OCH₃ | OCH₃ | |
| J-10(R³ = CH₃) | | CH₃ | H | CH₂CH₂SCN | OCH₃ | OCH₃ | |
| J-10(R³ = CH₃) | | CH₃ | H | CH₂CH₂NO₂ | OCH₃ | OCH₃ | |
| J-10(R³ = H) | | H | H | CH₂CH₂SCN | OCH₃ | OCH₃ | |
| J-10(R³ = H) | | H | H | CH₂CH₂NO₂ | OCH₃ | OCH₃ | |
| J-11(R³ = H) | | H | H | CH₂CH₂N₃ | OCH₃ | OCH₃ | |
| J-11(R³ = H) | | H | H | CH₂CH₂N₃ | OCH₃ | CH₃ | |
| J-11(R³ = H) | | H | H | CH₂CH₂N₃ | CH₃ | CH₃ | |
| J-11(R³ = H) | | H | H | CH₂CH₂N₃ | Cl | OCH₃ | |
| J-11(R³ = CH₃) | | H | H | CH₂CH₂N₃ | OCH₃ | OCH₃ | |
| J-11(R³ = CH₃) | | H | H | CH₂CH₂N₃ | OCH₃ | CH₃ | |
| J-11(R³ = CH₃) | | H | H | CH₂CH₂N₃ | CH₃ | CH₃ | |
| J-11(R³ = CH₃) | | H | H | CH₂CH₂N₃ | Cl₃ | OCH₃ | |
| J-11(R³ = C₆H₅) | | H | H | CH₂CH₂N₃ | OCH₃ | OCH₃ | |
| J-11(R³ = CH₂CH = CH₂) | | H | H | CH₂CH₂N₃ | OCH₃ | OCH₃ | |
| J-11(R³ = CH₂CN) | | H | H | CH₂CH₂N₃ | OCH₃ | OCH₃ | |
| J-11(R³ = CH₃) | | H | Cl | CH₂CH₂N₃ | OCH₃ | OCH₃ | |
| J-11(R³ = CH₃) | | H | CH₃ | CH₂CH₂N₃ | OCH₃ | OCH₃ | |
| J-11(R³ = CH₃) | | H | H | (CH₂)₃N₃ | OCH₃ | OCH₃ | |
| J-11(R³ = CH₃) | | H | H | CH₂CH₂SCN | OCH₃ | OCH₃ | |
| J-11(R³ = CH₃) | | H | H | CH₂CH₂SCN | OCH₃ | CH₃ | |
| J-11(R³ = CH₃) | | H | H | CH₂CH₂SCN | CH₃ | CH₃ | |
| J-11(R³ = CH₃) | | H | H | CH₂CH₂SCN | Cl | OCH₃ | |
| J-11(R³ = CH₃) | | H | H | (CH₂)₃SCN | OCH₃ | OCH₃ | |
| J-11(R³ = CH₃) | | H | H | CH₂CH₂NO₂ | OCH₃ | OCH₃ | |
| J-11(R³ = CH₃) | | H | H | CH₂CH₂NO₂ | OCH₃ | CH₃ | |
| J-11(R³ = CH₃) | | H | H | CH₂CH₂NO₂ | CH₃ | CH₃ | |
| J-11(R³ = CH₃) | | H | H | CH₂CH₂NO₂ | Cl | OCH₃ | |
| J-11(R³ = CH₃) | | H | H | (CH₂)₃NO₂ | OCH₃ | OCH₃ | |
| J-11(R³ = CH₃) | | CH₃ | H | CH₂CH₂N₃ | OCH₃ | OCH₃ | |
| J-11(R³ = CH₃) | | CH₃ | H | CH₂CH₂SCN | OCH₃ | OCH₃ | |
| J-11(R³ = CH₃) | | CH₃ | H | CH₂CH₂NO₂ | OCH₃ | OCH₃ | |
| J-11(R³ = H) | | H | H | CH₂CH₂SCN | OCH₃ | OCH₃ | |
| J-11(R³ = H) | | H | H | CH₂CH₂NO₂ | OCH₃ | OCH₃ | |
| J-12(R³ = H) | | H | H | CH₂CH₂N₃ | OCH₃ | OCH₃ | |
| J-12(R³ = H) | | H | H | CH₂CH₂N₃ | OCH₃ | CH₃ | |
| J-12(R³ = H) | | H | H | CH₂CH₂N₃ | CH₃ | CH₃ | |
| J-12(R³ = H) | | H | H | CH₂CH₂N₃ | Cl | OCH₃ | |
| J-12(R³ = CH₃) | | H | H | CH₂CH₂N₃ | OCH₃ | OCH₃ | |
| J-12(R³ = CH₃) | | H | H | CH₂CH₂N₃ | OCH₃ | CH₃ | |
| J-12(R³ = CH₃) | | H | H | CH₂CH₂N₃ | CH₃ | CH₃ | |
| J-12(R³ = CH₃) | | H | H | CH₂CH₂N₃ | Cl | OCH₃ | |
| J-12(R³ = CH₃) | | H | Cl | CH₂CH₂N₃ | OCH₃ | OCH₃ | |
| J-12(R³ = CH₃) | | H | CH₃ | CH₂CH₂N₃ | OCH₃ | OCH₃ | |
| J-12(R³ = CH₃) | | H | H | (CH₂)₃N₃ | OCH₃ | OCH₃ | |
| J-12(R³ = CH₃) | | H | H | CH₂CH₂SCN | OCH₃ | OCH₃ | |
| J-12(R³ = CH₃) | | H | H | CH₂CH₂SCN | OCH₃ | CH₃ | |
| J-12)R³ = CH₃) | | H | H | CH₂CH₂SCN | CH₃ | CH₃ | |
| J-12(R³ = CH₃) | | H | H | CH₂CH₂SCN | Cl | OCH₃ | |
| J-12(R³ = CH₃) | | H | H | (CH₂)₃SCN | OCH₃ | OCH₃ | |
| J-12(R³ = CH₃) | | H | H | CH₂CH₂NO₂ | OCH₃ | OCH₃ | |

TABLE 1-continued

GENERAL FORMULA 1

| J | E | R | R¹/R² | Q | X | Y | m.p. °C. |
|---|---|---|---|---|---|---|---|
| J-12(R³ = CH₃) | — | H | H | CH₂CH₂NO₂ | OCH₃ | CH₃ | |
| J-12(R³ = CH₃) | — | H | H | CH₂CH₂NO₂ | CH₃ | CH₃ | |
| J-12(R³ = CH₃) | — | H | H | CH₂CH₂NO₂ | Cl | OCH₃ | |
| J-12(R³ = CH₃) | — | H | H | (CH₂)₃NO₂ | OCH₃ | OCH₃ | |
| J-12(R³ = CH₃) | — | CH₃ | H | CH₂CH₂N₃ | OCH₃ | OCH₃ | |
| J-12(R³ = CH₃) | — | CH₃ | H | CH₂CH₂SCN | OCH₃ | OCH₃ | |
| J-12(R³ = CH₃) | — | CH₃ | H | CH₂CH₂NO₂ | OCH₃ | OCH₃ | |
| J-12(R³ = H) | — | H | H | CH₂CH₂SCN | OCH₃ | OCH₃ | |
| J-12(R³ = H) | — | H | H | CH₂CH₂NO₂ | OCH₃ | OCH₃ | |

TABLE 2

GENERAL FORMULA 2

| J | E | R | R¹/R² | Q | X | Y | m.p. °C. |
|---|---|---|---|---|---|---|---|
| J-1 | — | H | H | CH₂CH₂N₃ | CH₃ | CH₃ | |
| J-1 | — | H | H | CH₂CH₂N₃ | OCH₃ | CH₃ | 168–169.5 |
| J-1 | — | H | H | CH₂CH₂N₃ | OCH₃ | OCH₃ | |
| J-1 | — | H | H | CH₂CH₂N₃ | OCH₃ | OC₂H₅ | |
| J-1 | — | H | H | CH₂CH₂N₃ | OCH₃ | CH(OCH₃)₂ | |
| J-1 | — | H | H | CH₂CH₂N₃ | CH₃ | 1,3-dioxolan-2-yl | |
| J-1 | — | H | H | CH₂CH₂N₃ | OCH₃ | 1,3-dioxolan-2-yl | |
| J-1 | — | H | H | CH₂CH₂N₃ | OCH₃ | 2-methyl-1,3-oxathiolan-2-yl | |
| J-1 | — | H | H | CH₂CH₂N₃ | OCH₃ | 1,3-oxathian-2-yl | |
| J-1 | — | H | H | CH₂CH₂N₃ | OCH₃ | 2-methyl-1,3-dithian-2-yl | |
| J-1 | — | H | H | CH₂CH₂N₃ | OCH₃ | 4-methyl-1,3-dioxolan-2-yl | |
| J-1 | — | H | H | CH₂CH₂N₃ | OCH₃ | 2,4-dimethyl-1,3-dithiolan-2-yl | |
| J-1 | — | H | H | CH₂CH₂N₃ | H | CH₃ | |
| J-1 | — | H | H | CH₂CH₂N₃ | OCH₃ | H | |
| J-1 | — | H | H | CH₂CH₂N₃ | OC₂H₅ | OC₂H₅ | |
| J-1 | — | H | H | CH₂CH₂N₃ | CF₃ | CF₃ | |
| J-1 | — | H | H | CH₂CH₂N₃ | OCH₂CH₂F | OCH₃ | |
| J-1 | — | H | H | CH₂CH₂N₃ | OCH₂CHF₂ | OCH₃ | |
| J-1 | — | H | H | CH₂CH₂N₃ | OCH₂CF₃ | OCH₃ | |
| J-1 | — | H | H | CH₂CH₂N₃ | OCH₂CF₃ | CH₃ | |
| J-1 | — | H | H | CH₂CH₂N₃ | OCH₂CF₃ | N(CH₃)₂ | |
| J-1 | — | H | H | CH₂CH₂N₃ | CH₃ | CH₂OCH₃ | |
| J-1 | — | H | H | CH₂CH₂N₃ | OCH₃ | CH₂OCH₃ | |
| J-1 | — | H | H | CH₂CH₂N₃ | OCH₃ | CH₂OC₂H₅ | |
| J-1 | — | H | H | CH₂CH₂N₃ | CH₂F | OCH₃ | |
| J-1 | — | H | H | CH₂CH₂N₃ | CH₂Cl | OCH₃ | |
| J-1 | — | H | H | CH₂CH₂N₃ | CH₂Br | OCH₃ | |
| J-1 | — | H | H | CH₂CH₂N₃ | CH₂OH | OCH₃ | |
| J-1 | — | H | H | CH₂CH₂N₃ | CH₂CN | OCH₃ | |
| J-1 | — | H | H | CH₂CH₂N₃ | CH₂CO₂CH₃ | OCH₃ | |
| J-1 | — | H | H | CH₂CH₂N₃ | OCH₃ | CN | |
| J-1 | — | H | H | CH₂CH₂N₃ | OCH₃ | N₃ | |
| J-1 | — | H | H | CH₂CH₂N₃ | OCH₃ | CHO | |
| J-1 | — | H | H | CH₂CH₂N₃ | OCH₃ | C(O)CH₃ | |
| J-1 | — | H | H | CH₂CH₂N₃ | CH₃ | SCH₃ | |
| J-1 | — | H | H | CH₂CH₂N₃ | OCH₃ | SC₂H₅ | |
| J-1 | — | H | H | CH₂CH₂N₃ | SCH₃ | SCH₃ | |
| J-1 | — | H | H | CH₂CH₂N₃ | CH₃ | CH₂SCH₃ | |
| J-1 | — | H | H | CH₂CH₂N₃ | OCH₃ | CH₂SC₂H₅ | |
| J-1 | — | H | H | CH₂CH₂N₃ | OCH₃ | NHCH₃ | |
| J-1 | — | H | H | CH₂CH₂N₃ | OC₂H₅ | NHCH₃ | |
| J-1 | — | H | H | CH₂CH₂N₃ | OCH₃ | N(CH₃)₂ | |
| J-1 | — | H | H | CH₂CH₂N₃ | OC₂H₅ | N(CH₃)₂ | |
| J-1 | — | H | H | CH₂CH₂N₃ | OCH₃ | N(OCH₃)CH₃ | |
| J-1 | — | H | H | CH₂CH₂N₃ | OCH₃ | C≡CH | |
| J-1 | — | H | H | CH₂CH₂N₃ | OCH₃ | C≡CCH₃ | |
| J-1 | — | H | H | CH₂CH₂N₃ | OCH₃ | CH₂C≡CH | |
| J-1 | — | H | H | CH₂CH₂N₃ | CH₃ | OCH₂C≡CH | |
| J-1 | — | H | H | CH₂CH₂N₃ | CH₃ | OCH₂CH=CH₂ | |
| J-1 | — | H | H | CH₂CH₂N₃ | CH₃ | OCH₂OCH₃ | |
| J-1 | — | H | H | CH₂CH₂N₃ | CH₃ | OCH₂CH₂OCH₃ | |
| J-1 | — | H | H | CH₂CH₂N₃ | OCH₃ | SCF₂H | |
| J-1 | — | H | H | CH₂CH₂N₃ | cyclopropyl | OCH₃ | |
| J-1 | — | H | H | CH₂CH₂N₃ | cyclopropyl | CH₃ | |
| J-1 | CH₂ | H | H | CH₂CH₂N₃ | OCH₃ | OCH₃ | |
| J-1 | CH₂ | H | H | CH₂CH₂N₃ | OCH₃ | CH₃ | |
| J-1 | CH₂ | H | H | CH₂CH₂N₃ | CH₃ | CH₃ | |
| J-1 | — | CH₃ | H | CH₂CH₂N₃ | OCH₃ | OCH₃ | |
| J-1 | — | CH₃ | H | CH₂CH₂N₃ | OCH₃ | CH₃ | |
| J-1 | — | CH₃ | H | CH₂CH₂N₃ | CH₃ | CH₃ | |
| J-1 | — | H | 5-Cl | CH₂CH₂N₃ | OCH₃ | OCH₃ | |
| J-1 | — | H | 5-Cl | CH₂CH₂N₃ | OCH₃ | CH₃ | |

TABLE 2-continued

GENERAL FORMULA 2

| J | E | R | R¹/R₂ | Q | X | Y | m.p. °C. |
|---|---|---|---|---|---|---|---|
| J-1 | — | H | 5-Cl | $CH_2CH_2N_3$ | $OC_2H_5$ | $OC_2H_5$ | |
| J-1 | — | H | 5-Cl | $CH_2CH_2N_3$ | $OC_2H_5$ | $NHCH_3$ | |
| J-1 | — | H | 5-$OCH_3$ | $CH_2CH_2N_3$ | $OCH_3$ | $OCH_3$ | |
| J-1 | — | H | 5-$OCH_3$ | $CH_2CH_2N_3$ | $OCH_3$ | $CH_3$ | |
| J-1 | — | H | 5-$OCH_3$ | $CH_2CH_2N_3$ | $OC_2H_5$ | $NHCH_3$ | |
| J-1 | — | H | 5-$OCH_3$ | $CH_2CH_2N_3$ | $OC_2H_5$ | $OC_2H_5$ | |
| J-1 | — | H | 5-$OC_2H_5$ | $CH_2CH_2N_3$ | $OCH_3$ | $OCH_3$ | |
| J-1 | — | H | 5-F | $CH_2CH_2N_3$ | $OCH_3$ | $OCH_3$ | |
| J-1 | — | H | 5-$CH_3$ | $CH_2CH_2N_3$ | $OCH_3$ | $OCH_3$ | |
| J-1 | — | H | 5-$SCH_3$ | $CH_2CH_2N_3$ | $OCH_3$ | $OCH_3$ | |
| J-1 | — | H | 5-$N(CH_3)_2$ | $CH_2CH_2N_3$ | $OCH_3$ | $OCH_3$ | |
| J-1 | — | H | 5-$OCH_2CF_3$ | $CH_2CH_2N_3$ | $OCH_3$ | $OCH_3$ | |
| J-1 | — | H | 5-$OCH_2CF_3$ | $CH_2CH_2N_3$ | $OCH_3$ | $CH_3$ | |
| J-1 | — | H | 5-$NO_2$ | $CH_2CH_2N_3$ | $OCH_3$ | $OCH_3$ | |
| J-1 | — | H | 5-Br | $CH_2CH_2N_3$ | $OCH_3$ | $OCH_3$ | |
| J-1 | — | H | 5-CN | $CH_2CH_2N_3$ | $OCH_3$ | $OCH_3$ | |
| J-1 | — | H | 3-Cl | $CH_2CH_2N_3$ | $OCH_3$ | $OCH_3$ | |
| J-1 | — | H | 3-F | $CH_2CH_2N_3$ | $OCH_3$ | $OCH_3$ | |
| J-1 | — | H | 3-Br | $CH_2CH_2N_3$ | $OCH_3$ | $OCH_3$ | |
| J-1 | — | H | 3-$CH_3$ | $CH_2CH_2N_3$ | $OCH_3$ | $OCH_3$ | |
| J-1 | — | H | 3-$OCH_3$ | $CH_2CH_2N_3$ | $OCH_3$ | $OCH_3$ | |
| J-1 | — | H | 3-$NO_2$ | $CH_2CH_2N_3$ | $OCH_3$ | $OCH_3$ | |
| J-1 | — | H | 6-Cl | $CH_2CH_2N_3$ | $OCH_3$ | $OCH_3$ | |
| J-1 | — | H | 6-F | $CH_2CH_2N_3$ | $OCH_3$ | $OCH_3$ | |
| J-1 | — | H | 6-Br | $CH_2CH_2N_3$ | $OCH_3$ | $OCH_3$ | |
| J-1 | — | H | 6-$CH_3$ | $CH_2CH_2N_3$ | $OCH_3$ | $OCH_3$ | |
| J-1 | — | H | 6-$OCH_3$ | $CH_2CH_2N_3$ | $OCH_3$ | $OCH_3$ | |
| J-1 | — | H | 6-$NO_2$ | $CH_2CH_2N_3$ | $OCH_3$ | $OCH_3$ | |
| J-1 | — | H | H | $CH(CH_3)CH_2N_3$ | $OCH_3$ | $OCH_3$ | |
| J-1 | — | H | H | $CH(CH_3)CH_2N_3$ | $OCH_3$ | $CH_3$ | |
| J-1 | — | H | H | $CH(CH_3)CH_2N_3$ | $OCH_2CF_3$ | $N(CH_3)_2$ | |
| J-1 | — | H | H | $CH(CH_3)CH_2N_3$ | $OC_2H_5$ | $OC_2H_5$ | |
| J-1 | — | H | H | $CH(CH_3)CH_2N_3$ | $OCH_3$ | $N(CH_3)_2$ | |
| J-1 | — | H | H | $CH(CH_3)CH_2N_3$ | $OC_2H_5$ | $NHCH_3$ | |
| J-1 | — | H | H | $CH(CH_3)CH_2N_3$ | $OC_2H_5$ | $N(CH_3)_2$ | |
| J-1 | — | H | H | $CH_2CH(CH_3)N_3$ | $OCH_3$ | $OCH_3$ | |
| J-1 | — | H | H | $CH_2CH(CH_3)N_3$ | $OCH_3$ | $CH_3$ | |
| J-1 | — | H | H | $CH_2CH(CH_3)N_3$ | $OC_2H_5$ | $OC_2H_5$ | |
| J-1 | — | H | H | $(CH_2)_3N_3$ | $OCH_3$ | $OCH_3$ | |
| J-1 | — | H | H | $(CH_2)_3N_3$ | $OCH_3$ | $CH_3$ | |
| J-1 | — | H | H | $(CH_2)_3N_3$ | $OC_2H_5$ | $OC_2H_5$ | |
| J-1 | — | H | H | $(CH_2)_3N_3$ | $OC_2H_5$ | $NHCH_3$ | |
| J-1 | — | H | H | $(CH_2)_3N_3$ | $OC_2H_5$ | $N(CH_3)_2$ | |
| J-1 | — | H | H | $CH(CH_3)CH_2CH_2N_3$ | $OCH_3$ | $OCH_3$ | |
| J-1 | — | H | H | $CH(CH_3)CH_2CH_2N_3$ | $OCH_3$ | $CH_3$ | |
| J-1 | — | H | H | $CH(CH_3)CH_2CH_2N_3$ | $OC_2H_5$ | $OC_2H_5$ | |
| J-1 | — | H | H | $CH_2CH(CH_3)CH_2N_3$ | $OCH_3$ | $OCH_3$ | |
| J-1 | — | H | H | $CH_2CH(CH_3)CH_2N_3$ | $OCH_3$ | $CH_3$ | |
| J-1 | — | H | H | $CH_2CH(CH_3)CH_2N_3$ | $OC_2H_5$ | $OC_2H_5$ | |
| J-1 | — | H | H | $(CH_2)_2CH(CH_3)N_3$ | $OCH_3$ | $OCH_3$ | |
| J-1 | — | H | H | $(CH_2)_2CH(CH_3)N_3$ | $OCH_3$ | $CH_3$ | |
| J-1 | — | H | H | $(CH_2)_2CH(CH_3)N_3$ | $OC_2H_5$ | $OC_2H_5$ | |
| J-1 | — | H | H | $CH_2CH_2SCN$ | $OCH_3$ | $OCH_3$ | |
| J-1 | — | H | H | $CH_2CH_2SCN$ | $OC_2H_5$ | $OC_2H_5$ | |
| J-1 | — | H | H | $CH_2CH_2SCN$ | $OCH_3$ | $CH_3$ | 172–175 |
| J-1 | — | H | H | $CH_2CH_2SCN$ | $OC_2H_5$ | $N(CH_3)_2$ | |
| J-1 | — | H | H | $CH_2CH_2SCN$ | $OC_2H_5$ | $NHCH_3$ | |
| J-1 | $CH_2$ | H | H | $CH_2CH_2SCN$ | $OCH_3$ | $OCH_3$ | |
| J-1 | — | $CH_3$ | H | $CH_2CH_2SCN$ | $OCH_3$ | $OCH_3$ | |
| J-1 | — | H | 5-Cl | $CH_2CH_2SCN$ | $OCH_3$ | $OCH_3$ | |
| J-1 | — | H | 5-Cl | $CH_2CH_2SCN$ | $OCH_3$ | $CH_3$ | |
| J-1 | — | H | 5-$OCH_3$ | $CH_2CH_2SCN$ | $OCH_3$ | $OCH_3$ | |
| J-1 | — | H | 5-$OCH_3$ | $CH_2CH_2SCN$ | $OCH_3$ | $CH_3$ | |
| J-1 | — | H | 5-$CH_3$ | $CH_2CH_2SCN$ | $OCH_3$ | $OCH_3$ | |
| J-1 | — | H | 5-$OCH_2CF_3$ | $CH_2CH_2SCN$ | $OCH_3$ | $OCH_3$ | |
| J-1 | — | H | 3-Cl | $CH_2CH_2SCN$ | $OCH_3$ | $OCH_3$ | |
| J-1 | — | H | 3-$CH_3$ | $CH_2CH_2SCN$ | $OCH_3$ | $OCH_3$ | |
| J-1 | — | H | 6-Cl | $CH_2CH_2SCN$ | $OCH_3$ | $OCH_3$ | |
| J-1 | — | H | 6-$CH_3$ | $CH_2CH_2SCN$ | $OCH_3$ | $OCH_3$ | |
| J-1 | — | H | H | $CH(CH_3)CH_2SCN$ | $OCH_3$ | $OCH_3$ | |
| J-1 | — | H | H | $CH(CH_3)CH_2SCN$ | $OC_2H_5$ | $OC_2H_5$ | |
| J-1 | — | H | H | $CH(CH_3)CH_2SCN$ | $OCH_3$ | $CH_3$ | |
| J-1 | — | H | H | $CH(CH_3)CH_2SCN$ | $OC_2H_5$ | $N(CH_3)_2$ | |
| J-1 | — | H | H | $CH(CH_3)CH_2SCN$ | $OC_2H_5$ | $NHCH_3$ | |
| J-1 | — | H | H | $CH_2CH(CH_3)SCN$ | $OCH_3$ | $OCH_3$ | |
| J-1 | — | H | H | $CH_2CH(CH_3)SCN$ | $OCH_3$ | $CH_3$ | |
| J-1 | — | H | H | $CH_2CH(CH_3)SCN$ | $OC_2H_5$ | $OC_2H_5$ | |
| J-1 | — | H | H | $(CH_2)_3SCN$ | $OCH_3$ | $OCH_3$ | |
| J-1 | — | H | H | $(CH_2)_3SCN$ | $OC_2H_5$ | $OC_2H_5$ | |
| J-1 | — | H | H | $(CH_2)_3SCN$ | $OCH_3$ | $CH_3$ | |

TABLE 2-continued
GENERAL FORMULA 2

| J | E | R | R¹/R₂ | Q | X | Y | m.p. °C. |
|---|---|---|-------|---|---|---|----------|
| J-1 | — | H | H | $(CH_2)_3SCN$ | $OC_2H_5$ | $N(CH_3)_2$ | |
| J-1 | — | H | H | $(CH_2)_3SCN$ | $OC_2H_5$ | $NHCH_3$ | |
| J-1 | — | H | H | $CH(CH_3)CH_2CH_2SCN$ | $OCH_3$ | $OCH_3$ | |
| J-1 | — | H | H | $CH(CH_3)CH_2CH_2SCN$ | $OCH_3$ | $CH_3$ | |
| J-1 | — | H | H | $CH(CH_3)CH_2CH_2SCN$ | $OC_2H_5$ | $OC_2H_5$ | |
| J-1 | — | H | H | $CH(CH_3)CH_2CH_2SCN$ | $OC_2H_5$ | $N(CH_3)_2$ | |
| J-1 | — | H | H | $CH_2CH(CH_3)CH_2SCN$ | $OCH_3$ | $OCH_3$ | |
| J-1 | — | H | H | $CH_2CH(CH_3)CH_2SCN$ | $OCH_3$ | $CH_3$ | |
| J-1 | — | H | H | $CH_2CH(CH_3)CH_2SCN$ | $OC_2H_5$ | $OC_2H_5$ | |
| J-1 | — | H | H | $(CH_2)_2CH(CH_3)SCN$ | $OCH_3$ | $OCH_3$ | |
| J-1 | — | H | H | $(CH_2)_2CH(CH_3)SCN$ | $OCH_3$ | $CH_3$ | |
| J-1 | — | H | H | $(CH_2)_2CH(CH_3)SCN$ | $OC_2H_5$ | $OC_2H_5$ | |
| J-1 | — | H | H | $CH_2CH_2NO_2$ | $OCH_3$ | $OCH_3$ | |
| J-1 | — | H | H | $CH_2CH_2NO_2$ | $OCH_3$ | $CH_3$ | |
| J-1 | — | H | H | $CH_2CH_2NO_2$ | $OC_2H_5$ | $OC_2H_5$ | |
| J-1 | — | H | H | $CH_2CH_2NO_2$ | $OC_2H_5$ | $N(CH_3)_2$ | |
| J-1 | — | H | H | $CH_2CH_2NO_2$ | $OC_2H_5$ | $NHCH_3$ | |
| J-1 | $CH_2$ | H | H | $CH_2CH_2NO_2$ | $OCH_3$ | $OCH_3$ | |
| J-1 | — | $CH_3$ | H | $CH_2CH_2NO_2$ | $OCH_3$ | $OCH_3$ | |
| J-1 | — | H | 5-Cl | $CH_2CH_2NO_2$ | $OCH_3$ | $OCH_3$ | |
| J-1 | — | H | 5-Cl | $CH_2CH_2NO_2$ | $OCH_3$ | $CH_3$ | |
| J-1 | — | H | 5-$OCH_3$ | $CH_2CH_2NO_2$ | $OCH_3$ | $OCH_3$ | |
| J-1 | — | H | 5-$OCH_3$ | $CH_2CH_2NO_2$ | $OCH_3$ | $CH_3$ | |
| J-1 | — | H | 5-$CH_3$ | $CH_2CH_2NO_2$ | $OCH_3$ | $OCH_3$ | |
| J-1 | — | H | 5-$OCH_2CF_3$ | $CH_2CH_2NO_2$ | $OCH_3$ | $OCH_3$ | |
| J-1 | — | H | 3-Cl | $CH_2CH_2NO_2$ | $OCH_3$ | $OCH_3$ | |
| J-1 | — | H | 3-$CH_3$ | $CH_2CH_2NO_2$ | $OCH_3$ | $OCH_3$ | |
| J-1 | — | H | 6-Cl | $CH_2CH_2NO_2$ | $OCH_3$ | $OCH_3$ | |
| J-1 | — | H | 6-$CH_3$ | $CH_2CH_2NO_2$ | $OCH_3$ | $OCH_3$ | |
| J-1 | — | H | H | $CH(CH_3)CH_2NO_2$ | $OCH_3$ | $OCH_3$ | |
| J-1 | — | H | H | $CH(CH_3)CH_2NO_2$ | $OCH_3$ | $CH_3$ | |
| J-1 | — | H | H | $CH(CH_3)CH_2NO_2$ | $OC_2H_5$ | $OC_2H_5$ | |
| J-1 | — | H | H | $CH(CH_3)CH_2NO_2$ | $OC_2H_5$ | $N(CH_3)_2$ | |
| J-1 | — | H | H | $CH(CH_3)CH_2NO_2$ | $OC_2H_5$ | $NHCH_3$ | |
| J-1 | — | H | H | $CH_2CH(CH_3)NO_2$ | $OCH_3$ | $OCH_3$ | |
| J-1 | — | H | H | $CH_2CH(CH_3)NO_2$ | $OCH_3$ | $CH_3$ | |
| J-1 | — | H | H | $CH_2CH(CH_3)NO_2$ | $OC_2H_5$ | $OC_2H_5$ | |
| J-1 | — | H | H | $(CH_2)_3NO_2$ | $OCH_3$ | $OCH_3$ | |
| J-1 | — | H | H | $(CH_2)_3NO_2$ | $OC_2H_5$ | $OC_2H_5$ | |
| J-1 | — | H | H | $(CH_2)_3NO_2$ | $OCH_3$ | $CH_3$ | |
| J-1 | — | H | H | $(CH_2)_3NO_2$ | $OC_2H_5$ | $N(CH_3)_2$ | |
| J-1 | — | H | H | $(CH_2)_3NO_2$ | $OC_2H_5$ | $NHCH_3$ | |
| J-1 | — | H | H | $CH(CH_3)CH_2CH_2NO_2$ | $OCH_3$ | $OCH_3$ | |
| J-1 | — | H | H | $CH(CH_3)CH_2CH_2NO_2$ | $OCH_3$ | $CH_3$ | |
| J-1 | — | H | H | $CH(CH_3)CH_2CH_2NO_2$ | $OC_2H_5$ | $OC_2H_5$ | |
| J-1 | — | H | H | $CH_2CH(CH_3)CH_2NO_2$ | $OCH_3$ | $OCH_3$ | |
| J-1 | — | H | H | $CH_2CH(CH_3)CH_2NO_2$ | $OCH_3$ | $CH_3$ | |
| J-1 | — | H | H | $CH_2CH(CH_3)CH_2NO_2$ | $OC_2H_5$ | $OC_2H_5$ | |
| J-1 | — | H | H | $(CH_2)_2CH(CH_3)NO_2$ | $OCH_3$ | $OCH_3$ | |
| J-1 | — | H | H | $(CH_2)_2CH(CH_3)NO_2$ | $OCH_3$ | $CH_3$ | |
| J-1 | — | H | H | $(CH_2)_2CH(CH_3)NO_2$ | $OC_2H_5$ | $OC_2H_5$ | |
| J-2 | — | H | H | $CH_2CH_2N_3$ | $OCH_3$ | $OCH_3$ | |
| J-2 | — | H | H | $CH_2CH_2N_3$ | $OCH_3$ | $CH_3$ | |
| J-2 | — | H | H | $CH_2CH_2N_3$ | $OC_2H_5$ | $OC_2H_5$ | |
| J-2 | — | H | H | $CH_2CH_2N_3$ | $OC_2H_5$ | $N(CH_3)_2$ | |
| J-2 | — | H | H | $CH_2CH_2N_3$ | $OC_2H_5$ | $NHCH_3$ | |
| J-2 | — | H | 4-$CH_3$ | $CH_2CH_2N_3$ | $OCH_3$ | $OCH_3$ | |
| J-2 | — | H | 4-Cl | $CH_2CH_2N_3$ | $OCH_3$ | $OCH_3$ | |
| J-2 | — | H | 4-F | $CH_2CH_2N_3$ | $OCH_3$ | $OCH_3$ | |
| J-2 | — | H | 4-Br | $CH_2CH_2N_3$ | $OCH_3$ | $OCH_3$ | |
| J-2 | — | H | 4-$OCH_3$ | $CH_2CH_2N_3$ | $OCH_3$ | $OCH_3$ | |
| J-2 | — | H | 5-$CH_3$ | $CH_2CH_2N_3$ | $OCH_3$ | $OCH_3$ | |
| J-2 | — | H | 5-Cl | $CH_2CH_2N_3$ | $OCH_3$ | $OCH_3$ | |
| J-2 | — | H | 5-F | $CH_2CH_2N_3$ | $OCH_3$ | $OCH_3$ | |
| J-2 | — | H | 5-Br | $CH_2CH_2N_3$ | $OCH_3$ | $OCH_3$ | |
| J-2 | — | H | 5-$OCH_3$ | $CH_2CH_2N_3$ | $OCH_3$ | $OCH_3$ | |
| J-2 | — | H | H | $(CH_2)_3N_3$ | $OCH_3$ | $OCH_3$ | |
| J-2 | — | H | H | $(CH_2)_3N_3$ | $OCH_3$ | $CH_3$ | |
| J-2 | — | H | H | $CH_2CH_2SCN$ | $OCH_3$ | $OCH_3$ | |
| J-2 | — | H | H | $CH_2CH_2SCN$ | $OC_2H_5$ | $OC_2H_5$ | |
| J-2 | — | H | H | $CH_2CH_2SCN$ | $OCH_3$ | $CH_3$ | |
| J-2 | — | H | H | $CH_2CH_2SCN$ | $OC_2H_5$ | $N(CH_3)_2$ | |
| J-2 | — | H | H | $CH_2CH_2SCN$ | $OC_2H_5$ | $NHCH_3$ | |
| J-2 | — | H | H | $(CH_2)_3SCN$ | $OCH_3$ | $OCH_3$ | |
| J-2 | — | H | H | $(CH_2)_3SCN$ | $OCH_3$ | $CH_3$ | |
| J-2 | — | H | H | $CH_2CH_2NO_2$ | $OCH_3$ | $OCH_3$ | |
| J-2 | — | H | H | $CH_2CH_2NO_2$ | $OC_2H_5$ | $OC_2H_5$ | |
| J-2 | — | H | H | $CH_2CH_2NO_2$ | $OCH_3$ | $CH_3$ | |
| J-2 | — | H | H | $CH_2CH_2NO_2$ | $OC_2H_5$ | $N(CH_3)_2$ | |
| J-2 | — | H | H | $CH_2CH_2NO_2$ | $OC_2H_5$ | $NHCH_3$ | |

TABLE 2-continued

| | | | | GENERAL FORMULA 2 | | | |
|---|---|---|---|---|---|---|---|
| J | E | R | $R^1/R_2$ | Q | X | Y | m.p. °C. |
| J-2 | — | H | H | $(CH_2)_3NO_2$ | $OCH_3$ | $OCH_3$ | |
| J-2 | — | H | H | $(CH_2)_3NO_2$ | $OCH_3$ | $CH_3$ | |
| J-2 | $CH_2$ | H | H | $CH_2CH_2N_3$ | $OCH_3$ | $OCH_3$ | |
| J-2 | — | $CH_3$ | H | $CH_2CH_2N_3$ | $OCH_3$ | $OCH_3$ | |
| J-3 | | H | H | $CH_2CH_2N_3$ | $OCH_3$ | $OCH_3$ | |
| J-3 | | H | H | $CH_2CH_2N_3$ | $OCH_3$ | $CH_3$ | |
| J-3 | | H | H | $CH_2CH_2N_3$ | $OC_2H_5$ | $OC_2H_5$ | |
| J-3 | | H | H | $CH_2CH_2N_3$ | $OC_2N_5$ | $N(CH_3)_2$ | |
| J-3 | | H | H | $CH_2CH_2N_3$ | $OC_2H_5$ | $NHCH_3$ | |
| J-3 | | H | $CH_3$ | $CH_2CH_2N_3$ | $OCH_3$ | $OCH_3$ | |
| J-3 | | H | Cl | $CH_2CH_2N_3$ | $OCH_3$ | $OCH_3$ | |
| J-3 | | H | F | $CH_2CH_2N_3$ | $OCH_3$ | $OCH_3$ | |
| J-3 | | H | Br | $CH_2CH_2N_3$ | $OCH_3$ | $OCH_3$ | |
| J-3 | | H | $OCH_3$ | $CH_2CH_2N_3$ | $OCH_3$ | $OCH_3$ | |
| J-3 | | H | $SCH_3$ | $CH_2CH_2N_3$ | $OCH_3$ | $OCH_3$ | |
| J-3 | | H | $SO_2CH_3$ | $CH_2CH_2N_3$ | $OCH_3$ | $OCH_3$ | |
| J-3 | | H | H | $(CH_2)_3N_3$ | $OCH_3$ | $OCH_3$ | |
| J-3 | | H | H | $(CH_2)_3N_3$ | $OCH_3$ | $CH_3$ | |
| J-3 | | H | H | $CH_2CH_2SCN$ | $OCH_3$ | $OCH_3$ | |
| J-3 | | H | H | $CH_2CH_2SCN$ | $OC_2H_5$ | $OC_2H_5$ | |
| J-3 | | H | H | $CH_2CH_2SCN$ | $OCH_3$ | $CH_3$ | |
| J-3 | | H | H | $CH_2CH_2SCN$ | $OC_2H_5$ | $N(CH_3)_2$ | |
| J-3 | | H | H | $CH_2CH_2SCN$ | $OC_2H_5$ | $NHCH_3$ | |
| J-3 | | H | H | $(CH_2)_3SCN$ | $OCH_3$ | $OCH_3$ | |
| J-3 | | H | H | $(CH_2)_3SCN$ | $OCH_3$ | $CH_3$ | |
| J-3 | | H | H | $CH_2CH_2NO_2$ | $OCH_3$ | $OCH_3$ | |
| J-3 | | H | H | $CH_2CH_2NO_2$ | $OC_2H_5$ | $OC_3H_5$ | |
| J-3 | | H | H | $CH_2CH_2NO_2$ | $OCH_3$ | $CH_3$ | |
| J-3 | | H | H | $CH_2CH_2NO_2$ | $OC_2H_5$ | $N(CH_3)_2$ | |
| J-3 | | H | H | $CH_2CH_2NO_2$ | $OC_2H_5$ | $NHCH_3$ | |
| J-3 | | H | H | $(CH_2)_3NO_2$ | $OCH_3$ | $OCH_3$ | |
| J-3 | | H | H | $(CH_2)_3NO_2$ | $OCH_3$ | $CH_3$ | |
| J-3 | | $CH_3$ | H | $CH_2CH_2N_3$ | $OCH_3$ | $OCH_3$ | |
| J-4 | | H | H | $CH_2CH_2N_3$ | $OCH_3$ | $OCH_3$ | |
| J-4 | | H | H | $CH_2CH_2N_3$ | $OCH_3$ | $CH_3$ | |
| J-4 | | H | H | $CH_2CH_2N_3$ | $OC_2H_5$ | $OC_2H_5$ | |
| J-4 | | H | H | $CH_2CH_2N_3$ | $OC_2H_5$ | $N(CH_3)_2$ | |
| J-4 | | H | H | $CH_2CH_2N_3$ | $OC_2H_5$ | $NHCH_3$ | |
| J-4 | | H | $CH_3$ | $CH_2CH_2N_3$ | $OCH_3$ | $OCH_3$ | |
| J-4 | | H | Cl | $CH_2CH_2N_3$ | $OCH_3$ | $OCH_3$ | |
| J-4 | | H | F | $CH_2CH_2N_3$ | $OCH_3$ | $OCH_3$ | |
| J-4 | | H | Br | $CH_2CH_2N_3$ | $OCH_3$ | $OCH_3$ | |
| J-4 | | H | $OCH_3$ | $CH_2CH_2N_3$ | $OCH_3$ | $OCH_3$ | |
| J-4 | | H | $SCH_3$ | $CH_2CH_2N_3$ | $OCH_3$ | $OCH_3$ | |
| J-4 | | H | $SO_2CH_3$ | $CH_2CH_2N_3$ | $OCH_3$ | $OCH_3$ | |
| J-4 | | H | H | $(CH_2)_3N_3$ | $OCH_3$ | $OCH_3$ | |
| J-4 | | H | H | $(CH_2)_3N_3$ | $OCH_3$ | $CH_3$ | |
| J-4 | | H | H | $CH_2CH_2SCN$ | $OCH_3$ | $OCH_3$ | |
| J-4 | | H | H | $CH_2CH_2SCN$ | $OC_2H_5$ | $OC_2H_5$ | |
| J-4 | | H | H | $CH_2CH_2SCN$ | $OCH_3$ | $CH_3$ | |
| J-4 | | H | H | $CH_2CH_2SCN$ | $OC_2H_5$ | $N(CH_3)_2$ | |
| J-4 | | H | H | $CH_2CH_2SCN$ | $OC_2H_5$ | $NHCH_3$ | |
| J-4 | | H | H | $(CH_2)_3SCN$ | $OCH_3$ | $OCH_3$ | |
| J-4 | | H | H | $(CH_2)_3SCN$ | $OCH_3$ | $CH_3$ | |
| J-4 | | H | H | $CH_2CH_2NO_2$ | $OCH_3$ | $OCH_3$ | |
| J-4 | | H | H | $CH_2CH_2NO_2$ | $OC_2H_5$ | $OC_2H_5$ | |
| J-4 | | H | H | $CH_2CH_2NO_2$ | $OCH_3$ | $CH_3$ | |
| J-4 | | H | H | $CH_2CH_2NO_2$ | $OC_2H_5$ | $N(CH_3)_2$ | |
| J-4 | | H | H | $CH_2CH_2NO_2$ | $OC_2H_5$ | $NHCH_3$ | |
| J-4 | | H | H | $(CH_2)_3NO_2$ | $OCH_3$ | $OCH_3$ | |
| J-4 | | H | H | $(CH_2)_3NO_2$ | $OCH_3$ | $CH_3$ | |
| J-4 | | $CH_3$ | H | $CH_2CH_2N_3$ | $OCH_3$ | $OCH_3$ | |
| J-5 | | H | H | $CH_2CH_2N_3$ | $OCH_3$ | $OCH_3$ | |
| J-5 | | H | H | $CH_2CH_2N_3$ | $OC_2H_5$ | $OC_2H_5$ | |
| J-5 | | H | H | $CH_2CH_2N_3$ | $OCH_3$ | $CH_3$ | |
| J-5 | | H | H | $CH_2CH_2N_3$ | $OC_2H_5$ | $N(CH_3)_2$ | |
| J-5 | | H | H | $CH_2CH_2N_3$ | $OC_2H_5$ | $NHCH_3$ | |
| J-5 | | H | H | $CH_2CH_2N_3$ | $OCH_3$ | $N(CH_3)_2$ | |
| J-5 | | H | H | $CH_2CH_2SCN$ | $OCH_3$ | $OCH_3$ | |
| J-5 | | H | H | $CH_2CH_2SCN$ | $OCH_3$ | $CH_3$ | |
| J-5 | | H | H | $CH_2CH_2SCN$ | $OC_3$ | $OC_2H_5$ | |
| J-5 | | H | H | $CH_2CH_2SCN$ | $OC_2H_5$ | $NHCH_3$ | |
| J-5 | | H | H | $CH_2CH_2NO_2$ | $OCH_3$ | $OCH_3$ | |
| J-5 | | H | H | $CH_2CH_2NO_2$ | $OCH_3$ | $CH_3$ | |
| J-5 | | H | H | $CH_2CH_2NO_2$ | $OC_2H_5$ | $OC_2H_5$ | |
| J-5 | | H | H | $CH_2CH_2NO_2$ | $OC_2H_5$ | $NHCH_3$ | |
| J-6(n = 0) | — | H | H | $CH_2CH_2N_3$ | $OCH_3$ | $OCH_3$ | |
| J-6(n = 0) | — | H | H | $CH_2CH_2N_3$ | $OCH_3$ | $CH_3$ | |
| J-6(n = 0) | — | H | H | $CH_2CH_2N_3$ | $OC_2H_5$ | $OC_2H_5$ | |
| J-6(n = 0) | — | H | H | $CH_2CH_2N_3$ | $CH_3$ | $CH_3$ | |

TABLE 2-continued

GENERAL FORMULA 2

| J | E | R | R¹/R₂ | Q | X | Y | m.p. °C. |
|---|---|---|-------|---|---|---|----------|
| J-6(n = 0) | — | H | H | $CH_2CH_2N_3$ | $OC_2H_5$ | $N(CH_3)_2$ | |
| J-6(n = 0) | — | H | H | $CH_2CH_2N_3$ | $OC_2H_5$ | $NHCH_3$ | |
| J-6(n = 0) | — | H | H | $CH_2CH_2N_3$ | $OCH_3$ | $N(CH_3)_2$ | |
| J-6(n = 0) | — | H | H | $CH_2CH_2N_3$ | $OCH_2CF_3$ | $N(CH_3)_2$ | |
| J-6(n = 0) | — | H | 5-$CH_3$ | $CH_2CH_2N_3$ | $OCH_3$ | $OCH_3$ | |
| J-6(n = 0) | — | H | 5-$OCH_3$ | $CH_2CH_2N_3$ | $OCH_3$ | $OCH_3$ | |
| J-6(n = 0) | — | H | 5-Cl | $CH_2CH_2N_3$ | $OCH_3$ | $OCH_3$ | |
| J-6(n = 0) | — | H | 5-$CF_3$ | $CH_2CH_2N_3$ | $OCH_3$ | $OCH_3$ | |
| J-6(n = 0) | — | H | 4-$CH_3$ | $CH_2CH_2N_3$ | $OCH_3$ | $OCH_3$ | |
| J-6(n = 0) | — | H | 4-$OCH_3$ | $CH_2CH_2N_3$ | $OCH_3$ | $OCH_3$ | |
| J-6(n = 0) | — | H | 4-Cl | $CH_2CH_2N_3$ | $OCH_3$ | $OCH_3$ | |
| J-6(n = 0) | — | H | 4-$CF_3$ | $CH_2CH_2N_3$ | $OCH_3$ | $OCH_3$ | |
| J-6(n = 0) | — | H | 6-$CH_3$ | $CH_2CH_2N_3$ | $OCH_3$ | $OCH_3$ | |
| J-6(n = 0) | — | H | 6-$OCH_3$ | $CH_2CH_2N_3$ | $OCH_3$ | $OCH_3$ | |
| J-6(n = 0) | — | H | 6-Cl | $CH_2CH_2N_3$ | $OCH_3$ | $OCH_3$ | |
| J-6(n = 0) | — | H | 6-$CF_3$ | $CH_2CH_2N_3$ | $OCH_3$ | $OCH_3$ | |
| J-6(n = 0) | — | H | H | $(CH_2)_3N_3$ | $OCH_3$ | $OCH_3$ | |
| J-6(n = 0) | — | H | H | $(CH_2)_3N_3$ | $OCH_3$ | $CH_3$ | |
| J-6(n = 0) | — | H | H | $CH(CH_3)CH_2N_3$ | $OCH_3$ | $OCH_3$ | |
| J-6(n = 0) | — | H | H | $CH(CH_3)CH_2N_3$ | $OCH_3$ | $CH_3$ | |
| J-6(n = 0) | — | H | H | $CH_2CH_2SCN$ | $OCH_3$ | $OCH_3$ | |
| J-6(n = 0) | — | H | H | $CH_2CH_2SCN$ | $OC_2H_5$ | $OC_2H_5$ | |
| J-6(n = 0) | — | H | H | $CH_2CH_2SCN$ | $OCH_3$ | $CH$ | |
| J-6(n = 0) | — | H | H | $CH_2CH_2SCN$ | $OC_2H_5$ | $N(CH_3)_2$ | |
| J-6(n = 0) | — | H | H | $CH_2CH_2SCN$ | $OC_2H_5$ | $NHCH_3$ | |
| J-6(n = 0) | — | H | H | $(CH_2)_3SCN$ | $OCH_3$ | $OCH_3$ | |
| J-6(n = 0) | — | H | H | $(CH_2)_3SCN$ | $OCH_3$ | $CH_3$ | |
| J-6(n = 0) | — | H | H | $CH(CH_3)CH_2SCN$ | $OCH_3$ | $OCH_3$ | |
| J-6(n = 0) | — | H | H | $CH(CH_3)CH_2SCN$ | $OCH_3$ | $CH_3$ | |
| J-6(n = 0) | — | H | H | $CH_2CH_2NO_2$ | $OCH_3$ | $OCH_3$ | |
| J-6(n = 0) | — | H | H | $CH_2CH_2NO_2$ | $OC_2H_5$ | $OC_2H_5$ | |
| J-6(n = 0) | — | H | H | $CH_2CH_2NO_2$ | $OCH_3$ | $CH_3$ | |
| J-6(n = 0) | — | H | H | $CH_2CH_2NO_2$ | $OC_2H_5$ | $N(CH_3)_2$ | |
| J-6(n = 0) | — | H | H | $CH_2CH_2NO_2$ | $OC_2H_5$ | $NHCH_3$ | |
| J-6(n = 0) | — | H | H | $(CH_2)_3NO_2$ | $OCH_3$ | $OCH_3$ | |
| J-6(n = 0) | — | H | H | $(CH_2)_3NO_2$ | $OCH_3$ | $CH_3$ | |
| J-6(n = 0) | — | H | H | $CH(CH_3)CH_2NO_2$ | $OCH_3$ | $OCH_3$ | |
| J-6(n = 0) | — | H | H | $CH(CH_3)CH_2NO_2$ | $OCH_3$ | $CH_3$ | |
| J-6(n = 0) | $CH_2$ | H | H | $CH_2CH_2N_3$ | $OCH_3$ | $OCH_3$ | |
| J-6(n = 0) | $CH_2$ | H | H | $CH_2CH_2SCN$ | $OCH_3$ | $OCH_3$ | |
| J-6(n = 0) | $CH_2$ | H | H | $CH_2CH_2NO_2$ | $OCH_3$ | $OCH_3$ | |
| J-6(n = 0) | — | $CH_3$ | H | $CH_2CH_2NO_3$ | $OCH_3$ | $OCH_3$ | |
| J-6(n = 0) | — | $CH_3$ | H | $CH_2CH_2SCN$ | $OCH_3$ | $OCH_3$ | |
| J-6(n = 0) | — | $CH_3$ | H | $CH_2CH_2NO_2$ | $OCH_3$ | $OCH_3$ | |
| J-6(n = 1) | — | H | H | $CH_2CH_2N_3$ | $OCH_3$ | $OCH_3$ | |
| J-6(n = 1) | — | H | H | $CH_2CH_2SCN$ | $OCH_3$ | $OCH_3$ | |
| J-6(n = 1) | — | H | H | $CH_2CH_2NO_2$ | $OCH_3$ | $OCH_3$ | |
| J-7(n = 0) | — | H | H | $CH_2CH_2N_3$ | $OCH_3$ | $OCH_3$ | |
| J-7(n = 0) | — | H | H | $CH_2CH_2N_3$ | $OCH_3$ | $CH_3$ | |
| J-7(n = 0) | — | H | H | $CH_2CH_2N_3$ | $OC_2H_5$ | $OC_2H_5$ | |
| J-7(n = 0) | — | H | H | $CH_2CH_2N_3$ | $OC_2H_5$ | $NHCH_3$ | |
| J-7(n = 0) | — | H | 4-$CH_3$ | $CH_2CH_2N_3$ | $OCH_3$ | $OCH_3$ | |
| J-7(n = 0) | — | H | 4-Cl | $CH_2CH_2N_3$ | $OCH_3$ | $OCH_3$ | |
| J-7(n = 0) | — | H | 4-$CF_3$ | $CH_2CH_2N_3$ | $OCH_3$ | $OCH_3$ | |
| J-7(n = 0) | — | H | 4-$OCH_3$ | $CH_2CH_2N_3$ | $OCH_3$ | $OCH_3$ | |
| J-7(n = 0) | — | H | 4-$SCH_3$ | $CH_2CH_2N_3$ | $OCH_3$ | $OCH_3$ | |
| J-7(n = 0) | — | H | 4-$SO_2CH_3$ | $CH_2CH_2N_3$ | $OCH_3$ | $OCH_3$ | |
| J-7(n = 0) | — | H | 5-Cl | $CH_2CH_2N_3$ | $OCH_3$ | $OCH_3$ | |
| J-7(n = 0) | — | H | 6-$OCH_3$ | $CH_2CH_2N_3$ | $OCH_3$ | $OCH_3$ | |
| J-7(n = 0) | — | H | H | $(CH_2)_3N_3$ | $OCH_3$ | $CH_3$ | |
| J-7(n = 0) | — | H | H | $CH_2CH_2SCN$ | $OCH_3$ | $OCH_3$ | |
| J-7(n = 0) | — | H | H | $CH_2CH_2SCN$ | $OCH_3$ | $CH_3$ | |
| J-7(n = 0) | — | H | H | $CH_2CH_2SCN$ | $OC_2H_5$ | $OC_2H_5$ | |
| J-7(n = 0) | — | H | H | $CH_2CH_2SCN$ | $OC_2H_5$ | $NHCH_3$ | |
| J-7(n = 0) | — | H | H | $(CH_2)_3SCN$ | $OCH_3$ | $OCH_3$ | |
| J-7(n = 0) | — | H | H | $CH_2CH_2NO_2$ | $OCH_3$ | $OCH_3$ | |
| J-7(n = 0) | — | H | H | $CH_2CH_2NO_2$ | $OCH_3$ | $CH_3$ | |
| J-7(n = 0) | — | H | H | $CH_2CH_2NO_2$ | $OC_2H_5$ | $OC_2H_5$ | |
| J-7(n = 0) | — | H | H | $CH_2CH_2NO_2$ | $OC_2H_5$ | $NHCH_3$ | |
| J-7(n = 0) | — | H | H | $(CH_2)_3NO_2$ | $OCH_3$ | $OCH_3$ | |
| J-7(n = 0) | $CH_2$ | H | H | $CH_2CH_2N_3$ | $OCH_3$ | $OCH_3$ | |
| J-7(n = 0) | $CH_2$ | H | H | $CH_2CH_2SCN$ | $OCH_3$ | $OCH_3$ | |
| J-7(n = 0) | $CH_2$ | H | H | $CH_2CH_2NO_2$ | $OCH_3$ | $OCH_3$ | |
| J-7(n = 0) | — | $CH_3$ | H | $CH_2CH_2SCN$ | $OCH_3$ | $OCH_3$ | |
| J-7(n = 0) | — | $CH_3$ | H | $CH_2CH_2N_3$ | $OCH_3$ | $OCH_3$ | |
| J-7(n = 0) | — | $CH_3$ | H | $CH_2CH_2NO_2$ | $OCH_3$ | $OCH_3$ | |
| J-7(n = 1) | — | H | H | $CH_2CH_2N_3$ | $OCH_3$ | $OCH_3$ | |
| J-7(n = 1) | — | H | H | $CH_2CH_2SCN$ | $OCH_3$ | $OCH_3$ | |
| J-7(n = 1) | — | H | H | $CH_2CH_2NO_2$ | $OCH_3$ | $OCH_3$ | |
| J-8(n = 0) | — | H | H | $CH_2CH_2N_3$ | $OCH_3$ | $OCH_3$ | |

TABLE 2-continued

GENERAL FORMULA 2

| J | E | R | R¹/R² | Q | X | Y | m.p. °C. |
|---|---|---|---|---|---|---|---|
| J-8(n = 0) | — | H | H | $CH_2CH_2N_3$ | $OCH_3$ | $CH_3$ | |
| J-8(n = 0) | — | H | H | $CH_2CH_2N_3$ | $OC_2H_5$ | $OC_2H_5$ | |
| J-8(n = 0) | — | H | H | $CH_2CH_2N_3$ | $OC_2H_5$ | $NHCH_3$ | |
| J-8(n = 0) | — | H | 2-$CH_3$ | $CH_2CH_2N_3$ | $OCH_3$ | $OCH_3$ | |
| J-8(n = 0) | — | H | 2-Cl | $CH_2CH_2N_3$ | $OCH_3$ | $OCH_3$ | |
| J-8(n = 0) | — | H | 2-$CF_3$ | $CH_2CH_2N_3$ | $OCH_3$ | $OCH_3$ | |
| J-8(n = 0) | — | H | 2-$OCH_3$ | $CH_2CH_2N_3$ | $OCH_3$ | $OCH_3$ | |
| J-8(n = 0) | — | H | 2-$SCH_3$ | $CH_2CH_2N_3$ | $OCH_3$ | $OCH_3$ | |
| J-8(n = 0) | — | H | 2-$SO_2CH_3$ | $CH_2CH_2N_3$ | $OCH_3$ | $OCH_3$ | |
| J-8(n = 0) | — | H | 5-$CH_3$ | $CH_2CH_2N_3$ | $OCH_3$ | $OCH_3$ | |
| J-8(n = 0) | — | H | 5-Cl | $CH_2CH_2N_3$ | $OCH_3$ | $OCH_3$ | |
| J-8(n = 0) | — | H | 5-$CF_3$ | $CH_2CH_2N_3$ | $OCH_3$ | $OCH_3$ | |
| J-8(n = 0) | — | H | 5-$OCH_3$ | $CH_2CH_2N_3$ | $OCH_3$ | $OCH_3$ | |
| J-8(n = 0) | — | H | 5-$SCH_3$ | $CH_2CH_2N_3$ | $OCH_3$ | $OCH_3$ | |
| J-8(n = 0) | — | H | 5-$SO_2CH_3$ | $CH_2CH_2N_3$ | $OCH_3$ | $OCH_3$ | |
| J-8(n = 0) | — | H | 6-$OCH_3$ | $CH_2CH_2N_3$ | $OCH_3$ | $OCH_3$ | |
| J-8(n = 0) | — | H | H | $(CH_2)_3N_3$ | $OCH_3$ | $OCH_3$ | |
| J-8(n = 0) | — | H | H | $CH_2CH_2SCN$ | $OCH_3$ | $OCH_3$ | |
| J-8(n = 0) | — | H | H | $CH_2CH_2SCN$ | $OCH_3$ | $CH_3$ | |
| J-8(n = 0) | — | H | H | $CH_2CH_2SCN$ | $OC_2H_5$ | $OC_2H_5$ | |
| J-8(n = 0) | — | H | H | $CH_2CH_2SCN$ | $OC_2H_5$ | $NHCH_3$ | |
| J-8(n = 0) | — | H | H | $(CH_2)_3SCN$ | $OCH_3$ | $OCH_3$ | |
| J-8(n = 0) | — | H | H | $CH_2CH_2NO_2$ | $OCH_3$ | $OCH_3$ | |
| J-8(n = 0) | — | H | H | $CH_2CH_2NO_2$ | $OCH_3$ | $CH_3$ | |
| J-8(n = 0) | — | H | H | $CH_2CH_2NO_2$ | $OC_2H_5$ | $OC_2H_5$ | |
| J-8(n = 0) | — | H | H | $CH_2CH_2NO_2$ | $OC_2H_5$ | $NHCH_3$ | |
| J-8(n = 0) | — | H | H | $(CH_2)_3NO_2$ | $OCH_3$ | $OCH_3$ | |
| J-8(n = 0) | $CH_2$ | H | H | $CH_2CH_2N_3$ | $OCH_3$ | $OCH_3$ | |
| J-8(n = 0) | $CH_2$ | H | H | $CH_2CH_2SCN$ | $OCH_3$ | $OCH_3$ | |
| J-8(n = 0) | $CH_2$ | H | H | $CH_2CH_2NO_2$ | $OCH_3$ | $OCH_3$ | |
| J-8(n = 0) | — | $CH_3$ | H | $CH_2CH_2N_3$ | $OCH_3$ | $OCH_3$ | |
| J-8(n = 0) | — | $CH_3$ | H | $CH_2CH_2SCN$ | $OCH_3$ | $OCH_3$ | |
| J-8(n = 0) | — | $CH_3$ | H | $CH_2CH_2NO_2$ | $OCH_3$ | $OCH_3$ | |
| J-8(n = 1) | — | H | H | $CH_2CH_2N_3$ | $OCH_3$ | $OCH_3$ | |
| J-8(n = 1) | — | H | H | $CH_2CH_2SCN$ | $OCH_3$ | $OCH_3$ | |
| J-8(n = 1) | — | H | H | $CH_2CH_2NO_2$ | $OCH_3$ | $OCH_3$ | |
| J-9(R³ = H) | | H | H | $CH_2CH_2N_3$ | $OCH_3$ | $OCH_3$ | |
| J-9(R³ = H) | | H | H | $CH_2CH_2N_3$ | $OCH_3$ | $CH_3$ | |
| J-9(R³ = H) | | H | H | $CH_2CH_2N_3$ | $OC_2H_5$ | $OC_2H_5$ | |
| J-9(R³ = H) | | H | H | $CH_2CH_2N_3$ | $OC_2H_5$ | $NHCH_3$ | |
| J-9(R³ = $CH_3$) | | H | H | $CH_2CH_2N_3$ | $OCH_3$ | $OCH_3$ | |
| J-9(R³ = $CH_3$) | | H | H | $CH_2CH_2N_3$ | $OCH_3$ | $CH_3$ | |
| J-9(R³ = $CH_3$) | | H | H | $CH_2CH_2N_3$ | $OC_2H_5$ | $OC_2H_5$ | |
| J-9(R³ = $CH_3$) | | H | H | $CH_2CH_2N_3$ | $OC_2H_5$ | $NHCH_3$ | |
| J-9(R³ = $CH_3$) | | H | Cl | $CH_2CH_2N_3$ | $OCH_3$ | $OCH_3$ | |
| J-9(R³ = $CH_3$) | | H | $CH_3$ | $CH_2CH_2N_3$ | $OCH_3$ | $OCH_3$ | |
| J-9(R³ = $CH_3$) | | H | H | $(CH_2)_3N_3$ | $OCH_3$ | $OCH_3$ | |
| J-9(R³ = $CH_3$) | | H | H | $CH_2CH_2SCN$ | $OCH_3$ | $OCH_3$ | |
| J-9(R³ = $CH_3$) | | H | H | $CH_2CH_2SCN$ | $OCH_3$ | $CH_3$ | |
| J-9(R³ = $CH_3$) | | H | H | $CH_2CH_2SCN$ | $OC_2H_5$ | $OC_2H_5$ | |
| J-9(R³ = $CH_3$) | | H | H | $CH_2CH_2SCN$ | $OC_2H_5$ | $NHCH_3$ | |
| J-9(R³ = $CH_3$) | | H | H | $(CH_2)_3SCN$ | $OCH_3$ | $OCH_3$ | |
| J-9(R³ = $CH_3$) | | H | H | $CH_2CH_2NO_2$ | $OCH_3$ | $OCH_3$ | |
| J-9(R³ = $CH_3$) | | H | H | $CH_2CH_2NO_2$ | $OCH_3$ | $CH_3$ | |
| J-9(R³ = $CH_3$) | | H | H | $CH_2CH_2NO_2$ | $OC_2H_5$ | $OC_2H_5$ | |
| J-9(R³ = $CH_3$) | | H | H | $CH_2CH_2NO_2$ | $OC_2H_5$ | $NHCH_3$ | |
| J-9(R³ = $CH_3$) | | H | H | $(CH_2)_3NO_2$ | $OCH_3$ | $OCH_3$ | |
| J-9(R³ = $CH_3$) | $CH_3$ | H | H | $CH_2CH_2N_3$ | $OCH_3$ | $OCH_3$ | |
| J-9(R³ = $CH_3$) | $CH_3$ | H | H | $CH_2CH_2SCN$ | $OCH_3$ | $OCH_3$ | |
| J-9(R³ = $CH_3$) | $CH_3$ | H | H | $CH_2CH_2NO_2$ | $OCH_3$ | $OCH_3$ | |
| J-9(R³ = H) | | H | H | $CH_2CH_2SCN$ | $OCH_3$ | $OCH_3$ | |
| J-9(R³ = H) | | H | H | $CH_2CH_2NO_2$ | $OCH_3$ | $OCH_3$ | |
| J-10(R³ = H) | | H | H | $CH_2CH_2N_3$ | $OCH_3$ | $OCH_3$ | |
| J-10(R³ = H) | | H | H | $CH_2CH_2N_3$ | $OCH_3$ | $CH_3$ | |
| J-10(R³ = H) | | H | H | $CH_2CH_2N_3$ | $OC_2H_5$ | $OC_2H_5$ | |
| J-10(R³ = H) | | H | H | $CH_2CH_2N_3$ | $OC_2H_5$ | $NHCH_3$ | |
| J-10(R³ = $CH_3$) | | H | H | $CH_2CH_2N_3$ | $OCH_3$ | $OCH_3$ | |
| J-10(R³ = $CH_3$) | | H | H | $CH_2CH_2N_3$ | $OCH_3$ | $CH_3$ | |
| J-10(R³ = $CH_3$) | | H | H | $CH_2CH_2N_3$ | $OC_2H_5$ | $OC_2H_5$ | |
| J-10(R³ = $CH_3$) | | H | H | $CH_2CH_2N_3$ | $OC_2H_5$ | $NHCH_3$ | |
| J-10(R³ = $CH_3$) | | H | Cl | $CH_2CH_2N_3$ | $OCH_3$ | $OCH_3$ | |
| J-10(R³ = $CH_3$) | | H | $CH_3$ | $CH_2CH_2N_3$ | $OCH_3$ | $OCH_3$ | |
| J-10(R³ = $CH_3$) | | H | H | $(CH_2)_3N_3$ | $OCH_3$ | $OCH_3$ | |
| J-10(R³ = $CH_3$) | | H | H | $CH_2CH_2SCN$ | $OCH_3$ | $OCH_3$ | |
| J-10(R³ = $CH_3$) | | H | H | $CH_2CH_2SCN$ | $OCH_3$ | $CH_3$ | |
| J-10(R³ = $CH_3$) | | H | H | $CH_2CH_2SCN$ | $OC_2H_5$ | $OC_2H_5$ | |
| J-10(R³ = $CH_3$) | | H | H | $CH_2CH_2SCN$ | $OC_2H_5$ | $NHCH_3$ | |
| J-10(R³ = $CH_3$) | | H | H | $(CH_2)_3SCN$ | $OCH_3$ | $OCH_3$ | |
| J-10(R³ = $CH_3$) | | H | H | $CH_2CH_2NO_2$ | $OCH_3$ | $OCH_3$ | |
| J-10(R³ = $CH_3$) | | H | H | $CH_2CH_2NO_2$ | $OCH_3$ | $CH_3$ | |

TABLE 2-continued

GENERAL FORMULA 2

| J | E | R | R¹/R² | Q | X | Y | m.p. °C. |
|---|---|---|---|---|---|---|---|
| J-10(R³ = CH₃) | | H | H | CH₂CH₂NO₂ | OC₂H₅ | OC₂H₅ | |
| J-10(R³ = CH₃) | | H | H | CH₂CH₂NO₂ | OC₂H₅ | NHCH₃ | |
| J-10(R³ = CH₃) | | H | H | (CH₂)₃NO₂ | OCH₃ | OCH₃ | |
| J-10(R³ = CH₃) | | CH₃ | H | CH₂CH₂N₃ | OCH₃ | OCH₃ | |
| J-10(R³ = CH₃) | | CH₃ | H | CH₂CH₂SCN | OCH₃ | OCH₃ | |
| J-10(R³ = CH₃) | | CH₃ | H | CH₂CH₂NO₂ | OCH₃ | OCH₃ | |
| J-10(R³ = H) | | H | H | CH₂CH₂SCN | OCH₃ | OCH₃ | |
| J-10(R³ = H) | | H | H | CH₂CH₂NO₂ | OCH₃ | OCH₃ | |
| J-11(R³ = H) | | H | H | CH₂CH₂N₃ | OCH₃ | OCH₃ | |
| J-11(R³ = H) | | H | H | CH₂CH₂N₃ | OCH₃ | CH₃ | |
| J-11(R³ = H) | | H | H | CH₂CH₂N₃ | OC₂H₅ | OC₂H₅ | |
| J-11(R³ = H) | | H | H | CH₂CH₂N₃ | OC₂H₅ | NHCH₃ | |
| J-11(R³ = CH₃) | | H | H | CH₂CH₂N₃ | OCH₃ | OCH₃ | |
| J-11(R³ = CH₃) | | H | H | CH₂CH₂N₃ | OCH₃ | CH₃ | |
| J-11(R³ = CH₃) | | H | H | CH₂CH₂N₃ | OC₂H₅ | OC₂H₅ | |
| J-11(R³ = CH₃) | | H | H | CH₂CH₂N₃ | OC₂H₅ | NHCH₃ | |
| J-11(R³ = C₆H₅) | | H | H | CH₂CH₂N₃ | OCH₃ | OCH₃ | |
| J-11(R³ = CH₂CH=CH₂) | | H | H | CH₂CH₂N₃ | OCH₃ | OCH₃ | |
| J-11(R³ = CH₂CN) | | H | H | CH₂CH₂N₃ | OCH₃ | OCH₃ | |
| J-11(R³ = CH₃) | | H | Cl | CH₂CH₂N₃ | OCH₃ | OCH₃ | |
| J-11(R³ = CH₃) | | H | CH₃ | CH₂CH₂N₃ | OCH₃ | OCH₃ | |
| J-11(R³ = CH₃) | | H | H | (CH₂)₃N₃ | OCH₃ | OCH₃ | |
| J-11(R³ = CH₃) | | H | H | CH₂CH₂SCN | OCH₃ | OCH₃ | |
| J-11(R³ = CH₃) | | H | H | CH₂CH₂SCN | OCH₃ | CH₃ | |
| J-11(R³ = CH₃) | | H | H | CH₂CH₂SCN | OC₂H₅ | OC₂H₅ | |
| J-11(R³ = CH₃) | | H | H | CH₂CH₂SCN | OC₂H₅ | NHCH₃ | |
| J-11(R³ = CH₃) | | H | H | (CH₂)₃SCN | OCH₃ | OCH₃ | |
| J-11(R³ = CH₃) | | H | H | CH₂CH₂NO₂ | OCH₃ | OCH₃ | |
| J-11(R³ = CH₃) | | H | H | CH₂CH₂NO₂ | OCH₃ | CH₃ | |
| J-11(R³ = CH₃) | | H | H | CH₂CH₂NO₂ | OC₂H₅ | OC₂H₅ | |
| J-11(R³ = CH₃) | | H | H | CH₂CH₂NO₂ | OC₂H₅ | NHCH₃ | |
| J-11(R³ = CH₃) | | H | H | (CH₂)₃NO₂ | OCH₃ | OCH₃ | |
| J-11(R³ = CH₃) | | CH₃ | H | CH₂CH₂N₃ | OCH₃ | OCH₃ | |
| J-11(R³ = CH₃) | | CH₃ | H | CH₂CH₂SCN | OCH₃ | OCH₃ | |
| J-11(R³ = CH₃) | | CH₃ | H | CH₂CH₂NO₂ | OCH₃ | OCH₃ | |
| J-11(R³ = H) | | H | H | CH₂CH₂SCN | OCH₃ | OCH₃ | |
| J-11(R³ = H) | | H | H | CH₂CH₂NO₂ | OCH₃ | OCH₃ | |
| J-12(R³ = H) | | H | H | CH₂CH₂N₃ | OCH₃ | OCH₃ | |
| J-12(R³ = H) | | H | H | CH₂CH₂N₃ | OCH₃ | CH₃ | |
| J-12(R³ = H) | | H | H | CH₂CH₂N₃ | OC₂H₅ | OC₂H₅ | |
| J-12(R³ = H) | | H | H | CH₂CH₂N₃ | OC₂H₅ | NHCH₃ | |
| J-12(R³ = CH₃) | | H | H | CH₂CH₂N₃ | OCH₃ | OCH₃ | |
| J-12(R³ = CH₃) | | H | H | CH₂CH₂N₃ | OCH₃ | CH₃ | |
| J-12(R³ = CH₃) | | H | H | CH₂CH₂N₃ | OC₂H₅ | OC₂H₅ | |
| J-12(R³ = CH₃) | | H | H | CH₂CH₂N₃ | OC₂H₅ | NHCH₃ | |
| J-12(R³ = CH₃) | | H | Cl | CH₂CH₂N₃ | OCH₃ | OCH₃ | |
| J-12(R³ = CH₃) | | H | CH₃ | CH₂CH₂N₃ | OCH₃ | OCH₃ | |
| J-12(R³ = CH₃) | | H | H | (CH₂)₃N₃ | OCH₃ | OCH₃ | |
| J-12(R³ = CH₃) | | H | H | CH₂CH₂SCN | OCH₃ | OCH₃ | |
| J-12(R³ = CH₃) | | H | H | CH₂CH₂SCN | OCH₃ | CH₃ | |
| J-12(R³ = CH₃) | | H | H | CH₂CH₂SCN | OC₂H₅ | OC₂H₅ | |
| J-12(R³ = CH₃) | | H | H | CH₂CH₂SCN | OC₂H₅ | NHCH₃ | |
| J-12(R³ = CH₃) | | H | H | (CH₂)₃SCN | OCH₃ | OCH₃ | |
| J-12(R³ = CH₃) | | H | H | CH₂CH₂NO₂ | OCH₃ | OCH₃ | |
| J-12(R³ = CH₃) | | H | H | CH₂CH₂NO₂ | OCH₃ | CH₃ | |
| J-12(R³ = CH₃) | | H | H | CH₂CH₂NO₂ | OC₂H₅ | OC₂H₅ | |
| J-12(R³ = CH₃) | | H | H | CH₂CH₂NO₃ | OC₂H₅ | NHCH₃ | |
| J-12(R³ = CH₃) | | H | H | (CH₂)₃NO₂ | OCH₃ | OCH₃ | |
| J-12(R³ = CH₃) | | CH₃ | H | CH₂CH₂N₃ | OCH₃ | OCH₃ | |
| J-12(R³ = CH₃) | | CH₃ | H | CH₂CH₂SCN | OCH₃ | OCH₃ | |
| J-12(R³ = CH₃) | | CH₃ | H | CH₂CH₂NO₂ | OCH₃ | OCH₃ | |
| J-12(R³ = H) | | H | H | CH₂CH₂SCN | OCH₃ | OCH₃ | |
| J-12(R³ = H) | | H | H | CH₂CH₂NO₂ | OCH₃ | OCH₃ | |

TABLE 3

GENERAL FORMULA 3

| J | E | R | R¹/R² | Q | X₁ | Y₁ | m.p. °C. |
|---|---|---|---|---|---|---|---|
| J-1 | — | H | H | CH₂CH₂N₃ | CH₃ | O | |
| J-1 | — | H | H | CH₂CH₂N₃ | OCH₃ | O | |
| J-1 | — | H | H | CH₂CH₂N₃ | OC₂H₅ | O | |
| J-1 | — | H | H | CH₂CH₂N₃ | OCF₂H | O | |
| J-1 | — | H | H | CH₂CH₂N₃ | CH₃ | CH₂ | |
| J-1 | — | H | H | CH₂CH₂N₃ | OCH₃ | CH₂ | |
| J-1 | — | CH₃ | H | CH₂CH₂N₃ | CH₃ | O | |
| J-1 | — | H | 5-Cl | CH₂CH₂N₃ | CH₃ | O | |
| J-1 | — | H | 5-OCH₃ | CH₂CH₂N₃ | CH₃ | O | |

TABLE 3-continued

GENERAL FORMULA 3

| J | E | R | R¹/R² | Q | $X_1$ | $Y_1$ | m.p. °C. |
|---|---|---|---|---|---|---|---|
| J-1 | — | H | 5-CH$_3$ | CH$_2$CH$_2$N$_3$ | CH$_3$ | O | |
| J-1 | — | H | 3-Cl | CH$_2$CH$_2$N$_3$ | CH$_3$ | O | |
| J-1 | — | H | H | CH(CH$_3$)CH$_2$N$_3$ | CH$_3$ | O | |
| J-1 | — | H | H | (CH$_2$)$_3$N$_3$ | CH$_3$ | O | |
| J-1 | — | H | H | CH$_2$CH$_2$SCN | CH$_3$ | O | |
| J-1 | — | H | H | CH(CH$_3$)CH$_2$SCN | CH$_3$ | O | |
| J-1 | — | H | H | (CH$_2$)$_3$SCN | CH$_3$ | O | |
| J-1 | — | H | H | CH$_2$CH$_2$NO$_2$ | CH$_3$ | O | |
| J-1 | — | H | H | CH(CH$_3$)CH$_2$NO$_2$ | CH$_3$ | O | |
| J-1 | — | H | H | (CH$_2$)$_3$NO$_2$ | CH$_3$ | O | |
| J-2 | — | H | H | CH$_2$CH$_2$N$_3$ | CH$_3$ | O | |
| J-2 | — | H | H | CH$_2$CH$_2$SCN | CH$_3$ | O | |
| J-2 | — | H | H | CH$_2$CH$_2$NO$_2$ | CH$_3$ | O | |
| J-3 | | H | H | CH$_2$CH$_2$N$_3$ | CH$_3$ | O | |
| J-3 | | H | H | CH$_2$CH$_2$SCN | CH$_3$ | O | |
| J-3 | | H | H | CH$_2$CH$_2$NO$_2$ | CH$_3$ | O | |
| J-4 | | H | H | CH$_2$CH$_2$N$_3$ | CH$_3$ | O | |
| J-4 | | H | H | CH$_2$CH$_2$SCN | CH$_3$ | O | |
| J-4 | | H | H | CH$_2$CH$_2$NO$_2$ | CH$_3$ | O | |
| J-5 | | H | H | CH$_2$CH$_2$N$_3$ | CH$_3$ | O | |
| J-5 | | H | H | CH$_2$CH$_2$SCN | CH$_3$ | O | |
| J-5 | | H | H | CH$_2$CH$_2$NO$_2$ | CH$_3$ | O | |
| J-6(n = 0) | — | H | H | CH$_2$CH$_2$N$_3$ | CH$_3$ | O | |
| J-6(n = 0) | — | H | H | CH$_2$CH$_2$SCN | CH$_3$ | O | |
| J-6(n = 0) | — | H | H | CH$_2$CH$_2$NO$_2$ | CH$_3$ | O | |
| J-7(n = 0) | — | H | H | CH$_2$CH$_2$N$_3$ | CH$_3$ | O | |
| J-7(n = 0) | — | H | H | CH$_2$CH$_2$SCN | CH$_3$ | O | |
| J-7(n = 0) | — | H | H | CH$_2$CH$_2$NO$_2$ | CH$_3$ | O | |
| J-8(n = 0) | — | H | H | CH$_2$CH$_2$N$_3$ | CH$_3$ | O | |
| J-8(n = 0) | — | H | H | CH$_2$CH$_2$SCN | CH$_3$ | O | |
| J-8(n = 0) | — | H | H | CH$_2$CH$_2$NO$_2$ | CH$_3$ | O | |
| J-9(R$^3$ = CH$_3$) | | H | H | CH$_2$CH$_2$N$_3$ | CH$_3$ | O | |
| J-9(R$^3$ = CH$_3$) | | H | H | CH$_2$CH$_2$SCN | CH$_3$ | O | |
| J-9(R$^3$ = CH$_3$) | | H | H | CH$_2$CH$_2$NO$_2$ | CH$_3$ | O | |
| J-10(R$^3$ = CH$_3$) | | H | H | CH$_2$CH$_2$N$_3$ | CH$_3$ | O | |
| J-10(R$^3$ = CH$_3$) | | H | H | CH$_2$CH$_2$SCN | CH$_3$ | O | |
| J-10(R$^3$ = CH$_3$) | | H | H | CH$_2$CH$_2$NO$_2$ | CH$_3$ | O | |
| J-11(R$^3$ = CH$_3$) | | H | H | CH$_2$CH$_2$N$_3$ | CH$_3$ | O | |
| J-11(R$^3$ = CH$_3$) | | H | H | CH$_2$CH$_2$SCN | CH$_3$ | O | |
| J-11(R$^3$ = CH$_3$) | | H | H | CH$_2$CH$_2$NO$_2$ | CH$_3$ | O | |
| J-12(R$^3$ = CH$_3$) | | H | H | CH$_2$CH$_2$N$_3$ | CH$_3$ | O | |
| J-12(R$^3$ = CH$_3$) | | H | H | CH$_2$CH$_2$SCN | CH$_3$ | O | |
| J-12(R$^3$ = CH$_3$) | | H | H | CH$_2$CH$_2$NO$_2$ | CH$_3$ | O | |

TABLE 4

GENERAL FORMULA 4

| J | E | R | R¹/R² | Q | $X_1$ | m.p. °C. |
|---|---|---|---|---|---|---|
| J-1 | — | H | H | CH$_2$CH$_2$N$_3$ | CH$_3$ | |
| J-1 | — | H | H | CH$_2$CH$_2$N$_3$ | OCH$_3$ | |
| J-1 | — | H | H | CH$_2$CH$_2$N$_3$ | OC$_2$H$_5$ | |
| J-1 | — | H | H | CH$_2$CH$_2$N$_3$ | OCF$_2$H | |
| J-1 | — | H | H | CH$_2$CH$_2$N$_3$ | CH$_3$ | |
| J-1 | — | H | H | CH$_2$CH$_2$N$_3$ | OCH$_3$ | |
| J-1 | — | CH$_3$ | H | CH$_2$CH$_2$N$_3$ | CH$_3$ | |
| J-1 | — | H | 5-Cl | CH$_2$CH$_2$N$_3$ | CH$_3$ | |
| J-1 | — | H | 5-OCH$_3$ | CH$_2$CH$_2$N$_3$ | CH$_3$ | |
| J-1 | — | H | 5-CH$_3$ | CH$_2$CH$_2$N$_3$ | CH$_3$ | |
| J-1 | — | H | 3-Cl | CH$_2$CH$_2$N$_3$ | CH$_3$ | |
| J-1 | — | H | H | CH(CH$_3$)CH$_2$N$_3$ | CH$_3$ | |
| J-1 | — | H | H | (CH$_2$)$_3$N$_3$ | CH$_3$ | |
| J-1 | — | H | H | CH$_2$CH$_2$SCN | CH$_3$ | |
| J-1 | — | H | H | CH$_2$CH$_2$SCN | OCH$_3$ | |
| J-1 | — | H | H | CH(CH$_3$)CH$_2$SCN | CH$_3$ | |
| J-1 | — | H | H | (CH$_2$)$_3$SCN | CH$_3$ | |
| J-1 | — | H | H | CH$_2$CH$_2$NO$_2$ | CH$_3$ | |
| J-1 | — | H | H | CH(CH$_3$)CH$_2$NO$_2$ | CH$_3$ | |
| J-1 | — | H | H | (CH$_2$)$_3$NO$_2$ | CH$_3$ | |
| J-2 | — | H | H | CH$_2$CH$_2$N$_3$ | CH$_3$ | |
| J-2 | — | H | H | CH$_2$CH$_2$SCN | CH$_3$ | |
| J-2 | — | H | H | CH$_2$CH$_2$NO$_2$ | CH$_3$ | |
| J-3 | | H | H | CH$_2$CH$_2$N$_3$ | OCH$_3$ | |
| J-3 | | H | H | CH$_2$CH$_2$N$_3$ | CH$_3$ | |
| J-3 | | H | H | CH$_2$CH$_2$SCN | OCH$_3$ | |
| J-3 | | H | H | CH$_2$CH$_2$SCN | CH$_3$ | |
| J-3 | | H | H | CH$_2$CH$_2$NO$_2$ | OCH$_3$ | |
| J-3 | | H | H | CH$_2$CH$_2$NO$_2$ | CH$_3$ | |
| J-4 | | H | H | CH$_2$CH$_2$N$_3$ | CH$_3$ | |

TABLE 4-continued

GENERAL FORMULA 4

| J | E | R | R¹/R² | Q | X₁ | m.p. °C. |
|---|---|---|---|---|---|---|
| J-4 | | H | H | $CH_2CH_2SCN$ | $CH_3$ | |
| J-4 | | H | H | $CH_2CH_2NO_2$ | $CH_3$ | |
| J-5 | | H | H | $CH_2CH_2N_3$ | $CH_3$ | |
| J-5 | | H | H | $CH_2CH_2SCN$ | $CH_3$ | |
| J-5 | | H | H | $CH_2CH_2NO_2$ | $CH_3$ | |
| J-6(n = 0) | — | H | H | $CH_2CH_2N_3$ | $CH_3$ | |
| J-6(n = 0) | — | H | H | $CH_2CH_2SCN$ | $CH_3$ | |
| J-6(n = 0) | — | H | H | $CH_2CH_2NO_2$ | $CH_3$ | |
| J-7(n = 0) | — | H | H | $CH_2CH_2N_3$ | $OCH_3$ | |
| J-7(n = 0) | — | H | H | $CH_2CH_2N_3$ | $CH_3$ | |
| J-7(n = 0) | — | H | H | $CH_2CH_2SCN$ | $OCH_3$ | |
| J-7(n = 0) | — | H | H | $CH_2CH_2SCN$ | $CH_3$ | |
| J-7(n = 0) | — | H | H | $CH_2CH_2NO_2$ | $OCH_3$ | |
| J-7(n = 0) | — | H | H | $CH_2CH_2NO_2$ | $CH_3$ | |
| J-8(n = 0) | — | H | H | $CH_2CH_2N_3$ | $CH_3$ | |
| J-8(n = 0) | — | H | H | $CH_2CH_2SCN$ | $CH_3$ | |
| J-8(n = 0) | — | H | H | $CH_2CH_2NO_2$ | $CH_3$ | |
| J-9($R^3$ = $CH_3$) | | H | H | $CH_2CH_2N_3$ | $CH_3$ | |
| J-9($R^3$ = $CH_3$) | | H | H | $CH_2CH_2SCN$ | $CH_3$ | |
| J-9($R^3$ = $CH_3$) | | H | H | $CH_2CH_2NO_2$ | $CH_3$ | |
| J-10($R^3$ = $CH_3$) | | H | H | $CH_2CH_2N_3$ | $CH_3$ | |
| J-10($R^3$ = $CH_3$) | | H | H | $CH_2CH_2SCN$ | $CH_3$ | |
| J-10($R^3$ = $CH_3$) | | H | H | $CH_2CH_2NO_2$ | $CH_3$ | |
| J-11($R^3$ = $CH_3$) | | H | H | $CH_2CH_2N_3$ | $CH_3$ | |
| J-11($R^3$ = $CH_3$) | | H | H | $CH_2CH_2SCN$ | $CH_3$ | |
| J-11($R^3$ = $CH_3$) | | H | H | $CH_2CH_2NO_2$ | $CH_3$ | |
| J-12($R^3$ = $CH_3$) | | H | H | $CH_2CH_2N_3$ | $CH_3$ | |
| J-12($R^3$ = $CH_3$) | | H | H | $CH_2CH_2SCN$ | $CH_3$ | |
| J-12($R^3$ = $CH_3$) | | H | H | $CH_2CH_2NO_2$ | $CH_3$ | |

TABLE 5

GENERAL FORMULA 5

| J | E | R | R¹/R² | Q | X₁ | Y₃ | m.p. °C. |
|---|---|---|---|---|---|---|---|
| J-1 | — | H | H | $CH_2CH_2N_3$ | $CH_3$ | $CH_3$ | |
| J-1 | — | H | H | $CH_2CH_2N_3$ | $OCH_3$ | $CH_3$ | |
| J-1 | — | H | H | $CH_2CH_2N_3$ | $OC_2H_5$ | $CH_3$ | |
| J-1 | — | H | H | $CH_2CH_2N_3$ | $OCF_2H$ | $CH_3$ | |
| J-1 | — | H | H | $CH_2CH_2N_3$ | $CH_3$ | H | |
| J-1 | — | H | H | $CH_2CH_2N_3$ | $OCH_3$ | H | |
| J-1 | — | $CH_3$ | H | $CH_2CH_2N_3$ | $CH_3$ | $CH_3$ | |
| J-1 | — | H | 5-Cl | $CH_2CH_2N_3$ | $CH_3$ | $CH_3$ | |
| J-1 | — | H | 5-$OCH_3$ | $CH_2CH_2N_3$ | $CH_3$ | $CH_3$ | |
| J-1 | — | H | 5-$CH_3$ | $CH_2CH_2N_3$ | $CH_3$ | $CH_3$ | |
| J-1 | — | H | 3-Cl | $CH_2CH_2N_3$ | $CH_3$ | $CH_3$ | |
| J-1 | — | H | H | $CH(CH_3)CH_2N_3$ | $CH_3$ | $CH_3$ | |
| J-1 | — | H | H | $(CH_2)_3N_3$ | $CH_3$ | $CH_3$ | |
| J-1 | — | H | H | $CH_2CH_2SCN$ | $CH_3$ | $CH_3$ | |
| J-1 | — | H | H | $CH(CH_3)CH_2SCN$ | $CH_3$ | $CH_3$ | |
| J-1 | — | H | H | $(CH_2)_3SCN$ | $CH_3$ | $CH_3$ | |
| J-1 | — | H | H | $CH_2CH_2NO_2$ | $CH_3$ | $CH_3$ | |
| J-1 | — | H | H | $CH(CH_3)CH_2NO_2$ | $CH_3$ | $CH_3$ | |
| J-1 | — | H | H | $(CH_2)_3NO_2$ | $CH_3$ | $CH_3$ | |
| J-2 | — | H | H | $CH_2CH_2N_3$ | $CH_3$ | $CH_3$ | |
| J-2 | — | H | H | $CH_2CH_2SCN$ | $CH_3$ | $CH_3$ | |
| J-2 | — | H | H | $CH_2CH_2NO_2$ | $CH_3$ | $CH_3$ | |
| J-3 | | H | H | $CH_2CH_2N_3$ | $CH_3$ | $CH_3$ | |
| J-3 | | H | H | $CH_2CH_2SCN$ | $CH_3$ | $CH_3$ | |
| J-3 | | H | H | $CH_2CH_2NO_2$ | $CH_3$ | $CH_3$ | |
| J-4 | | H | H | $CH_2CH_2N_3$ | $CH_3$ | $CH_3$ | |
| J-4 | | H | H | $CH_2CH_2SCN$ | $CH_3$ | $CH_3$ | |
| J-4 | | H | H | $CH_2CH_2NO_2$ | $CH_3$ | $CH_3$ | |
| J-5 | | H | H | $CH_2CH_2N_3$ | $CH_3$ | $CH_3$ | |
| J-5 | | H | H | $CH_2CH_2SCN$ | $CH_3$ | $CH_3$ | |
| J-5 | | H | H | $CH_2CH_2NO_2$ | $CH_3$ | $CH_3$ | |
| J-6(n = 0) | — | H | H | $CH_2CH_2N_3$ | $CH_3$ | $CH_3$ | |
| J-6(n = 0) | — | H | H | $CH_2CH_2SCN$ | $CH_3$ | $CH_3$ | |
| J-6(n = 0) | — | H | H | $CH_2CH_2NO_2$ | $CH_3$ | $CH_3$ | |
| J-7(n = 0) | — | H | H | $CH_2CH_2N_3$ | $CH_3$ | $CH_3$ | |
| J-7(n = 0) | — | H | H | $CH_2CH_2SCN$ | $CH_3$ | $CH_3$ | |
| J-7(n = 0) | — | H | H | $CH_2CH_2NO_2$ | $CH_3$ | $CH_3$ | |
| J-8(n = 0) | — | H | H | $CH_2CH_2N_3$ | $CH_3$ | $CH_3$ | |
| J-8(n = 0) | — | H | H | $CH_2CH_2SCN$ | $CH_3$ | $CH_3$ | |
| J-8(n = 0) | — | H | H | $CH_2CH_2NO_2$ | $CH_3$ | $CH_3$ | |
| J-9($R^3$ = $CH_3$) | | H | H | $CH_2CH_2N_3$ | $CH_3$ | $CH_3$ | |
| J-9($R^3$ = $CH_3$) | | H | H | $CH_2CH_2SCN$ | $CH_3$ | $CH_3$ | |
| J-9($R^3$ = $CH_3$) | | H | H | $CH_2CH_2NO_2$ | $CH_3$ | $CH_3$ | |
| J-10($R^3$ = $CH_3$) | | H | H | $CH_2CH_2N_3$ | $CH_3$ | $CH_3$ | |

TABLE 5-continued

GENERAL FORMULA 5

| J | E | R | R¹/R² | Q | $X_1$ | $Y_3$ | m.p. °C. |
|---|---|---|---|---|---|---|---|
| J-10(R³ = CH₃) | | H | H | CH₂CH₂SCN | CH₃ | CH₃ | |
| J-10(R³ = CH₃) | | H | H | CH₂CH₂NO₂ | CH₃ | CH₃ | |
| J-11(R³ = CH₃) | | H | H | CH₂CH₂N₃ | CH₃ | CH₃ | |
| J-11(R³ = CH₃) | | H | H | CH₂CH₂SCN | CH₃ | CH₃ | |
| J-11(R³ = CH₃) | | H | H | CH₂CH₂NO₂ | CH₃ | CH₃ | |
| J-12(R³ = CH₃) | | H | H | CH₂CH₂N₃ | CH₃ | CH₃ | |
| J-12(R³ = CH₃) | | H | H | CH₂CH₂SCN | CH₃ | CH₃ | |
| J-12(R³ = CH₃) | | H | H | CH₂CH₂NO₂ | CH₃ | CH₃ | |

TABLE 6

GENERAL FORMULA 6

| J | E | R | R¹/R² | Q | $X_2$ | $Y_2$ | m.p. °C. |
|---|---|---|---|---|---|---|---|
| J-1 | — | H | H | CH₂CH₂N₃ | C₂H₅ | OCH₃ | |
| J-1 | — | H | H | CH₂CH₂N₃ | CH₂CF₃ | OCH₃ | |
| J-1 | — | H | H | CH₂CH₂N₃ | CH₃ | OCH₃ | |
| J-1 | — | H | H | CH₂CH₂N₃ | CH₃ | OC₂H₅ | |
| J-1 | — | H | H | CH₂CH₂N₃ | CH₃ | SCH₃ | |
| J-1 | — | H | H | CH₂CH₂N₃ | CH₃ | SC₂H₅ | |
| J-1 | — | H | H | CH₂CH₂N₃ | CH₃ | CH₃ | |
| J-1 | — | H | H | CH₂CH₂N₃ | CH₃ | C₂H₅ | |
| J-1 | — | CH₃ | H | CH₂CH₂N₃ | CH₃ | OCH₃ | |
| J-1 | — | H | 5-Cl | CH₂CH₂N₃ | CH₃ | OCH₃ | |
| J-1 | — | H | 5-OCH₃ | CH₂CH₂N₃ | CH₃ | OCH₃ | |
| J-1 | — | H | 5-CH₃ | CH₂CH₂N₃ | CH₃ | OCH₃ | |
| J-1 | — | H | 3-Cl | CH₂CH₂N₃ | CH₃ | OCH₃ | |
| J-1 | — | H | H | CH(CH₃)CH₂N₃ | CH₃ | OCH₃ | |
| J-1 | — | H | H | (CH₂)₃N₃ | CH₃ | OCH₃ | |
| J-1 | — | H | H | CH₂CH₂SCN | CH₃ | OCH₃ | |
| J-1 | — | H | H | CH(CH₃)CH₂SCN | CH₃ | OCH₃ | |
| J-1 | — | H | H | (CH₂)₃SCN | CH₃ | OCH₃ | |
| J-1 | — | H | H | CH₂CH₂NO₂ | CH₃ | OCH₃ | |
| J-1 | — | H | H | CH(CH₃)CH₂NO₂ | CH₃ | OCH₃ | |
| J-1 | — | H | H | (CH₂)₃NO₂ | CH₃ | OCH₃ | |
| J-2 | — | H | H | CH₂CH₂N₃ | CH₃ | OCH₃ | |
| J-2 | — | H | H | CH₂CH₂SCN | CH₃ | OCH₃ | |
| J-2 | — | H | H | CH₂CH₂NO₂ | CH₃ | OCH₃ | |
| J-3 | | H | H | CH₂CH₂N₃ | CH₃ | OCH₃ | |
| J-3 | | H | H | CH₂CH₂SCN | CH₃ | OCH₃ | |
| J-3 | | H | H | CH₂CH₂NO₂ | CH₃ | OCH₃ | |
| J-4 | | H | H | CH₂CH₂N₃ | CH₃ | OCH₃ | |
| J-4 | | H | H | CH₂CH₂SCN | CH₃ | OCH₃ | |
| J-4 | | H | H | CH₂CH₂NO₂ | CH₃ | OCH₃ | |
| J-5 | | H | H | CH₂CH₂N₃ | CH₃ | OCH₃ | |
| J-5 | | H | H | CH₂CH₂SCN | CH₃ | OCH₃ | |
| J-5 | | H | H | CH₂CH₂NO₂ | CH₃ | OCH₃ | |
| J-6(n = 0) | — | H | H | CH₂CH₂N₃ | CH₃ | OCH₃ | |
| J-6(n = 0) | — | H | H | CH₂CH₂SCN | CH₃ | OCH₃ | |
| J-6(n = 0) | — | H | H | CH₂CH₂NO₂ | CH₃ | OCH₃ | |
| J-7(n = 0) | — | H | H | CH₂CH₂N₃ | CH₃ | OCH₃ | |
| J-7(n = 0) | — | H | H | CH₂CH₂SCN | CH₃ | OCH₃ | |
| J-7(n = 0) | — | H | H | CH₂CH₂NO₂ | CH₃ | OCH₃ | |
| J-8(n = 0) | — | H | H | CH₂CH₂N₃ | CH₃ | OCH₃ | |
| J-8(n = 0) | — | H | H | CH₂CH₂SCN | CH₃ | OCH₃ | |
| J-8(n = 0) | — | H | H | CH₂CH₂NO₂ | CH₃ | OCH₃ | |
| J-9(R³ = CH₃) | | H | H | CH₂CH₂N₃ | CH₃ | OCH₃ | |
| J-9(R³ = CH₃) | | H | H | CH₂CH₂SCN | CH₃ | OCH₃ | |
| J-9(R³ = CH₃) | | H | H | CH₂CH₂NO₂ | CH₃ | OCH₃ | |
| J-10(R³ = CH₃) | | H | H | CH₂CH₂N₃ | CH₃ | OCH₃ | |
| J-10(R³ = CH₃) | | H | H | CH₂CH₂SCN | CH₃ | OCH₃ | |
| J-10(R³ = CH₃) | | H | H | CH₂CH₂NO₂ | CH₃ | OCH₃ | |
| J-11(R³ = CH₃) | | H | H | CH₂CH₂N₃ | CH₃ | OCH₃ | |
| J-11(R³ = CH₃) | | H | H | CH₂CH₂SCN | CH₃ | OCH₃ | |
| J-11(R³ = CH₃) | | H | H | CH₂CH₂NO₂ | CH₃ | OCH₃ | |
| J-12(R³ = CH₃) | | H | H | CH₂CH₂N₃ | CH₃ | OCH₃ | |
| J-12(R³ = CH₃) | | H | H | CH₂CH₂SCN | CH₃ | OCH₃ | |
| J-12(R³ = CH₃) | | H | H | CH₂CH₂NO₂ | CH₃ | OCH₃ | |

TABLE 7

GENERAL FORMULA 7

| J | E | R | R¹/R² | Q | $X_3$ | m.p. °C. |
|---|---|---|---|---|---|---|
| J-1 | — | H | H | CH₂CH₂N₃ | CH₃ | |
| J-1 | — | H | H | CH₂CH₂N₃ | OCH₃ | |
| J-1 | — | CH₃ | H | CH₂CH₂N₃ | OCH₃ | |
| J-1 | — | H | 5-Cl | CH₂CH₂N₃ | OCH₃ | |

TABLE 7-continued

GENERAL FORMULA 7

| J | E | R | R$^1$/R$^2$ | Q | X$_3$ | m.p. °C. |
|---|---|---|---|---|---|---|
| J-1 | — | H | 5-OCH$_3$ | CH$_2$CH$_2$N$_3$ | OCH$_3$ | |
| J-1 | — | H | 5-CH$_3$ | CH$_2$CH$_2$N$_3$ | OCH$_3$ | |
| J-1 | — | H | 3-Cl | CH$_2$CH$_2$N$_3$ | OCH$_3$ | |
| J-1 | — | H | H | CH(CH$_3$)CH$_2$N$_3$ | OCH$_3$ | |
| J-1 | — | H | H | (CH$_2$)$_3$N$_3$ | OCH$_3$ | |
| J-1 | — | H | H | CH$_2$CH$_2$SCN | OCH$_3$ | |
| J-1 | — | H | H | CH(CH$_3$)CH$_2$SCN | OCH$_3$ | |
| J-1 | — | H | H | (CH$_2$)$_3$SCN | OCH$_3$ | |
| J-1 | — | H | H | CH$_2$CH$_2$NO$_2$ | OCH$_3$ | |
| J-1 | — | H | H | CH(CH$_3$)CH$_2$NO$_2$ | OCH$_3$ | |
| J-1 | — | H | H | (CH$_2$)$_3$NO$_2$ | OCH$_3$ | |
| J-2 | — | H | H | CH$_2$CH$_2$N$_3$ | OCH$_3$ | |
| J-2 | — | H | H | CH$_2$CH$_2$SCN | OCH$_3$ | |
| J-2 | — | H | H | CH$_2$CH$_2$NO$_2$ | OCH$_3$ | |
| J-3 | | H | H | CH$_2$CH$_2$N$_3$ | OCH$_3$ | |
| J-3 | | H | H | CH$_2$CH$_2$SCN | OCH$_3$ | |
| J-3 | | H | H | CH$_2$CH$_2$NO$_2$ | OCH$_3$ | |
| J-4 | | H | H | CH$_2$CH$_2$N$_3$ | OCH$_3$ | |
| J-4 | | H | H | CH$_2$CH$_2$SCN | OCH$_3$ | |
| J-4 | | H | H | CH$_2$CH$_2$NO$_2$ | OCH$_3$ | |
| J-5 | | H | H | CH$_2$CH$_2$N$_3$ | OCH$_3$ | |
| J-5 | | H | H | CH$_2$CH$_2$SCN | OCH$_3$ | |
| J-5 | | H | H | CH$_2$CH$_2$NO$_2$ | OCH$_3$ | |
| J-6(n = 0) | — | H | H | CH$_2$CH$_2$N$_3$ | OCH$_3$ | |
| J-6(n = 0) | — | H | H | CH$_2$CH$_2$SCN | OCH$_3$ | |
| J-6(n = 0) | — | H | H | CH$_2$CH$_2$NO$_2$ | OCH$_3$ | |
| J-7(n = 0) | — | H | H | CH$_2$CH$_2$N$_3$ | OCH$_3$ | |
| J-7(n = 0) | — | H | H | CH$_2$CH$_2$SCN | OCH$_3$ | |
| J-7(n = 0) | — | H | H | CH$_2$CH$_2$NO$_2$ | OCH$_3$ | |
| J-8(n = 0) | — | H | H | CH$_2$CH$_2$N$_3$ | OCH$_3$ | |
| J-8(n = 0) | — | H | H | CH$_2$CH$_2$SCN | OCH$_3$ | |
| J-8(n = 0) | — | H | H | CH$_2$CH$_2$NO$_2$ | OCH$_3$ | |
| J-9(R$^3$=CH$_3$) | | H | H | CH$_2$CH$_2$N$_3$ | OCH$_3$ | |
| J-9(R$^3$=CH$_3$) | | H | H | CH$_2$CH$_2$SCN | OCH$_3$ | |
| J-9(R$^3$=CH$_3$) | | H | H | CH$_2$CH$_2$NO$_2$ | OCH$_3$ | |
| J-10(R$^3$=CH$_3$) | | H | H | CH$_2$CH$_2$N$_3$ | OCH$_3$ | |
| J-10(R$^3$=CH$_3$) | | H | H | CH$_2$CH$_2$SCN | OCH$_3$ | |
| J-10(R$^3$=CH$_3$) | | H | H | CH$_2$CH$_2$NO$_2$ | OCH$_3$ | |
| J-11(R$^3$=CH$_3$) | | H | H | CH$_2$CH$_2$N$_3$ | OCH$_3$ | |
| J-11(R$^3$=CH$_3$) | | H | H | CH$_2$CH$_2$SCN | OCH$_3$ | |
| J-11(R$^3$=CH$_3$) | | H | H | CH$_2$CH$_2$NO$_2$ | OCH$_3$ | |
| J-12(R$^3$=CH$_3$) | | H | H | CH$_2$CH$_2$N$_3$ | OCH$_3$ | |
| J-12(R$^3$=CH$_3$) | | H | H | CH$_2$CH$_2$SCN | OCH$_3$ | |
| J-12(R$^3$=CH$_3$) | | H | H | CH$_2$CH$_2$NO$_2$ | OCH$_3$ | |

TABLE 8

GENERAL FORMULA 8

| J | E | R | R$^1$/R$^2$ | Q | Z$_1$ | X$_4$ | Y$_4$ | m.p. °C. |
|---|---|---|---|---|---|---|---|---|
| J-1 | — | H | H | CH$_2$CH$_2$N$_3$ | CH | CH$_3$ | CH$_3$ | |
| J-1 | — | H | H | CH$_2$CH$_2$N$_3$ | N | CH$_3$ | CH$_3$ | |
| J-1 | — | H | H | CH$_2$CH$_2$N$_3$ | CH | OCH$_3$ | CH$_3$ | |
| J-1 | — | H | H | CH$_2$CH$_2$N$_3$ | N | OCH$_3$ | CH$_3$ | |
| J-1 | — | H | H | CH$_2$CH$_2$N$_3$ | CH | OCH$_3$ | OCH$_3$ | |
| J-1 | — | H | H | CH$_2$CH$_2$N$_3$ | N | OCH$_3$ | OCH$_3$ | |
| J-1 | — | H | H | CH$_2$CH$_2$N$_3$ | CH | Cl | CH$_3$ | |
| J-1 | — | H | H | CH$_2$CH$_2$N$_3$ | CH | OCH$_3$ | Cl | |
| J-1 | — | H | H | CH$_2$CH$_2$N$_3$ | CH | OC$_2$H$_5$ | CH$_3$ | |
| J-1 | — | H | H | CH$_2$CH$_2$N$_3$ | N | CH$_2$OCH$_3$ | CH$_3$ | |
| J-1 | — | H | H | CH$_2$CH$_2$N$_3$ | CH | CH$_2$OCH$_3$ | OCH$_3$ | |
| J-1 | — | H | H | CH$_2$CH$_2$N$_3$ | N | OC$_2$H$_5$ | OC$_2$H$_5$ | |
| J-1 | — | CH$_3$ | H | CH$_2$CH$_2$N$_3$ | CH | OCH$_3$ | CH$_3$ | |
| J-1 | — | H | 5-Cl | CH$_2$CH$_2$N$_3$ | CH | OCH$_3$ | CH$_3$ | |
| J-1 | — | H | 5-OCH$_3$ | CH$_2$CH$_2$N$_3$ | CH | OCH$_3$ | CH$_3$ | |
| J-1 | — | H | 5-CH$_3$ | CH$_2$CH$_2$N$_3$ | CH | OCH$_3$ | CH$_3$ | |
| J-1 | — | H | 3-Cl | CH$_2$CH$_2$N$_3$ | CH | OCH$_3$ | CH$_3$ | |
| J-1 | — | H | H | CH(CH$_3$)CH$_2$N$_3$ | CH | OCH$_3$ | CH$_3$ | |
| J-1 | — | H | H | (CH$_2$)$_3$N$_3$ | CH | OCH$_3$ | CH$_3$ | |
| J-1 | — | H | H | CH$_2$CH$_2$SCN | CH | OCH$_3$ | CH$_3$ | |
| J-1 | — | H | H | CH(CH$_3$)CH$_2$SCN | CH | OCH$_3$ | CH$_3$ | |
| J-1 | — | H | H | (CH$_2$)$_3$SCN | CH | OCH$_3$ | CH$_3$ | |
| J-1 | — | H | H | CH$_2$CH$_2$NO$_2$ | CH | OCH$_3$ | CH$_3$ | |
| J-1 | — | H | H | CH(CH$_3$)CH$_2$NO$_2$ | CH | OCH$_3$ | CH$_3$ | |
| J-1 | — | H | H | (CH$_2$)$_3$NO$_2$ | CH | OCH$_3$ | CH$_3$ | |
| J-2 | — | H | H | CH$_2$CH$_2$N$_3$ | CH | OCH$_3$ | CH$_3$ | |
| J-2 | — | H | H | CH$_2$CH$_2$SCN | CH | OCH$_3$ | CH$_3$ | |
| J-2 | — | H | H | CH$_2$CH$_2$NO$_2$ | CH | OCH$_3$ | CH$_3$ | |
| J-3 | | H | H | CH$_2$CH$_2$N$_3$ | CH | OCH$_3$ | CH$_3$ | |

TABLE 8-continued

GENERAL FORMULA 8

| J | E | R | R¹/R² | Q | $Z_1$ | $X_4$ | $Y_4$ | m.p. °C. |
|---|---|---|---|---|---|---|---|---|
| J-3 | | H | H | $CH_2CH_2SCN$ | CH | $OCH_3$ | $CH_3$ | |
| J-3 | | H | H | $CH_2CH_2NO_2$ | CH | $OCH_3$ | $CH_3$ | |
| J-4 | | H | H | $CH_2CH_2N_3$ | CH | $OCH_3$ | $CH_3$ | |
| J-4 | | H | H | $CH_2CH_2SCN$ | CH | $OCH_3$ | $CH_3$ | |
| J-4 | | H | H | $CH_2CH_2NO_2$ | CH | $OCH_3$ | $CH_3$ | |
| J-5 | | H | H | $CH_2CH_2N_3$ | CH | $OCH_3$ | $CH_3$ | |
| J-5 | | H | H | $CH_2CH_2SCN$ | CH | $OCH_3$ | $CH_3$ | |
| J-5 | | H | H | $CH_2CH_2NO_2$ | CH | $OCH_3$ | $CH_3$ | |
| J-6(n = 0) | — | H | H | $CH_2CH_2N_3$ | CH | $OCH_3$ | $CH_3$ | |
| J-6(n = 0) | — | H | H | $CH_2CH_2SCN$ | CH | $OCH_3$ | $CH_3$ | |
| J-6(n = 0) | — | H | H | $CH_2CH_2NO_2$ | CH | $OCH_3$ | $CH_3$ | |
| J-7(n = 0) | — | H | H | $CH_2CH_2N_3$ | CH | $OCH_3$ | $CH_3$ | |
| J-7(n = 0) | — | H | H | $CH_2CH_2SCN$ | CH | $OCH_3$ | $CH_3$ | |
| J-7(n = 0) | — | H | H | $CH_2CH_2NO_2$ | CH | $OCH_3$ | $CH_3$ | |
| J-8(n = 0) | — | H | H | $CH_2CH_2N_3$ | CH | $OCH_3$ | $CH_3$ | |
| J-8(n = 0) | — | H | H | $CH_2CH_2SCN$ | CH | $OCH_3$ | $CH_3$ | |
| J-8(n = 0) | — | H | H | $CH_2CH_2NO_2$ | CH | $OCH_3$ | $CH_3$ | |
| J-9($R^3$=$CH_3$) | | H | H | $CH_2CH_2N_3$ | CH | $OCH_3$ | $CH_3$ | |
| J-9($R^3$=$CH_3$) | | H | H | $CH_2CH_2SCN$ | CH | $OCH_3$ | $CH_3$ | |
| J-9($R^3$=$CH_3$) | | H | H | $CH_2CH_2NO_2$ | CH | $OCH_3$ | $CH_3$ | |
| J-10($R^3$=$CH_3$) | | H | H | $CH_2CH_2N_3$ | CH | $OCH_3$ | $CH_3$ | |
| J-10($R^3$=$CH_3$) | | H | H | $CH_2CH_2SCN$ | CH | $OCH_3$ | $CH_3$ | |
| J-10($R^3$=$CH_3$) | | H | H | $CH_2CH_2NO_2$ | CH | $OCH_3$ | $CH_3$ | |
| J-11($R^3$=$CH_3$) | | H | H | $CH_2CH_2N_3$ | CH | $OCH_3$ | $CH_3$ | |
| J-11($R^3$=$CH_3$) | | H | H | $CH_2CH_2SCN$ | CH | $OCH_3$ | $CH_3$ | |
| J-11($R^3$=$CH_3$) | | H | H | $CH_2CH_2NO_2$ | CH | $OCH_3$ | $CH_3$ | |
| J-12($R^3$=$CH_3$) | | H | H | $CH_2CH_2N_3$ | CH | $OCH_3$ | $CH_3$ | |
| J-12($R^3$=$CH_3$) | | H | H | $CH_2CH_2SCN$ | CH | $OCH_3$ | $CH_3$ | |
| J-12($R^3$=$CH_3$) | | H | H | $CH_2CH_2NO_2$ | CH | $OCH_3$ | $CH_3$ | |

TABLE 9

GENERAL FORMULA 9

| J | E | R¹/R² | Q | Z | X | Y | m.p. °C. |
|---|---|---|---|---|---|---|---|
| J-1 | — | H | $CH_2CH_2N_3$ | CH | $OCH_3$ | $OCH_3$ | |
| J-1 | — | H | $CH_2CH_2N_3$ | CH | $OCH_3$ | $CH_3$ | |
| J-1 | — | H | $CH_2CH_2N_3$ | CH | $CH_3$ | $CH_3$ | |
| J-1 | — | H | $CH_2CH_2N_3$ | N | $OCH_3$ | $OCH_3$ | |
| J-1 | — | H | $CH_2CH_2N_3$ | N | $OCH_3$ | $CH_3$ | |
| J-1 | — | 5-Cl | $CH_2CH_2N_3$ | CH | $OCH_3$ | $OCH_3$ | |
| J-1 | — | 5-$OCH_3$ | $CH_2CH_2N_3$ | CH | $OCH_3$ | $OCH_3$ | |
| J-1 | — | 5-$CH_3$ | $CH_2CH_2N_3$ | CH | $OCH_3$ | $OCH_3$ | |
| J-1 | — | 3-Cl | $CH_2CH_2N_3$ | CH | $OCH_3$ | $OCH_3$ | |
| J-1 | — | H | $CH_2CH_2SCN$ | CH | $OCH_3$ | $OCH_3$ | |
| J-1 | — | H | $CH_2CH_2NO_2$ | CH | $OCH_3$ | $OCH_3$ | |
| J-2 | — | H | $CH_2CH_2N_3$ | CH | $OCH_3$ | $OCH_3$ | |
| J-2 | — | H | $CH_2CH_2SCN$ | CH | $OCH_3$ | $OCH_3$ | |
| J-2 | — | H | $CH_2CH_2NO_2$ | CH | $OCH_3$ | $OCH_3$ | |
| J-3 | | H | $CH_2CH_2N_3$ | CH | $OCH_3$ | $OCH_3$ | |
| J-3 | | H | $CH_2CH_2SCN$ | CH | $OCH_3$ | $OCH_3$ | |
| J-3 | | H | $CH_2CH_2NO_3$ | CH | $OCH_3$ | $OCH_3$ | |
| J-4 | | H | $CH_2CH_2N_3$ | CH | $OCH_3$ | $OCH_3$ | |
| J-4 | | H | $CH_2CH_2SCN$ | CH | $OCH_3$ | $OCH_3$ | |
| J-4 | | H | $CH_2CH_2NO_2$ | CH | $OCH_3$ | $OCH_3$ | |
| J-5 | | H | $CH_2CH_2N_3$ | CH | $OCH_3$ | $OCH_3$ | |
| J-5 | | H | $CH_2CH_2SCN$ | CH | $OCH_3$ | $OCH_3$ | |
| J-5 | | H | $CH_2CH_2NO_2$ | CH | $OCH_3$ | $OCH_3$ | |
| J-6(n = 0) | — | H | $CH_2CH_2N_3$ | CH | $OCH_3$ | $OCH_3$ | |
| J-6(n = 0) | — | H | $CH_2CH_2SCN$ | CH | $OCH_3$ | $OCH_3$ | |
| J-6(n = 0) | — | H | $CH_2CH_2NO_2$ | CH | $OCH_3$ | $OCH_3$ | |
| J-7(n = 0) | — | H | $CH_2CH_2N_3$ | CH | $OCH_3$ | $OCH_3$ | |
| J-7(n = 0) | — | H | $CH_2CH_2SCN$ | CH | $OCH_3$ | $OCH_3$ | |
| J-7(n = 0) | — | H | $CH_2CH_2NO_2$ | CH | $OCH_3$ | $OCH_3$ | |
| J-8(n = 0) | — | H | $CH_2CH_2N_3$ | CH | $OCH_3$ | $OCH_3$ | |
| J-8(n = 0) | — | H | $CH_2CH_2SCN$ | CH | $OCH_3$ | $OCH_3$ | |
| J-8(n = 0) | — | H | $CH_2CH_2NO_2$ | CH | $OCH_3$ | $OCH_3$ | |
| J-9($R^3$=$CH_3$) | | H | $CH_2CH_2N_3$ | CH | $OCH_3$ | $OCH_3$ | |
| J-9($R^3$=$CH_3$) | | H | $CH_2CH_2SCN$ | CH | $OCH_3$ | $OCH_3$ | |
| J-9($R^3$=$Ch_3$) | | H | $CH_2CH_2NO_2$ | CH | $OCH_3$ | $OCH_3$ | |
| J-10($R^3$=$CH_3$) | | H | $CH_2CH_2N$ | CH | $OCH_3$ | $OCH_3$ | |
| J-10($R^3$=$CH_3$) | | H | $CH_2CH_2SCN$ | CH | $OCH_3$ | $OCH_3$ | |
| J-10($R_3$=$CH_3$) | | H | $CH_2CH_2NO_2$ | CH | $OCH_3$ | $OCH_3$ | |
| J-11($R^3$=$CH_3$) | | H | $CH_2CH_2N_3$ | CH | $OCH_3$ | $OCH_3$ | |
| J-11($R^3$=$CH_3$) | | H | $CH_2CH_2SCN$ | CH | $OCH_3$ | $OCH_3$ | |
| J-11($R^3$=$CH_3$) | | H | $CH_2CH_2NO_2$ | CH | $OCH_3$ | $OCH_3$ | |
| J-12($R^3$=$CH_3$) | | H | $CH_2CH_2N_3$ | CH | $OCH_3$ | $OCH_3$ | |
| J-12($R^3$=$CH_3$) | | H | $CH_2CH_2SCN$ | CH | $OCH_3$ | $OCh_3$ | |

TABLE 9-continued

| GENERAL FORMULA 9 | | | | | | | |
|---|---|---|---|---|---|---|---|
| J | E | $R^1/R^2$ | Q | Z | X | Y | m.p. °C. |
| J-12($R^3$=$CH_3$) | | H | $CH_2CH_2NO_2 \cdot CH$ | | $OCH_3$ | $OCH_3$ | |

Formulations

Useful formulations of the compounds of Formula I can be prepared and applied to vegetation in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

| | Active | Weight Percent* | |
|---|---|---|---|
| | Ingredient | Diluent(s) | Surfactant(s) |
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, N.Y., 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., N.Y., 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, N.Y., 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., N.Y., 1961, pp. 81–96; and J. D. Fryer and S. A. Evans, "Weed Control Handbook", 5th Ed., Blackwell Scientific Publications, Oxford, 1968, pp. 101–103.

In the following Examples, all parts are by weight unless otherwise indicated.

EXAMPLE 6

Wettable Powder

| | |
|---|---|
| 2-[[(4,6-Dimethoxypyrimidin-2-yl)aminocarbonyl]aminosulfonyl]benzoic acid, 2-azidoethyl ester | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 7

Wettable Powder

| | |
|---|---|
| 2-[[(4-Methoxy-6-methyl-1,3,5-triazin-2-yl)aminocarbonyl]aminosulfonyl]benzoic acid, 2-azidoethyl ester | 50% |
| sodium alkylnaphthalenesulfonate | 2% |
| low viscosity methyl cellulose | 2% |
| diatomaceous earth | 46% |

The ingredients are blended, coarsely hammermilled and then air-milled to produce particles essentially all below 10 microns in diameter. The product is reblended before packaging.

EXAMPLE 8

Granule

| | |
|---|---|
| Wettable Powder of Example 7 | 5% |
| attapulgite granules | 95% |

(U.S.S. 20 to 40 mesh; 0.84–0.42 mm)

A slurry of wettable powder containing 25% solids is sprayed on the surface of attapulgite granules in a double-cone blender. The granules are dried and packaged.

EXAMPLE 9

Extruded Pellet

| | |
|---|---|
| 2-[[(4,6-Dimethoxypyrimidin-2-yl)aminocarbonyl]aminosulfonyl]benzoic acid, 2-azidoethyl ester | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 10

Low Strength Granule

| | |
|---|---|
| 2-[[(4-Methoxy-6-methyl-1,3,5-triazin-2-yl)aminocarbonyl]aminosulfonyl]benzoic acid, 2-azidoethyl ester | 0.1% |
| attapulgite granules (U.S.S. 20 to 40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 11

Granule

| | |
|---|---|
| 2-[[(4,6-Dimethoxypyrimidin-2-yl)aminocarbonyl]aminosulfonyl]benzoic acid, 2-azidoethyl ester | 80% |
| wetting agent | 1% |
| crude ligninsulfonate salt (containing 5 to 20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14 to 100 mesh (1410 to 149 microns) and packaged for use.

EXAMPLE 12

Low Strength Granule

| | |
|---|---|
| 2-[[(4-Methoxy-6-methyl-1,3,5-triazin-2-yl)aminocarbonyl]aminosulfonyl]benzoic acid, 2-azidoethyl ester | 1% |
| N,N—dimethylformamide | 9% |
| attapulgite granules (U.S.S. 20 to 40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 13

Aqueous Suspension

| | |
|---|---|
| 2-[[(4,6-Dimethoxypyrimidin-2-yl)aminocarbonyl]aminosulfonyl]benzoic acid, 2-azidoethyl ester | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 14

Solution

| | |
|---|---|
| 2-[[(4-Methoxy-6-methyl-1,3,5-triazin-2-yl)aminocarbonyl]aminosulfonyl]benzoic acid, 2-azidoethyl ester salt | 5% |
| water | 95% |

The salt is added directly to the water with stirring to produce the solution, which may then be packaged for use.

EXAMPLE 15

High Strength Concentrate

| | |
|---|---|
| 2-[[(4,6-Dimethoxypyrimidin-2-yl)aminocarbonyl]aminosulfonyl]benzoic acid, 2-azidoethyl ester | 99% |
| silica aerogel | 0.5% |
| synthetic amorphous silica | 0.5% |

The ingredients are blended and ground in a hammermill to produce a material essentially all passing a U.S.S. No. 50 screen (0.3 mm opening). The concentrate may be formulated further if necessary.

EXAMPLE 16

Wettable Powder

| | |
|---|---|
| 2-[[(4-Methoxy-6-methyl-1,3,5-triazin-2-yl)aminocarbonyl]aminosulfonyl]benzoic acid, 2-azidoethyl ester | 90% |
| dioctyl sodium sulfosuccinate | 0.1 |
| synthetic fine silica | 9.9% |

EXAMPLE 17

Wettable Powder

| | |
|---|---|
| 2-[[(4,6-Dimethoxypyrimidin-2-yl)aminocarbonyl]aminosulfonyl]benzoic acid, 2-azidoethyl ester | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 18

Oil Ssuspension

| | |
|---|---|
| 2-[[(4-Methoxy-6-methyl-1,3,5-triazin-2-yl)aminocarbonyl]aminosulfonyl]benzoic acid, 2-azidoethyl ester | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 19

Dust

| | |
|---|---|
| 2-[[(4,6-Dimethoxypyrimidin-2-yl)aminocarbonyl]aminosulfonyl]benzoic acid, 2-azidoethyl ester | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE 20

Oil Suspension

| | |
|---|---|
| 2-[[(4-Methoxy-6-methyl-1,3,5-triazin-2-yl)aminocarbonyl]aminosulfonyl]benzoic acid, 2-azidoethyl ester | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

The ingredients are blended and ground in a hammer-mill to produce particles essentially all below 100 microns. The material is sifted through a U.S.S. No. 50 screen and then packaged.

EXAMPLE 21

Wettable Powder

| | |
|---|---|
| 2-[[(4,6-Dimethoxypyrimidin-2-yl)aminocarbonyl]aminosulfonyl]benzoic acid, 2-azidoethyl ester | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

Utility

Test results indicate that the compounds of the present invention are highly active preemergent or postemergent herbicides or plant growth regulants. Many of them have utility for broad-spectrum pre-and/or post-emergence weed control in areas where complete control of all vegetation is desired, such as around storage areas, parking lots, drive-in theaters, around billboards, highway and railroad structures. Some of the compounds have utility for selective weed control in crops such as wheat, barley and soybeans. Alternatively, the subject compounds are useful to modify plant growth.

The rates of application for the compounds of the invention are determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of around 0.001 to 10 kg/ha, the lower rates being suggested for use on lighter soils and/or those having a low organic matter content, for plant growth modification or for situations where only short-term persistence is required.

The compound of this invention may be used in combination with other commercial herbicides, insecticides or fungicides. The following list exemplifies some of the herbicides suitable for use in mixtures.

| Common Name | Chemical Name |
|---|---|
| acifluorfen | 5-[2-chloro-4-(trifluoromethyl)phenoxy]-2-nitrobenzoic acid |
| alachlor | 2-chloro-2',6'-diethyl-N—(methoxymethyl)-acetanilide |
| ametryn | 2-(ethylamino)-4-(isopropylamino)-6-methylthio)-s-triazine |
| asulam | methyl sulfanilylcarbamate |
| atrazine | 2-chloro-4-(ethylamino)-6-(isopropylamino)-s-triazine |
| barban | 4-chloro-2-butynyl m-chlorocarbanilate |
| benefin | N—butyl-N—ethyl-α,α,α-trifluoro-2,6-dinitro-p-toluidine |
| bensulide | O,O—diisopropyl phosphorodithioate S—ester with N—(2-mercaptoethyl)-benzenesulfonamide |
| bentazon | 3-isopropyl-1H—2,1,3-benzothiadiazin-4(3H)—one 2,2-dioxide |
| benzipram | 3,5-dimethyl-N—(1-methylethyl)-N—(phenylmethyl)benzamide |
| benzoylprop | N—benzoyl-N—(3,4-dichlorophenyl)-DL-alaine |
| bifenox | methyl 5-(2,4-dichlorophenoxy)-2-nitrobenzoate |
| bromacil | 5-bromo-3-sec-butyl-6-methyluracil |

-continued

| Common Name | Chemical Name |
|---|---|
| bromofenoxium | 3,5-dibromo-4-hydroxybenzaldehyde-O—2',4'-dinitrophenyl)oxime |
| bromoxynil | 3,5-dibromo-4-hydroxybenzonitrile |
| butachlor | N—(butoxymethyl)-2-chloro-2',6'-diethylacetanilide |
| butam | 2,2-dimethyl-N—(1-methylethyl)-N—(phenylmethyl)propanamide |
| buthidazole | 3-[5-(1,1-dimethylethyl)-1,3,4-thiadiazol-2-yl]-4-hydroxy-1-methyl-2-imidazolidinone |
| butralin | 4-(1,1-dimethylethyl)-N—(1-methylpropyl)-2,6-dinitrobenzenamine |
| butylate | S—ethyl-diisobutylthiocarbamate |
| carbetamide | D-N—ethyllactamide carbanilate (ester) |
| CDAA | N—N—diallyl-2-chloroacetamide |
| CDEC | 2-chloroallyl diethyldithiocarbamate |
| chlorbromuron | 3-(4-bromo-3-chlorophenyl)-1-methoxy-1-methylurea |
| chloroxuron | 3-[p-(p-chlorophenoxy)phenyl]-1,1-dimethylurea |
| chlorpropham | isopropyl m-chlorocarbanilate |
| chlorsulfuron | 2-chloro-N—[[(4-methoxy-6-methyl-1,3,5-triazin-2-yl)aminocarbonyl]benzenesulfonamide |
| chlortoluron | N'—(3-chloro-4-methylphenyl-N',N'—dimethylurea |
| cinmethylin | exo-1-methyl-4-(1-methylethyl)-2-[(2-methylphenyl)methoxy]-7-oxabicyclo-[2.2.1]heptane |
| cisanilide | cis-2,5-dimethyl-N—phenyl-1-pyrrolidinecarboxamide |
| cyanazine | 2-[[4-chloro-6-(ethylamino)-s-triazin-2-yl]amino]-2-methylpropionitrile |
| cycloate | S—ethyl N—ethylthiocyclohexanecarbamate |
| cycluron | 3-cyclooctyl-1,1-dimethylurea |
| cyperquat | 1-methyl-4-phenylpyridinium |
| cyprazine | 2-chloro-4-(cyclopropylamino)-6-(isopropylamino)-s-triazine |
| cyprazole | N—[5-(2-chloro-1,1-dimethylethyl)-1,3,4-thiadiazol-2-yl]cyclopropanecarboxamide |
| cypromid | 3',4'-dichlorocyclopropanecarboxanilide |
| dalapon | 2,2-dichloropropionic acid |
| dazomet | tetrahydro-3,5-dimethyl-2H—1,3,5-thiadiazine-2-thione |
| DCPA | dimethyl tetrachloroterephthalate |
| DNOC | 2-methyl-4,6-dinitrophenol |
| desmetryn | 2-(isopropylamino)-4-(methylamino)-6-methylthio)-s-triazine |
| diallate | S—(2,3-dichloroallyl)diisopropylthiocarbamate |
| dicamba | 3,6-dichloro-o-anisic acid |
| dichlobenil | 2,6-dichlorobenzonitrile |
| dichlorprop | 2-(2,4-dichlorophenoxy)propionic acid |
| diclofop | 2-[4-(2,4-dichlorophenoxy)phenoxy]-propanoic acid |
| diethatyl | N—(chloroacetyl)-N—(2,6-diethylphenyl)-glycine |
| difenzoquat | 1,2-dimethyl-3,5-diphenyl-1H—pyrazolium |
| dinitramine | $N^4,N^4$—diethyl-α,α,α-trifluoro-3,5-dinitrotoluene-2,4-diamine |
| dinoseb | 2-sec-butyl-4,6-dinitrophenol |
| diphenamide | N,N—dimethyl-2,2-diphenylacetamide |
| dipropetryn | 2-(ethylthio)-4,6-bis(isopropylamino)-s-triazine |
| diquat | 6,7-dihydrodipyrido[1,2-α:2',1'-c]-pyrazinediium ion |
| diuron | 3-(3,4-dichlorophenyl)-1,1-dimethylurea |
| endothall | 7-oxabicyclo[2.2.1]heptane-2,3-dicarboxylic acid |
| erbon | 2-(2,4,5-trichlorophenoxy)ethyl 2,2-dichloropropionate |
| ethafluralin | N—ethyl-N—(2-methyl-2-propenyl)-2,6-dinitro-4-(trifluoromethyl)benzenamine |
| ethofumesate | (±)-2-ethoxy-2,3-dihydro-3,3-dimethyl-5-benzofuranyl methanesulfonate |
| fenac | (2,3,6-trichlorophenyl)acetic acid |
| fenoxaprop ethyl | ethyl 2-(4-(6-chloro-2-benzoxazolyl-oxy)phenoxy)propanoate |
| fenuron | 1,1-dimethyl-3-phenylurea |
| fenuron TCA | 1,1-dimethyl-3-phenylurea mono(trichloroacetate) |
| flamprop | N—benzoyl-N—(3-chloro-4-fluorophenyl)-DL-alanine |
| fluchloralin | N—(2-chloroethyl)-2,6-dinitro-N—propyl-4-(trifluoromethyl)aniline |
| fluometuron | 1,1-dimethyl-3-(α,α,α-trifluoro-m-tolyl)-urea |
| fluorodifen | p-nitrophenyl α,α,α-trifluoro-2-nitro-p-tolyl ether |
| fluridone | 1-methyl-3-phenyl-5-[3-(trifluoromethyl)phenyl]-4(1H)—pyridinone |
| fomesafen | 5-(2-chloro-4-trifluoromethylphenoxy)-N—methylsulfonyl-2-nitrobenzamide |
| fosamine | ethyl hydrogen (aminocarbonyl)phosphonate |
| glyphosate | N—(phosphonomethyl)glycine |
| haloxyfop methyl | 2-(4-(3-chloro-5-trifluoromethylpyridin-2-yloxy)phenoxy)propanoic acid, methyl ester |
| hexazinone | 3-cyclohexyl-6-(dimethylamino)-1-methyl-1,3,5-triazine-2,4(1H,3H)—dione |
| imazaquin | 2-(4,5-dihydro-4-methyl-4-(1-methylethyl)-5-oxo-1H—imidazol-2-yl)-3-quinolinecarboxylic acid |
| imazethapyr | 2-[4,5-dihydro-4-methyl-4-(1-methylethyl)-5-oxo-1H—imidazol-2-yl]-5-ethyl-3-pyridinecarboxylic acid |
| ioxynil | 4-hydroxy-3,5-diiodobenzonitrile |
| isopropalin | 2,6-dinitro-N,N—dipropylcumidine |
| isoproturon | N—(4-isopropylphenyl)-N',N'—dimethylurea |
| karbutilate | tert-butylcarbamic acid ester with 3-(m-hydroxyphenyl)-1,1-dimethylurea |
| lactofen | 1'-(carbethoxy)ethyl-5-(2-chloro-4-(trifluoromethyl)phenoxy)-2-nitrobenzoate |
| lenacil | 3-cyclohexyl-6,7-dihydro-1H—cyclopentapyrimidine-2,4(3H,5H)—dione |
| linuron | 3-(3,4-dichlorophenyl)-1-methoxy-1-methylurea |
| MAMA | monoammonium methanearsonate |
| MCPA | [(4-chloro-o-tolyl)oxy]acetic acid |
| MCPB | 4-[(4-chloro-o-tolyl)oxy]butyric acid |
| mecoprop | 2-[(4-chloro-o-tolyl)oxy]propionic acid |
| mefluidide | N—[(2,4-dimethyl-5-[[(trifluoromethyl)-sulfonyl]amino]phenyl]acetamide |
| methalpropalin | N—(2-methyl-2-propenyl)-2,6-dinitro-N—propyl-4-(trifluoromethyl)benzenamine |
| methabenzthiazuron | 1,3-dimethyl-3-(2-benzothiazolyl)urea |
| methazole | 2-(3,4-dichlorophenyl)-4-methyl-1,2,4-oxadiazolidine-3,5-dione |
| methoxuron | N'—(3-chloro-4-methoxyphenyl)N,N—dimethylurea |
| metolachlor | 2-chloro-N—(2-ethyl-6-methylphenyl)-N—(2-methoxy-1-methylethyl)acetamide |
| metribuzin | 4-amino-6-tert-butyl-3-(methylthio)-as-triazine-5(4H)—one |
| metsulfuron methyl | 2-[[[(4-methoxy-6-methyl-1,3,5-triazine-2-yl)aminocarbonyl]aminosulfonyl]benzoic acid, methyl ester |
| molinate | S—ethyl hexahydro-1H—azepine-1-carbothioate |
| monolinuron | 3-(p-chlorophenyl)-1-methoxy-1-methylurea |
| monuron | 3-(p-chlorophenyl)-1,1-dimethylurea |
| monuron TCA | 3-(p-chlorophenyl)-1,1-dimethylurea mono(trichloroacetate) |
| napropamide | 2-(α-naphthoxy)-N,N—diethylpropionamide |
| naptalam | N-1-naphthylphthalamic acid |
| neburon | 1-butyl-3-(3,4-dichlorophenyl)-1-methylurea |
| nitralin | 4-(methylsulfonyl)-2,6-dinitro-N,N—dipropylaniline |
| nitrofen | 2,4-dichlorophenyl p-nitrophenyl ether |
| nitrofluorfen | 2-chloro-1-(4-nitrophenoxy)-4-(trifluoromethyl)benzene |
| norflurazon | 4-chloro-5-(methylamino)-2-(α,α,α-trifluoro-m-tolyl)-3(2H)—pyridazinone |

-continued

| Common Name | Chemical Name |
|---|---|
| oryzalin | 3,4-dinitro-N,N—dipropylsulfanilamide |
| oxadiazon | 2-tert-butyl-4-(2,4-dichloro-5-isopropoxyphenyl)$\Delta^2$-1,3,4-oxadiazolin-5-one |
| oxyfluorfen | 2-chloro-1-(3-ethoxy-4-nitrophenoxy)-4-(trifluoromethyl)benzene |
| paraquat | 1,1′-dimethyl-4,4′-bipyridinium ion |
| PBA | chlorinated benzoic acid |
| pendimethalin | N—(1-ethylpropyl)-3,4-dimethyl-2,6-dinitrobenzenamine |
| perfluidone | 1,1,1-trifluoro-N—[2-methyl-4-(phenylsulfonyl)phenyl]methanesulfonamide |
| picloram | 4-amino-3,5,6-trichloropicolinic acid |
| procyazine | 2-[[4-chloro-6-(cyclopropylamino)-1,3,5-triazine-2-yl]amino]-2-methylpropanenitrile |
| profluralin | N—(cyclopropylmethyl)-α,α,α-trifluoro-2,6-dinitro-N—propyl-p-toluidine |
| prometon | 2,4-bis(isopropylamino)-6-methoxy-s-triazine |
| prometryn | 2,4-bis(isopropylamino)-6-(methylthio)-s-triazine |
| pronamide | 3,5-dichloro N—(1,1-dimethyl-2-propynyl)benzamide |
| propachlor | 2-chloro-N—isopropylacetanilide |
| propanil | 3′,4′-dichloropropionalide |
| propazine | 2-chloro-4,6-bis(isopropylamino)-s-triazine |
| propham | isopropyl carbanilate |
| prosulfalin | N—[[4-(dipropylamino)-3,5-dinitrophenyl]sulfonyl]-S,S—dimethylsulfilimine |
| prynachlor | 2-chloro-N—(1-methyl-2-propynyl)acetanilide |
| quinofop ethyl | 2-[4-(6-chloroquinoxalin-2-yloxy)phenoxypropanoic acid, ethyl ester |
| guizalofop | 2-[4-[(6-chloro-2-quinoxalinyl)oxy]phenoxy]propionic acid, ethyl ester |
| secbumeton | N—ethyl-6-methoxy-N′(1-methylpropyl)-1,3,5-triazine-2,4-diamine |
| sethoxydim | 2-[1-(ethoxyimino)butyl]-5-[2-(ethylthio)propyl]-3-hydroxy-2-cyclohexene-1-one |
| siduron | 1-(2-methylcyclohexyl)-3-phenylurea |
| simazine | 2-chloro-4,6-bis(ethylamino)-s-triazine |
| simetryn | 2,4-bis(ethylamino)-6-(methylthio)-s-triazine |
| supriox | 2-[1-(2,5-dimethylphenyl)ethylsulfonyl]-pyridine-N—oxide |
| TCA | trichloroacetic acid |
| tebuthiuron | N—[5-(1,1-dimethylethyl)-1,3,4-thiadiazol-2-yl]-N,N′—dimethylurea |
| terbacil | 3-tert-butyl-5-chloro-6-methyluracil |
| terbuchlor | N—(butoxymethyl)-2-chloro-N—[2-(1,1-dimethylethyl)-6-methylphenyl]-acetamide |
| terbuthylazine | 2-(tert-butylamino)-4-chloro-6-(ethylamino)-s-triazine |
| terbutol | 2,6-di-tert-butyl-p-tolyl methylcarbamate |
| terbutryn | 2-(tert-butylamino)-4-(ethylamino)-6-(methylthio)-s-triazine |
| tetrafluron | N,N—dimethyl-N′—[3-(1,1,2,2-tetrafluoroethoxy)phenyl]urea |
| thiameturon methyl | 3-[[(4-methoxy-6-methyl-1,3,5-triazin-2-yl)aminocarbonyl]aminosulfonyl]-2-thiophenecarboxylic acid, methyl ester |
| thiobencarb | S—[(4-chlorophenyl)methyl]diethylcarbamothioate |
| triallate | S—(2,3,3-trichloroallyl)diisopropylthiocarbamate |
| trifluralin | α,α,α-trifluoro-2,6-dinitro-N,N—propyl-p-toluidine |
| trimeturon | 1-(p-chlorophenyl)-2,3,3-trimethylpseudourea |
| vernolate | S—propyl dipropylthiocarbamate |
| 2,3,6-TBA[b] | ethyl 5-[2-chloro-4-(trifluoromethyl)phenoxy]-2-nitrobenzoic acid<br>2,3,6-trichlorobenzoic acid |
| 2,4-D | (2,4-dichlorophenoxy)acetic acid |
| 2,4-DB | 4-(2,4-dichlorophenoxy)butyric acid |

-continued

| Common Name | Chemical Name |
|---|---|
| 2,4-DEP | tris[2-(2,4-dichlorophenoxy)ethyl] phosphite |

| Trade Name or Code Number | Chemical Name |
|---|---|
| PPG-1013 | 5-(2-chloro-4-(trifluoromethyl)phenoxy)-2-nitroacetophenone oxime-O—acetic acid, methyl ester |
| FMC 57020 | 2-(2′-chlorophenyl)methyl-4,4-dimethyl-3-isoxazolidinone |
| AC 222,293 | 6-(4-isopropyl-4-methyl-5-oxo-2-imidazolin-2-yl)-m-toluic acid, methyl ester and 6-(4-isopropyl-4-methyl-5-oxo-2-imidazolin-2-yl)-p-toluic acid, methyl ester |
| AC 252,925 | 2-(4-isopropyl-4-methyl-5-oxo-2-imidazolin-2-yl)nicotinic acid with isopropyl amine (1:1) |
| Express ® | 2-[[N—(4-methoxy-6-methyl-1,3,5-triazine-2-yl)-N—methylaminocarbonyl]-aminosulfonyl]benzoic acid, methyl ester |
| — | 3-methyl-6-[4,5-dihydro-5-methyl-5-(1-methylethyl)-4-oxo-1H—imidazol-2-yl] benzoic acid, methyl ester |
| — | 4-chloro-2-[[[(4-methoxy-6-methyl-1,3,5-triazin-2-yl)aminocarbonyl]aminosulfonyl)benzoic acid, (1-methylethyl) ester |

The herbicidal properties of the subject compounds were discovered in a number of greenhouse tests. The test procedures and results follow.

TABLE 10

Test Compounds

| Compound | Q | X | Y | Z |
|---|---|---|---|---|
| 1 | CH$_2$CH$_2$N$_3$ | CH$_3$ | OCH$_3$ | N |
| 2 | CH$_2$CH$_2$N$_3$ | Cl | OCH$_3$ | CH |
| 3 | CH$_2$CH$_2$N$_3$ | CH$_3$ | OCH$_3$ | CH |
| 4 | CH$_2$CH$_2$N$_3$ | OCH$_3$ | OCH$_3$ | CH |

Test A

Seeds of crabgrass (*Digitaria spp.*), barnyardgrass (*Echinochloa crus-galli*), giant foxtail (*Setaria faberi*), wild oats (*Avena fatua*), velvetleaf (*Abutilon theophrasti*), morningglory (*Ipomoea spp.*), cocklebur (*Xanthium pensylvanicum*), sorghum, corn, soybean, sugarbeet, cotton, rice, wheat, barley and purple nutsedge (*Cyperus rotundus*) tubers were planted and treated preemergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10= complete kill. The accompanying descriptive symbols have the following meanings:

C=chlorosis/necrosis;
B=burn;
D=defoliation;
E=emergence inhibition;
G=growth retardation;
H=formative effect;
U=unusual pigmentation;
X=axillary stimulation;
S=albinism; and
6Y=abscised buds or flowers.

vensis), blackgrass (*Alopecurus myosuroides*), and rape (*Brassica napus*). The plants were grown for approximately fourteen days, then sprayed postemergence with the chemicals dissolved in a non-phytotoxic solvent.

Preemergence

Three round pans (25 cm diameter by 12.5 cm deep) were filled with Sassafras sandy loam soil. One pan was planted with nutsedge tubers, crabgrass, sicklepod, jimsonweed, velvetleaf, lambsquarters, rice and teaweed. The second pot was planted with green foxtail, cocklebur, morningglory, cotton, johnsongrass, barnyardgrass, corn, soybean and giant foxtail. The third pot was planted with wheat, barley, wild buckwheat, cheat-

TABLE A

| | CMPD 1 | | CMPD 2 | | CMPD 3 | | CMPD 4 | |
|---|---|---|---|---|---|---|---|---|
| RATE = KG/HA | 0.05 | 0.01 | 0.05 | 0.01 | 0.05 | 0.01 | 0.05 | 0.01 |
| POSTEMERGENCE | | | | | | | | |
| COTTON | 9H | 3C,8H | 9G | 3C,9H | 9C | 9H | 5C,9G | 3C,9G |
| MORNINGLORY | 3C,7G | 3G | 4C,9G | 2C,6G | 9C | 2C,7G | 4C,8H | 3C,7G |
| COCKLEBUR | 5C,9G | 4C,9G | 5C,9G | 4C,9G | 9C | 5C,9G | 10C | 9C |
| PURPLE NUTSEDGE | 3G | 0 | 3C,9G | 2C,7G | 3C,9G | 4C,8G | 4C,9G | 5C,9G |
| CRABGRASS | 0 | 0 | 2G | 0 | 3C,7G | 2G | 3C,8G | 2C,5G |
| BARNYARDGRASS | 3G | 0 | 9C | 9C | 9C | 10C | 10C | 10C |
| WILD OATS | 0 | 0 | 3G | 0 | 4C,8G | 4G | 3C,5G | 2G |
| WHEAT | 0 | 0 | 2G | 0 | 2C,6G | 3G | 4G | 2G |
| CORN | 5C,9G | 3C,9H | 3C,5G | 2C,3G | 3C,9G | 4C,9G | 3U,9G | 3C,8G |
| SOYBEANS | 6G | 1H | 4H | 1H | 5C,9G | 8H | 9C | 3C,8G |
| RICE | 2C | 0 | 5C,9G | 2C,7G | 9C | 4C,9G | 9C | 5C,9G |
| SORGHUM | 4C,9G | 4C,9G | 5C,9G | 4C,9G | 10C | 5C,9G | 9C | 9G |
| SUGARBEETS | 9C | 9C | 10C | 7G | 10C | 10C | 10C | 10C |
| VELVETLEAF | 9C | 4C,9H | 5C,9G | 3C,7G | 10C | 9C | 10C | 10C |
| GIANT FOXTAIL | 0 | 0 | 3C,7G | 2G | 9C | 3C,7G | 9C | 9C |
| BARLEY | 0 | 0 | 5G | 3G | 3C,8H | 2C,5G | 2C,9G | 7G |
| DOWNY BROME | 3G | 0 | 3C,5G | 3G | 5C,9G | 4C,8G | 5C,9G | 3C,7G |
| PREEMERGENCE | | | | | | | | |
| COTTON | 7H | 6G | 5G | 0 | 8H | 2C,6G | 9G | 5G |
| MORNINGLORY | 9G | 8G | 3G | 0 | 0 | 2G | 2G | 0 |
| COCKLEBUR | 9H | 9H | — | 1H | 9H | 2C,5H | 8H | 2C,2H |
| PURPLE NUTSEDGE | 3G | 4G | 9G | 0 | 10E | 0 | 10E | 2C,5G |
| CRABGRASS | 5G | 0 | 5G | 0 | 3C,7G | 2C,6G | 3G | 2C,3G |
| BARNYARDGRASS | 3G | 0 | 9H | 2G | 9H | 2C,5G | 9H | 3C,9H |
| WILD OATS | 0 | 0 | 4G | 0 | 7G | 3G | 3C,7G | 3G |
| WHEAT | 0 | 0 | 4G | 0 | 6G | 2G | 2C,6G | 2G |
| CORN | 9H | 3C,7G | 3C,8H | 2G | 3C,9H | 2C,3G | 3C,9H | 3C,7G |
| SOYBEANS | 2C,3H | 2C,3G | 2G | 0 | 2C,7G | 2C,2H | 2C,5G | 2C,2H |
| RICE | 2G | 0 | 9H | 8H | 9H | 8H | 10E | 9H |
| SORGHUM | 3C,9G | 8G | 5C,9H | 9H | 9H | 3C,7H | 9G | 3C,9G |
| SUGARBEETS | 5C,9G | 9G | 9G | 7G | 5C,9G | 9G | 9G | 8H |
| VELVETLEAF | 7G | 3H | 3H | 0 | 7H | 6H | 7H | 1C,1H |
| GIANT FOXTAIL | 0 | 0 | 5G | 0 | 3C,8H | 5G | 3C,8H | 3C,8G |
| BARLEY | 2C,5G | 0 | 2C,8G | 2G | 9G | 2C,8G | 2C,8G | 8G |
| DOWNY BROME | 5G | 0 | 9C | 3C,7G | 9H | 2C,8G | 9H | 3C,9G |

Test B

Postemergence

Three round pans (25 cm diameter by 12.5 cm deep) were filled with Sassafras sandy loam soil. One pan was planted with nutsedge (*Cyperus rotundus*) tubers, crabgrass (*Digitaria sanguinalis*), sicklepod (*Cassia obtusifolia*), jimsonweed (*Datura stramonium*), velvetleaf (*Abutilon theophrasti*), lambsquarters (*Chenopodium album*), rice (*Oryza sativa*) and teaweed (*Sida spinosa*). The second pot was planted with green foxtail (*Setaria viridis*), cocklebur (*Xanthium pensylvanicum*), morningglory (*Ipomoea hederacea*), cotton (*Gossypium hirsutum*), johnsongrass (*Sorghum halepense*), barnyardgrass (*Echinochloa crus-galli*), corn (*Zea mays*), soybean (*Glycine max*) and giant foxtail (*Setaria faberi*). The third pot was planted with wheat (*Triticum aestivum*), barley (*Hordeum vulgare*), wild buckwheat (*Polgonum convolvulus L.*), cheatgrass (*Bromus secalinus L.*), sugarbeet (*Beta vulgaris*), wild oat (*Avena fatua*), viola (*Viola ar-* grass, sugarbeet, wild oat, viola, blackgrass grass and rape. The three pans were sprayed preemergence with the chemicals dissolved in a non-phytotoxic solvent.

Treated plants and controls were maintained in the greenhouse for 24 days, then all rated plants were compared to controls and visually rated for plant response.

Response ratings are based on a scale of 0 to 100 where 0= no effect and 100= complete control. A dash (-) response means no test.

Response ratings are contained in Table B.

TABLE B

| | CMPD 1 | | | |
|---|---|---|---|---|
| RATE = G/HA | 0250 | 0062 | 0016 | 0004 |
| POSTEMERGENCE' | | | | |
| GIANT FOXTAIL | 60 | 40 | 0 | 0 |
| VELVETLEAF | 100 | 100 | 90 | 70 |
| SUGARBEET | 100 | 100 | 100 | 80 |
| CRABGRASS | 50 | 30 | 0 | 0 |
| PRICKLY SIDA | 70 | 50 | 30 | 0 |
| JIMSONWEED | 100 | 100 | 90 | 80 |

TABLE B-continued

|  | 30 | 0 | 0 | 0 |
|---|---|---|---|---|
| RICE | 30 | 0 | 0 | 0 |
| COCKLEBUR | 100 | 100 | 100 | 90 |
| COTTON | 90 | 70 | 50 | 30 |
| SOYBEANS | 100 | 70 | 30 | 0 |
| BARNYARDGRASS | 100 | 60 | 40 | 30 |
| WILD OATS | 50 | 30 | 0 | 0 |
| MORNINGLORY | 90 | 70 | 50 | 30 |
| WHEAT | 0 | 0 | 0 | 0 |
| SICKLEPOD | 90 | 60 | 30 | 0 |
| JOHNSONGRASS | 90 | 70 | 50 | 30 |
| PURPLE NUTSEDGE | 70 | 50 | 30 | 0 |
| CORN | 100 | 100 | 70 | 40 |
| WILD BUCKWHEAT | 100 | 100 | 100 | 90 |
| BLACKGRASS | 80 | 50 | 30 | 0 |
| RAPE | 100 | 100 | 95 | 90 |
| BARLEY | 0 | 0 | 0 | 0 |
| GREEN FOXTAIL | 70 | 30 | 0 | 0 |
| LAMBSQUARTER | 100 | 90 | 80 | 70 |
| CHICKWEED | 100 | 100 | 90 | 80 |
| DOWNY BROME | 70 | 30 | 0 | 0 |

| | CMPD 1 | | | |
|---|---|---|---|---|
| RATE = G/HA | 0250 | 0062 | 0016 | 0004 |
| PREEMERGENCE | | | | |
| GIANT FOXTAIL | 50 | 30 | 0 | — |
| VELVETLEAF | 70 | 60 | 50 | 40 |
| SUGARBEET | 100 | 100 | 95 | — |
| CRABGRASS | 50 | 30 | 0 | 0 |
| PRICKLY SIDA | 70 | 50 | 30 | 0 |
| JIMSONWEED | 70 | 50 | 30 | 0 |
| RICE | 70 | 50 | 0 | 0 |
| COCKLEBUR | 90 | 70 | 50 | 30 |
| COTTON | 80 | 70 | 50 | 0 |
| SOYBEANS | 80 | 50 | 0 | — |
| BARNYARDGRASS | 80 | 50 | 0 | — |
| WILD OATS | 50 | 0 | 0 | — |
| MORNINGLORY | 90 | 60 | 30 | 0 |
| WHEAT | 0 | 0 | 0 | — |
| SICKLEPOD | 90 | 60 | 30 | 0 |
| JOHNSONGRASS | 50 | 30 | 0 | — |
| PURPLE NUTSEDGE | 80 | 70 | 50 | 0 |
| CORN | 80 | 60 | 0 | — |
| WILD BUCKWHEAT | 90 | 70 | 50 | — |
| BLACKGRASS | 100 | 100 | 50 | — |
| RAPE | 90 | 70 | 0 | — |
| BARLEY | 0 | 0 | 0 | — |
| GREEN FOXTAIL | 50 | 30 | 0 | 0 |
| LAMBSQUARTER | 90 | 80 | 70 | 60 |
| CHICKWEED | 100 | 100 | 100 | — |
| DOWNY BROME | 50 | 30 | 0 | — |

| | CMPD 2 | | | |
|---|---|---|---|---|
| RATE = G/HA | 0250 | 0062 | 0016 | 0004 |
| POSTEMERGENCE' | | | | |
| GIANT FOXTAIL | 90 | 70 | 50 | 30 |
| VELVETLEAF | 100 | 100 | 60 | 30 |
| SUGARBEET | 100 | 80 | 50 | 30 |
| CRABGRASS | 50 | 30 | 0 | 0 |
| PRICKLY SIDA | 90 | 80 | 50 | 30 |
| JIMSONWEED | 100 | 90 | 70 | 30 |
| RICE | 100 | 100 | 70 | 60 |
| COCKLEBUR | 100 | 100 | 80 | 60 |
| COTTON | 90 | 80 | 70 | 40 |
| SOYBEANS | 70 | 50 | 30 | 0 |
| BARNYARDGRASS | 100 | 100 | 90 | 60 |
| WILD OATS | 50 | 30 | 0 | 0 |
| MORNINGLORY | 100 | 100 | 60 | 30 |
| WHEAT | 50 | 30 | 0 | 0 |
| SICKLEPOD | 60 | 30 | 0 | 0 |
| JOHNSONGRASS | 90 | 80 | 70 | 60 |
| PURPLE NUTSEDGE | 100 | 80 | 50 | 30 |
| CORN | 80 | 50 | 0 | 0 |
| WILD BUCKWHEAT | 100 | 100 | 70 | 60 |
| BLACKGRASS | 60 | 30 | 0 | 0 |
| RAPE | 100 | 100 | 95 | 90 |
| BARLEY | 70 | 50 | 30 | 0 |
| GREEN FOXTAIL | 100 | 90 | 70 | 60 |
| LAMBSQUARTER | 100 | 90 | 60 | 30 |
| CHICKWEED | 100 | 90 | 80 | 70 |
| DOWNY BROME | 60 | 30 | 0 | 0 |

| | CMPD 2 | | | |
|---|---|---|---|---|
| RATE = G/HA | 0250 | 0062 | 0016 | 0004 |
| PREEMERGENCE | | | | |
| GIANT FOXTAIL | 90 | 60 | 30 | — |
| VELVETLEAF | 60 | 50 | 40 | 30 |
| SUGARBEET | 100 | 90 | 80 | — |
| CRABGRASS | 50 | 30 | 0 | 0 |
| PRICKLY SIDA | 60 | 30 | 0 | 0 |
| JIMSONWEED | 70 | 50 | 30 | 0 |
| RICE | 100 | 80 | 50 | 30 |
| COCKLEBUR | 90 | 60 | 30 | 0 |
| COTTON | 70 | 50 | 30 | — |
| SOYBEANS | 60 | 30 | 0 | — |
| BARNYARDGRASS | 100 | 90 | 80 | — |
| WILD OATS | 0 | 0 | 0 | — |
| MORNINGLORY | 80 | 50 | 0 | 0 |
| WHEAT | 30 | 0 | 0 | — |
| SICKLEPOD | 0 | 0 | 0 | 0 |
| JOHNSONGRASS | 80 | 70 | 50 | — |
| PURPLE NUTSEDGE | 60 | 50 | 40 | 0 |
| CORN | 70 | 30 | 0 | — |
| WILD BUCKWHEAT | 90 | 70 | 50 | — |
| BLACKGRASS | 100 | 70 | 50 | — |
| RAPE | 100 | 90 | 70 | — |
| BARLEY | 30 | 0 | 0 | — |
| GREEN FOXTAIL | 90 | 60 | 30 | 0 |
| LAMBSQUARTER | 90 | 70 | 50 | 30 |
| CHICKWEED | 80 | 50 | 30 | — |
| DOWNY BROME | 70 | 50 | 30 | — |

| | CMPD 3 | | | |
|---|---|---|---|---|
| RATE = G/HA | 0062 | 0016 | 0004 | 0001 |
| POSTEMERGENCE' | | | | |
| GIANT FOXTAIL | 100 | 100 | 70 | 50 |
| VELVETLEAF | 100 | 100 | 100 | 60 |
| SUGARBEET | 100 | 100 | 90 | 80 |
| CRABGRASS | 60 | 30 | 0 | 0 |
| PRICKLY SIDA | 100 | 100 | 60 | 30 |
| JIMSONWEED | 100 | 80 | 50 | 30 |
| RICE | 90 | 80 | 60 | 30 |
| COCKLEBUR | 100 | 100 | 100 | 70 |
| COTTON | 100 | 100 | 70 | 50 |
| SOYBEANS | 100 | 100 | 70 | 30 |
| BARNYARDGRASS | 100 | 100 | 90 | 70 |
| WILD OATS | 50 | 40 | 30 | 0 |
| MORNINGLORY | 70 | 60 | 50 | 30 |
| WHEAT | 60 | 30 | 0 | 0 |
| SICKLEPOD | 100 | 70 | 30 | 0 |
| JOHNSONGRASS | 100 | 90 | 80 | 70 |
| PURPLE NUTSEDGE | 100 | 100 | 70 | 50 |
| CORN | 70 | 60 | 50 | 30 |
| WILD BUCKWHEAT | 100 | 100 | 100 | 60 |
| BLACKGRASS | 90 | 60 | 30 | 0 |
| RAPE | 100 | 100 | 90 | 60 |
| BARLEY | 70 | 50 | 30 | 0 |
| GREEN FOXTAIL | 100 | 90 | 80 | 60 |
| LAMBSQUARTER | 100 | 100 | 90 | 80 |
| CHICKWEED | 100 | 100 | 90 | 70 |
| DOWNY BROME | 90 | 60 | 30 | 0 |

| | CMPD 3 | | | |
|---|---|---|---|---|
| RATE = G/HA | 0250 | 0062 | 0016 | 0004 |
| PREEMERGENCE | | | | |
| GIANT FOXTAIL | 90 | 60 | 30 | — |
| VELVETLEAF | 70 | 50 | 30 | 0 |
| SUGARBEET | 100 | 95 | 90 | — |
| CRABGRASS | 80 | 50 | 30 | 0 |
| PRICKLY SIDA | 90 | 70 | 50 | 30 |
| JIMSONWEED | 70 | 50 | 30 | 0 |
| RICE | 90 | 70 | 50 | 30 |
| COCKLEBUR | 90 | 70 | 50 | 30 |
| COTTON | 80 | 50 | 30 | 0 |
| SOYBEANS | 60 | 40 | 0 | — |
| BARNYARDGRASS | 100 | 80 | 60 | — |
| WILD OATS | 50 | 30 | 0 | — |
| MORNINGLORY | 90 | 60 | 30 | 0 |
| WHEAT | 60 | 30 | 0 | — |
| SICKLEPOD | 90 | 70 | 50 | 30 |
| JOHNSONGRASS | 90 | 70 | 50 | — |
| PURPLE NUTSEDGE | 100 | 70 | 30 | 0 |

TABLE B-continued

| | | | | |
|---|---|---|---|---|
| CORN | 80 | 50 | 30 | — |
| WILD BUCKWHEAT | 90 | 70 | 50 | — |
| BLACKGRASS | 70 | 50 | 30 | — |
| RAPE | 90 | 70 | 50 | — |
| BARLEY | 0 | 0 | 0 | — |
| GREEN FOXTAIL | 100 | 90 | 70 | 50 |
| LAMBSQUARTER | 90 | 80 | 70 | 50 |
| CHICKWEED | 90 | 80 | 70 | — |
| DOWNY BROME | 60 | 50 | 30 | — |

| | CMPD 4 | | | |
|---|---|---|---|---|
| RATE = G/HA | 0062 | 0016 | 0004 | 0001 |
| POSTEMERGENCE' | | | | |
| GIANT FOXTAIL | 100 | 100 | 70 | 50 |
| VELVETLEAF | 100 | 100 | 100 | 70 |
| SUGARBEET | 100 | 100 | 100 | 100 |
| CRABGRASS | 80 | 50 | 30 | 0 |
| PRICKLY SIDA | 100 | 90 | 60 | 30 |
| JIMSONWEED | 100 | 70 | 50 | 30 |
| RICE | 90 | 80 | 70 | 60 |
| COCKLEBUR | 100 | 100 | 90 | 80 |
| COTTON | 100 | 90 | 60 | 30 |
| SOYBEANS | 100 | 90 | 70 | 50 |
| BARNYARDGRASS | 100 | 100 | 90 | 60 |
| WILD OATS | 50 | 30 | 0 | 0 |
| MORNINGLORY | 80 | 70 | 50 | 30 |
| WHEAT | 50 | 30 | 0 | 0 |
| SICKLEPOD | 100 | 90 | 60 | 30 |
| JOHNSONGRASS | 100 | 70 | 50 | 30 |
| PURPLE NUTSEDGE | 100 | 100 | 90 | 70 |
| CORN | 70 | 60 | 50 | 40 |
| WILD BUCKWHEAT | 100 | 100 | 100 | 70 |
| BLACKGRASS | 90 | 70 | 50 | 30 |
| RAPE | 100 | 100 | 90 | 70 |
| BARLEY | 60 | 30 | 0 | 0 |
| GREEN FOXTAIL | 100 | 100 | 90 | 70 |
| LAMBSQUARTER | 100 | 70 | 50 | 30 |
| CHICKWEED | 100 | 100 | 100 | 100 |
| DOWNY BROME | 90 | 70 | 50 | 30 |

| | CMPD 4 | | | |
|---|---|---|---|---|
| RATE = G/HA | 0250 | 0062 | 0016 | 0004 |
| PREEMERGENCE | | | | |
| GIANT FOXTAIL | 100 | 90 | 70 | — |
| VELVETLEAF | 70 | 50 | 30 | 0 |
| SUGARBEET | 100 | 90 | 70 | — |
| CRABGRASS | 90 | 60 | 30 | 0 |
| PRICKLY SIDA | 90 | 60 | 30 | 0 |
| JIMSONWEED | 40 | 30 | 20 | 0 |
| RICE | 90 | 80 | 70 | 50 |
| COCKLEBUR | 90 | 70 | 50 | 30 |
| COTTON | 90 | 60 | 30 | — |
| SOYBEANS | 80 | 30 | 0 | — |
| BARNYARDGRASS | 100 | 90 | 80 | — |
| WILD OATS | 50 | 30 | 0 | — |
| MORNINGLORY | 90 | 60 | 30 | — |
| WHEAT | 0 | 0 | 0 | — |
| SICKLEPOD | 80 | 50 | 30 | 0 |
| JOHNSONGRASS | 90 | 80 | 70 | — |
| PURPLE NUTSEDGE | 100 | 100 | 90 | 0 |
| CORN | 70 | 20 | 0 | — |
| WILD BUCKWHEAT | 90 | 70 | 50 | — |
| BLACKGRASS | 90 | 70 | 50 | — |
| RAPE | 90 | 80 | 70 | — |
| BARLEY | 60 | 30 | 0 | — |
| GREEN FOXTAIL | 100 | 90 | 80 | 60 |
| LAMBSQUARTER | 90 | 70 | 50 | 30 |
| CHICKWEED | 100 | 90 | 80 | — |
| DOWNY BROME | 90 | 60 | 30 | — |

As many different embodiments of this invention may be made without departing from the spirit and scope thereof, it is to be understood that the invention is not limited to the specific embodiments disclosed herein but rather shall be defined by the scope of the appended claims.

What is claimed:
1. A compound selected from

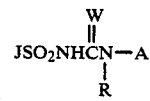

wherein
J is

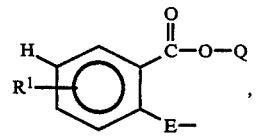

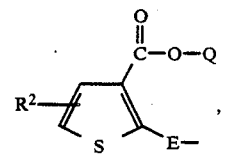

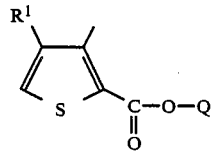

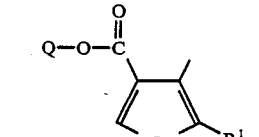

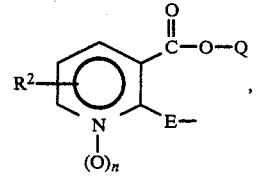

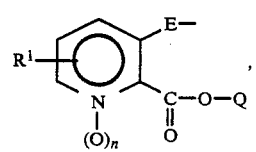

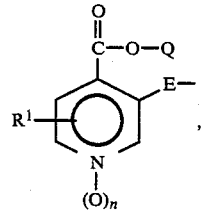

-continued

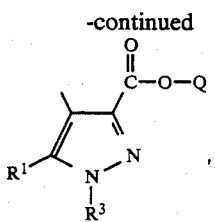
J-9

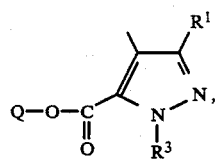
J-10

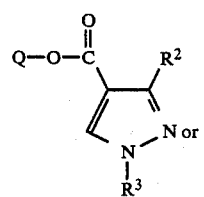
J-11

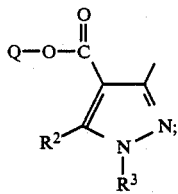
J-12

Q is

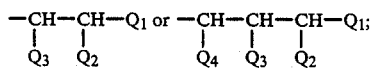

$Q_1$ is $N_3$, SCN or $NO_2$;
$Q_2$, $Q_3$ and $Q_4$ are independently H or $CH_3$;
E is a single bond or —$CH_2$—;
R is H or $CH_3$;
W is O or S;
$R^1$ is H, $C_1$-$C_3$ alkyl, $C_1$-$C_3$ haloalkyl, halogen, CN, nitro, $C_1$-$C_3$ alkoxy, $C_1$-$C_3$ haloalkoxy, $C_1$-$C_3$ alkylthio, $C_1$-$C_3$ alkylsulfinyl, $C_1$-$C_3$ alkylsulfonyl, $SCF_2H$, $NH_2$, $NHCH_3$, $N(CH_3)_2$ or $C_1$-$C_2$ alkyl substituted with one $C_1$-$C_2$ alkoxy, $C_1$-$C_2$ haloalkoxy, SH, $SCH_3$, CN or OH;
$R^2$ is H, F, Cl, Br, $C_1$-$C_2$ alkyl, $C_1$-$C_2$ haloalkyl or $C_1$-$C_2$ alkoxy;
$R^3$ is H, $C_1$-$C_3$ alkyl, $C_1$-$C_2$ haloalkyl, $C_3$-$C_4$ alkenyl, $C_3$-$C_4$ alkynyl, $CH_2CN$, phenyl or phenyl substituted by F, Cl, $CH_3$ or $OCH_3$;
n is 0 or 1;
A is

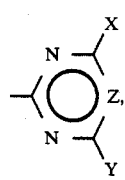
A-1

X is H, $C_1$-$C_4$ alkyl,
$C_1$-$C_4$ alkoxy, $C_1$-$C_4$ haloalkoxy,
$C_1$-$C_4$ haloalkyl, $C_1$-$C_4$ haloalkylthio,
$C_1$-$C_4$ alkylthio, halogen, $C_2$-$C_5$ alkoxyalkyl,
$C_2$-$C_5$ alkoxyalkoxy, amino, $C_1$-$C_3$ alkylamino,
di($C_1$-$C_3$alkyl)amino or $C_3$-$C_5$ cycloalkyl;
Y is H, $C_1$-$C_4$ alkyl, $C_1$-$C_4$ alkoxy, $C_1$-$C_4$ haloalkoxy,
$C_1$-$C_4$ haloalkylthio, $C_1$-$C_4$ alkylthio,
$C_2$-$C_5$ alkoxyalkyl, $C_2$-$C_5$ alkoxyalkoxy, amino,
$C_1$-$C_3$ alkylamino, di($C_1$-$C_3$ alkyl)amino, $C_3$-$C_4$ alkenyloxy, $C_3$-$C_4$ alkynyloxy, $C_2$-$C_5$ alkylthioalkyl, $C_1$-$C_4$ haloalkyl, $C_2$-$C_4$ alkynyl, azido, cyano, $C_2$-$C_5$ alkylsulfinylalkyl, $C_2$-$C_5$ alkylsulfonylalkyl,

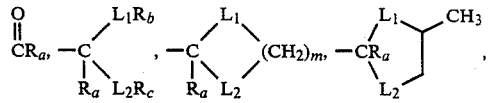

$CH_2CN$, $CH_2CO_2CH_3$, $CH_2OH$ or $N(OCH_3)CH_3$;
m is 2 or 3;
$L_1$ and $L_2$ are independently O or S;
$R_a$ is H or $C_1$-$C_3$ alkyl;
$R_b$ and $R_c$ are independently $C_1$-$C_3$ alkyl;
Z is CH and their agriculturally suitable salts; provided that
(a) when X is Cl, F, Br or I, then Y is $OCH_3$, $OC_2H_5$, $N(OCH_3)CH_3$, $NHCH_3$, $N(CH_3)_2$ or $OCF_2H$;
(b) when W is S, then R is H, A is A-1 and Y is $CH_3$, $OCH_3$, $OC_2H_5$, $CH_2OCH_3$, $C_2H_5$, $CF_3$, $SCH_3$, $OCH_2CH=CH_2$, $OCH_2C≡CH$, $OCH_2CH_2OCH_3$, $CH(OCH_3)_2$ or 1,3-dioxolan-2-yl; and
(c) $Q_2$, $Q_3$ and $Q_4$ are not simultaneously methyl.

2. A compound of claim 1 where
E is a single bond; and
W is O.

3. A compound of claim 1 where
E is $CH_2$; and
W is O.

4. A compound of claim 2 where
X is $C_1$-$C_2$ alkyl, $C_1$-$C_2$ alkoxy, Cl, F, Br, I, $OCF_2H$, $CH_2F$, $CF_3$, $OCH_2CH_2F$, $OCH_2CHF_2$, $OCH_2CF_3$, $CH_2Cl$ or $CH_2Br$;
Y is H, $C_1$-$C_2$ alkyl, $C_1$-$C_2$ alkoxy, $CH_2OCH_3$, $CH_2OCH_2CH_3$, $NHCH_3$, $N(OCH_3)CH_3$, $N(CH_3)_2$, $CF_3$, $SCH_3$, $OCH_2CH=CH_2$, $OCH_2C≡CH$, $OCH_2CH_2OCH_3$, $CH_2SCH_3$,

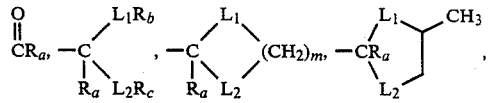

$OCF_2H$, $SCF_2H$, $OCF_2Br$, cyclopropyl, C≡CH or C≡$CCH_3$;
$R_a$ is H or $CH_3$; and
$R_b$ and $R_c$ are $C_1$-$C_2$ alkyl.

5. A compound of claim 4 where
n is 0;
X is $CH_3$, $OCH_3$, $OCH_2CH_3$, Cl or $OCF_2H$; and
Y is $CH_3$, $OCH_3$, $C_2H_5$, $CH_2OCH_3$, $NHCH_3$, $CH(OCH_3)_2$ or cyclopropyl.

6. A compound of claim 5 where
R is H;
$R^1$ is H, $CH_3$, $CF_3$, Cl, CN, $SCH_3$, $NHCH_3$, $N(CH_3)_2$, $CH_2OCH_3$ or $CH_2CN$;
$R^2$ is H, Cl, Br, $CH_3$ or $OCH_3$; and $R^3$ is H, $CH_3$, $CH_2CF_3$ or phenyl.

7. A compound of claim 6 where J is J-1.
8. A compound of claim 6 where J is J-2.
9. A compound of claim 6 where J is J-3.
10. A compound of claim 6 where J is J-4.
11. A compound of claim 6 where J is J-5.
12. A compound of claim 6 where J is J-6.
13. A compound of claim 6 where J is J-7.
14. A compound of claim 6 where J is J-8.
15. A compound of claim 6 where J is J-9.
16. A compound of claim 6 where J is J-10.
17. A compound of claim 6 where J is J-11.
18. A compound of claim 6 where J is J-12.
19. A compound of claim 6 wherein $Q_1$ is $N_3$.
20. A compound of claim 6 wherein $Q_1$ is SCN.
21. A compound of claim 6 wherein $Q_1$ is $NO_2$.
22. The compound of claim 1 which is 2benzoic acid 2-azidoethyl ester.
23. A composition suitable for controlling the growth of undesired vegetation which comprises an effective amount of a compound of claim 1 and at least one of the following: surfactant, solid or liquid diluent.
24. A composition suitable for controlling the growth of undesired vegetation which comprises an effective amount of a compound of claim 2 and at least one of the following: surfactant, solid or liquid diluent.
25. A composition suitable for controlling the growth of undesired vegetation which comprises an effective amount of a compound claim 3 and at least one of the following: surfactant, solid or liquid diluent.
26. A composition suitable for controlling the growth of undesired vegetation which comprises an effective amount of a compound of claim 4 and at least one of the following: surfactant, solid or liquid diluent.
27. A composition suitable for controlling the growth of undesired vegetation which comprises an effective amount of a compound of claim 5 and at least one of the following: surfactant, solid or liquid diluent.
28. A composition suitable for controlling the growth of undesired vegetation which comprises an effective amount of a compound of claim 6 and at least one of the following: surfactant, solid or liquid diluent.
29. A composition suitable for controlling the growth of undesired vegetation which comprises an effective amount of a compound of claim 7 and at least one of the following: surfactant, solid or liquid diluent.
30. A method for controlling the growth of undesired vegetation which comprises applying to the locus to be protected an effective amount of a compound of claim 1.
31. A method for controlling the growth of undesired vegetation which comprises applying to the locus to be protected an effective amount of a compound of claim 2.
32. A method for controlling the growth of undesired vegetation which comprises applying to the locus to be protected an effective amount of a compound of claim 3.
33. A method for controlling the growth of undesired vegetation which comprises applying to the locus to be protected an effective amount of a compound of claim 4.
34. A method for controlling the growth of undesired vegetation which comprises applying to the locus to be protected an effective amount of a compound of claim 5.
35. A method for controlling the growth of undesired vegetation which comprises applying to the locus to be protected an effective amount of a compound of claim 6.
36. A method for controlling the growth of undesired vegetation which comprises applying to the locus to be protected an effective amount of a compound of claim 7.

37. A compound selected from

I wherein

J is

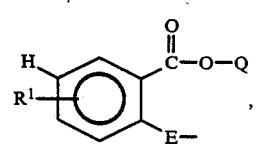

J-1

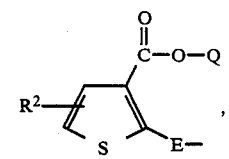

J-2

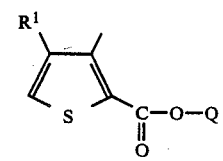

J-3

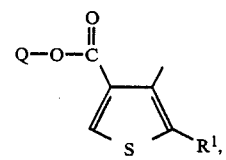

J-4

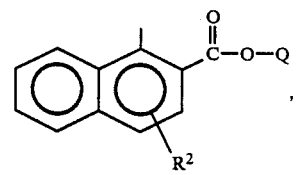

J-5

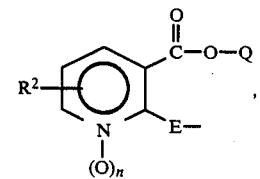

J-6

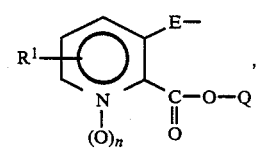

J-7

-continued

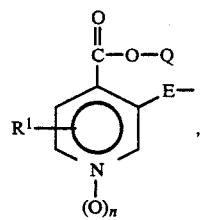
J-8

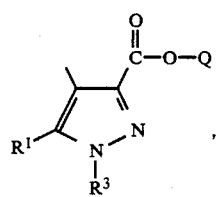
J-9

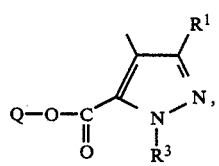
J-10

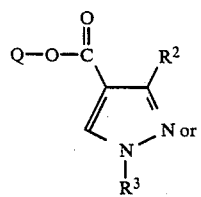
J-11

-continued

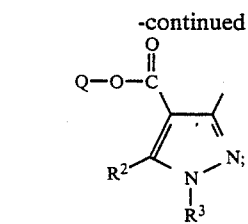
J-12

Q is $$-\overset{|}{\underset{Q_3}{C}}H-\overset{|}{\underset{Q_2}{C}}H-Q_1 \text{ or } -\overset{|}{\underset{Q_4}{C}}H-\overset{|}{\underset{Q_3}{C}}H-\overset{|}{\underset{Q_2}{C}}H-Q_1;$$

$Q_1$ is $N_3$, SCN or $NO_2$;
$Q_2$, $Q_3$ and $Q_4$ are independently H or $CH_3$;
E is a single bond or $-CH_2-$;
R is H or $CH_3$;
W is O or S;
$R^1$ is H, $C_1-C_3$ alkyl, $C_1-C_3$ haloalkyl, halogen, CN, nitro, $C_1-C_3$ alkoxy, $C_1-C_3$ haloalkoxy, $C_1-C_3$ alkylthio, $C_1-C_3$ alkylsulfinyl, $C_1-C_3$ alkylsulfonyl, $SCF_2H$, $NH_2$, $NHCH_3$, $N(CH_3)_2$ or $C_1-C_2$ alkyl substituted with one $C_1-C_2$ alkoxy, $C_1-C_2$ haloalkoxy, SH, $SCH_3$, CN or OH;
$R^2$ is H, F, Cl, Br, $C_1-C_2$ alkyl, $_1-C_2$haloalkyl or $C_1-C_2$ alkoxy;
$R^3$ is H, $C_1-C_3$ alkyl, $C_1-C_2$ haloalkyl, $C_3-C_4$ alkenyl, $C_3-C_4$ alkynyl, $CH_2CN$, phenyl or phenyl substituted by F, Cl, $CH_3$ or $OCH_3$;
n is 0 or 1;
A is

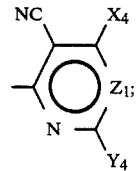

$Z_1$ is N;
$X_4$ is $CH_3$, $OCH_3$, $OC_2H_5$, $CH_2OCH_3$ or Cl; and
$Y_4$ is $CH_3$, $OCH_3$, $OC_2H_5$ or Cl;
and their agriculturally suitable salts; provided that
(a) $X_4$ and $Y_4$ are not simultaneously Cl; and
(b) $Q_2$, $Q_3$ and $Q_4$ are not simultaneously methyl.

* * * * *